US011834692B2

(12) United States Patent
Nair et al.

(10) Patent No.: US 11,834,692 B2
(45) Date of Patent: Dec. 5, 2023

(54) GALACTOSE TO TAGATOSE ISOMERIZATION AT MODERATE TEMPERATURES WITH HIGH CONVERSION AND PRODUCTIVITY

(71) Applicant: Trustees of Tufts College, Medford, MA (US)

(72) Inventors: Nikhil U. Nair, Medford, MA (US); Josef R. Bober, Medford, MA (US)

(73) Assignee: Trustees of Tufts College, Medford, WI (US)

( * ) Notice: Subject to any disclaimer, the term of this patent is extended or adjusted under 35 U.S.C. 154(b) by 141 days.

(21) Appl. No.: 17/168,499

(22) Filed: Feb. 5, 2021

(65) Prior Publication Data

US 2021/0269839 A1  Sep. 2, 2021

Related U.S. Application Data

(60) Provisional application No. 62/971,695, filed on Feb. 7, 2020.

(51) Int. Cl.
*C12P 19/24* (2006.01)
*C12N 9/90* (2006.01)
*C12P 19/02* (2006.01)

(52) U.S. Cl.
CPC .............. *C12P 19/24* (2013.01); *C12N 9/90* (2013.01); *C12P 19/02* (2013.01)

(58) Field of Classification Search
CPC . C12P 19/24; C12P 19/02; C12N 9/90; C12Y 503/01004
See application file for complete search history.

(56) References Cited

U.S. PATENT DOCUMENTS 7,396,664 B2   7/2008 Daly

FOREIGN PATENT DOCUMENTS

WO    WO 2017176875 A1 * 10/2017
WO       2019099649 A1    5/2019

OTHER PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Men et al. (Enzymatic conversion of d-galactose to d-tagatose: Cloning, overexpression and characterization of l-arabinose isomerase from Pediococcus pentosaceus PC-5, Microbiological Research (2014), 169: 171-178). (Year: 2014).*
Staudigl et al. (L-arabinose isomerase and D-xylose isomerase from Lactobacillus reuteri: characterization, coexpression in food grade host Lactobacillus plantarum, and application in the conversion of D-galactose and D-glucose. J. Agric. Food Chem. (2014), 62: 1617-1624). (Year: 2014).*
Yadav et al. (Permeabilization of Kluyveromyces marxianus with Mild Detergent for Whey Lactose hydrolysis and Augmentation of Mixed Culture. Appl Biochem Biotechnol (2014), 172: 3207-3222). (Year: 2014).*
Chi et al. (Agar degradation by microorganisms and agar-degrading enzymes. Appl Microbiol Biotechnol (2012) 94: 917-930). (Year : 2012).*
Gerken et al. Enzymatic cell wall degradation of Chlorella vulgaris and other microalgae for biofuels production. Planta (2013), 237: 239-253. (Year: 2013).*
Apel, A. R., et al. Evolved hexose transporter enhances xylose uptake and glucose/xylose coutilization in *Saccharomyces cerevisiae*. Sci. Rep. 6, 19512 (2016).
Bertelsen, H., et al. Fermentation of D-tagatose by human intestinal bacteria and dairy lactic acid bacteria. Microb. Ecol. Health Dis. 13, 87-95 (2001).
Bober, J. R., et al. "Surpassing thermodynamic, kinetic, and stability barriers to isomerization catalysis for tagatose biosynthesis." BioRxiv (2019): 547166.
Bober, J. R.; et al. Galactose to tagatose isomerization at moderate temperatures with high conversion and productivity. Nature Communications 2019, 10, 4548.
Bortone, N. et al. Immobilization of the recombinant (His)6-tagged l-arabinose isomerase from Thermotoga maritima on epoxy and cupper-chelate epoxy supports. Food Bioprod. Process. 95, 155-162 (2015).
Cheetham, P. S. J. et al. Bioconversion of D-galactose into d-tagatose. Enzym. Microb. Technol. 15, 105-108 (1993).
Cheng, L., et al. Thermostable L-arabinose isomerase from Bacillus stearothermophilus IAM 11001 for D-tagatose production: gene cloning, purification and characterisation. J. Sci. Food Agric. 90, 1327-1333 (2010).
Choi, J. M. et al. Structure of the thermophilic L-arabinose isomerase from Geobacillus kaustophilus reveals metal-mediated intersubunit interactions for activity and thermostability. Arch. Biochem. Biophys. 596, 51-62 (2016).
Chouayekh, H., et al. "Characterization of an L-arabinose isomerase from the Lactobacillus plantarum NC8 strain showing pronounced stability at acidic pH." FEMS microbiology letters 277.2 (2007): 260-267.

(Continued)

*Primary Examiner* — Iqbal H Chowdhury
(74) *Attorney, Agent, or Firm* — QUARLES & BRADY LLP

(57) ABSTRACT

Disclosed are components and methods for preparing tagatose from galactose via isomerization reactions using engineered components. The engineered components include microbial cells and methods for preparing microbial cells that have been engineered to catalyze isomerization of galactose to tagatose, in which the microbial cells express cytoplasmically an exogenous L-arabinose isomerase enzyme. The disclosed microbial cells may further be modified for use in methods for preparing tagatose from galactose via isomerization reactions where the microbial cells are treated with reagents that permeabilize the cells. The disclosed methods enable isomerization reactions of galactose to tagatose at relatively high rates, high conversions, and elevated temperatures.

20 Claims, 29 Drawing Sheets

Figure 1A:
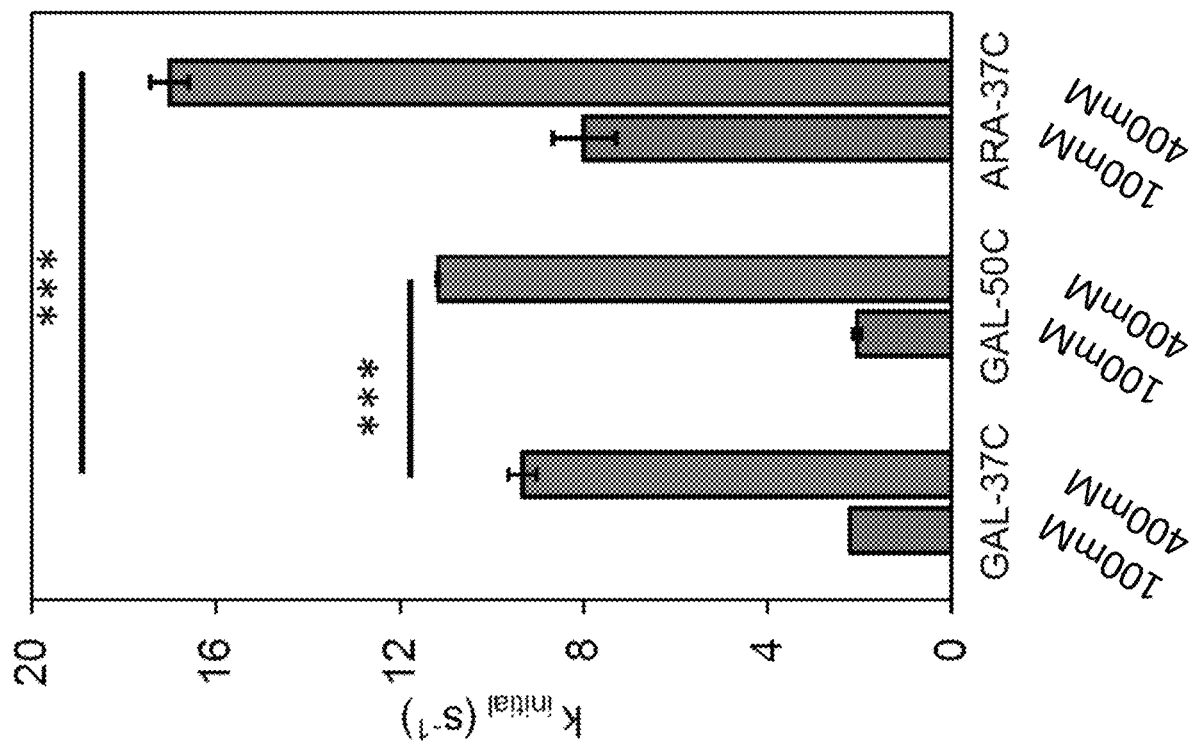

Specification includes a Sequence Listing.

(56) References Cited

OTHER PUBLICATIONS

Dische, Z. et al. A new spectrophotometric method for the detection and determination of keto sugars and trioses. Chem, J Biol 192, 583-587 (1951).

Fan, C. et al. Engineering of Alicyclobacillus hesperidum L-arabinose isomerase for improved catalytic activity and reduced pH optimum using random and site-directed mutagenesis. Appl. Biochem. Biotechnol. 177, 1480-1492 (2015).

Guo, Q. et al. Enhanced D-tagatose production by spore surface-displayed l-arabinose isomerase from isolated Lactobacillus brevis PC16 and biotransformation. Bioresour. Technol. 247, 940-946 (2018).

Hong, Y. H. et al. Production of D-tagatose at high temperatures using immobilized *Escherichia coli* cells expressing L-arabinose isomerase from Thermotoga neapolitana. Biotechnol. Lett. 29, 569-574 (2007).

Jayamuthunagai, J., et al. d-Tagatose production by permeabilized and immobilized Lactobacillus plantarum using whey permeate. Bioresour. Technol. 235, 250-255 (2017).

Jeong, D. W., et al. "Trienzymatic complex system for isomerization of agar-derived D-galactose into D-tagatose as a low-calorie sweetener." Journal of agricultural and food chemistry 68.10 (2020): 3195-3202.

Kim, H. J. et al. Purification and characterization of an L-arabinose isomerase from an isolated strain of Geobacillus thermodenitrificans producing D-tagatose. J. Biotechnol. 120, 162-173 (2005).

Kim, J. H. et al. Differential selectivity of the *Escherichia coli* cell membrane shifts the equilibrium for the enzyme-catalyzed isomerization of galactose to tagatose. Appl. Environ. Microbiol. 74, 2307-2313 (2008).

Kim, P., et al. High production of D-tagatose, a potential sugar substitute, using immobilized L-arabinose isomerase. Biotechnol. Prog. 17, 208-210 (2001).

Kim, B. J., et al. Characterization of a F280N variant of l-arabinose isomerase from Geobacillus thermodenitrificans identified as a d-galactose isomerase. Appl. Microbiol. Biotechnol. 9271-9281 (2014).

Kwon, S. Y. et al. Effects of temperature, pH, organic acids, and sulfites on tagatose browning in solutions during processing and storage. Food Sci. Biotechnol. 23, 677-684 (2014).

Li, Y., et al. Identification and characterization of a novel L-arabinose isomerase from Anoxybacillus flavithermus useful in D-tagatose production. Extremophiles 15, 441-450 (2011).

Liu, Y. et al. Efficient production of D-tagatose using a food-grade surface display system. J. Agric. Food Chem. 62, 6756-62 (2014).

Luecke, K. J. et al. Thermal stability of tagatose in solution. J. Food Sci. 75, C346-51 (2010).

Mei, W., et al. Characterization of an L-arabinose isomerase from Bacillus coagulans NL01 and its application for D-tagatose production. BMC Biotechnol. 16, 1-11 (2016).

Miskovic, L. et al. A design-build-test cycle using modeling and experiments reveals interdependencies between upper glycolysis and xylose uptake in recombinant S. cerevisiae and improves predictive capabilities of large-scale kinetic models. Biotechnol. Biofuels 10, 166 (2017).

Nguyen, T.-K., et al. Biochemical properties of L-arabinose isomerase from Clostridium hylemonae to produce D-tagatose as a functional sweetener. PLoS One 13, e0196099 (2018).

Oh, H. J., et al. Increase in D-tagatose production rate by site-directed mutagenesis of L-arabinose isomerase from Geobacillus thermodenitrificans. Biotechnol. Lett. 28, 145-149 (2006).

Pontes, D. et al. Immune response elicited by DNA vaccination using Lactococcus lactis is modified by the production of surface exposed pathogenic protein. PLoS One 9, e84509 (2014).

Prabhu, P., et al. Probing the molecular determinant for the catalytic efficiency of L-arabinose isomerase from Bacillus licheniformis. Appl. Environ. Microbiol. 76, 1653-1660 (2010).

Reider Apel, A. et al. Evolved hexose transporter enhances xylose uptake and glucose/xylose co-utilization in *Saccharomyces cerevisiae*. Sci. Rep. 6, 19512 (2016).

Rhimi, M. et al. Rational design of Bacillus stearothermophilus US100 l-arabinose isomerase: Potential applications for D-tagatose production. Biochimie 91, 650-653 (2009).

Rhimi, M. et al. The acid tolerant l-arabinose isomerase from the food grade Lactobacillus sakei 23K is an attractive d-tagatose producer. Bioresour. Technol. 101, 9171-9177 (2010).

Rhimi, M. et al. The secreted l-arabinose isomerase displays anti-hyperglycemic effects in mice. Microb. Cell Fact. 14, 204 (2015).

Salonen, N., et al. D-Tagatose production in the presence of borate by resting Lactococcus lactis cells harboring Bifidobacterium longum L-arabinose isomerase. Bioprocess Biosyst. Eng. 36, 489-497 (2013).

Schuurmann, J.; et al. Bacterial whole-cell biocatalysts by surface display of enzymes: toward industrial application. Applied Microbiology and Biotechnology 2014, 98, 8031-8046.

Waltman, M. J., et al. Engineering acidic Streptomyces rubiginosus D-xylose isomerase by rational enzyme design. Protein Eng. Des. Sel. 27, 59-64 (2014).

Ku, W. et al. L-arabinose isomerases: Characteristics, modification, and application. Trends Food Sci. Technol. 78, 25-33 (2018).

Xu, Z. et al. L-Arabinose isomerase and its use for biotechnological production of rare sugars. Appl. Microbiol. Biotechnol. 98, 8869-8878 (2014).

Xu, Z. et al. Production of D-tagatose, a functional sweetener, utilizing alginate immobilized Lactobacillus fermentum CGMCC2921 cells. Appl. Biochem. Biotechnol. 166, 961-73 (2012).

Xu, Z. et al. A novel l-arabinose isomerase from Lactobacillus fermentum CGMCC2921 for d-tagatose production: Gene cloning, purification and characterization. J. Mol. Catal. B Enzym. 70, 1-7 (2011).

Zhang, W. et al. Characterization of a novel metal-dependent D-psicose 3-epimerase from Clostridium scindens 35704. PLoS. One. 8, 62987 (2013).

Zhang, Y. W., et al. Enhanced activity and stability of l-arabinose isomerase by immobilization on aminopropyl glass. Appl. Microbiol. Biotechnol. 89, 1435-1442 (2011).

Zheng, Z., et al. Rational design of Bacillus coagulans NL01 L-arabinose isomerase and use of its F279I variant in d-tagatose production. J. Agric. Food Chem. 65, 4715-4721 (2017).

Zhu, Y.; et al. Overexpression and characterization of a thermostable ß-agarase producing neoagarotetraose from a marine isolate *Microbulbifer* sp. AG1. Acta Oceanologica Sinica 2019, 38, 96-106.

\* cited by examiner

SEQUENCE LISTING

<160> NUMBER OF SEQ ID NOS: 1

<210> SEQ ID NO 1
<211> LENGTH: 474
<212> TYPE: PRT
<213> ORGANISM: Lactobacillus sakei

<400> SEQUENCE: 1

```
Met Leu Asn Thr Glu Asn Tyr Glu Phe Trp Phe Val Thr Gly Ser Gln
1               5                  10                  15

Ser Leu Tyr Gly Glu Glu Thr Leu Arg Ser Val Glu Lys Asp Ala Lys
            20                  25                  30

Glu Ile Val Glu Lys Leu Asn Ala Ser His Gln Leu Pro Tyr Pro Ile
        35                  40                  45

Val Phe Lys Leu Val Ala Thr Thr Ala Asp Asn Ile Thr Lys Val Met
    50                  55                  60

Lys Glu Ala Asn Tyr Asn Asp His Val Ala Gly Val Ile Thr Trp Met
65                  70                  75                  80

His Thr Phe Ser Pro Ala Lys Asn Trp Ile Arg Gly Thr Lys Leu Leu
                85                  90                  95

Gln Lys Pro Leu Leu His Leu Ala Thr Gln Phe Leu Asn Lys Ile Pro
            100                 105                 110

Tyr Asp Thr Ile Asp Phe Asp Tyr Met Asn Leu Asn Gln Ser Ala His
        115                 120                 125

Gly Asp Arg Glu Tyr Ala Phe Ile Asn Ala Arg Leu Arg Lys Asn Asn
    130                 135                 140

Lys Ile Ile Ser Gly Tyr Trp Gly Asp Glu Asp Val Gln Lys Ala Met
145                 150                 155                 160

Ala Lys Trp Met Asp Val Ala Val Ala Tyr Asn Glu Ser Phe Lys Ile
                165                 170                 175

Lys Val Val Thr Phe Ala Asp Lys Met Arg Asn Val Ala Val Thr Asp
            180                 185                 190

Gly Asp Lys Val Glu Ala Gln Ile Lys Phe Gly Trp Thr Val Asp Tyr
        195                 200                 205

Trp Gly Val Gly Asp Leu Val Ala Glu Val Asn Ala Val Ser Glu Ala
    210                 215                 220

Asp Ile Asp Ala Lys Tyr Ala Asp Leu Gln Lys Glu Tyr Asp Phe Val
225                 230                 235                 240

Glu Gly Gln Asn Thr Pro Glu Lys Phe Glu His Asn Val Lys Tyr Gln
                245                 250                 255

Ile Arg Glu Tyr Phe Gly Leu Lys Lys Phe Met Asp Asp Arg Gly Tyr
            260                 265                 270

Thr Ala Phe Thr Thr Asn Phe Glu Asp Leu Val Gly Leu Glu Gln Leu
        275                 280                 285

Pro Gly Leu Ala Ala Gln Leu Leu Met Ala Glu Gly Tyr Gly Phe Ala
    290                 295                 300

Gly Glu Gly Asp Trp Lys Thr Ala Leu Asp Arg Leu Leu Lys Ile
305                 310                 315                 320

Met Ala His Asn Glu Lys Thr Val Phe Met Glu Asp Tyr Thr Leu Asp
                325                 330                 335

Leu Arg Gln Gly His Glu Ala Ile Leu Gly Ser His Met Leu Glu Val
            340                 345                 350

Asp Pro Ser Ile Ala Ser Asp Lys Pro Arg Val Glu Val His Pro Leu
        355                 360                 365
```

-continued

```
Asp Ile Gly Asp Lys Asp Asp Pro Ala Arg Leu Val Phe Thr Gly Met
    370             375                 380

Gln Gly Asp Ala Val Asp Val Thr Met Ala Asp Tyr Gly Asp Glu Phe
385             390                 395                 400

Lys Leu Met Ser Tyr Asp Val Arg Gly Asn Lys Pro Glu Ala Asp Thr
            405                 410                 415

Pro His Leu Pro Val Ala Lys Gln Leu Trp Thr Pro Lys Gln Gly Leu
            420                 425             430

Arg Glu Gly Ala Val Gly Trp Leu Thr Val Gly Gly His His Thr
            435             440                 445

Val Leu Ser Phe Ala Val Asp Ser Glu Gln Leu Gln Asp Leu Ser His
    450             455                 460

Leu Phe Asp Leu Thr Tyr Val Asn Ile Lys
465             470
```

GALACTOSE TO TAGATOSE ISOMERIZATION AT MODERATE TEMPERATURES WITH HIGH CONVERSION AND PRODUCTIVITY

CROSS-REFERENCE TO RELATED PATENT APPLICATIONS

The present application claims the benefit of priority under 35 U.S.C. § 119(e) to U.S. Provisional Application No. 62/971,695, filed on Feb. 7, 2020, the content of which is incorporated herein by reference in its entirety.

STATEMENT REGARDING FEDERALLY SPONSORED RESEARCH OR DEVELOPMENT

This invention was made with government support under grants HD090444 and HD091798 awarded by the National Institutes of Health. The government has certain rights in the invention.

SEQUENCE LISTING

A Sequence Listing accompanies this application and is submitted as an ASCII text file of the sequence listing named "166118_01015_ST25.txt" which is 4 KB in size and was created on Mar. 22, 2021. The sequence listing is electronically submitted via EFS-Web with the application and is incorporated herein by reference in its entirety.

BACKGROUND

The present invention generally relates to components and methods for preparing saccharides. In particular, the present invention relates to components and methods for preparing tagatose from galactose via isomerization reactions using engineered cells.

D-Tagatose is a natural sugar that is of significant interest to the food industry due to desirable taste, nutrition, and chemical properties. Tagatose has been prepared from galactose by chemical synthesis. In one method of chemical synthesis, galactose is isomerized in the presence of inorganic salt, mediated by metal hydroxide as a catalyst, to form a metal hydroxide-tagatose complex as an intermediate. The intermediate then is neutralized by acid to produce tagatose. However, this method of chemical synthesis is very complicated in its process and inefficient and generates industrial wastes, even though it can be economical and provide tagatose with high yield.

Tagatose also may be prepared by enzyme-mediated conversion, in which galactose is converted to tagatose using the enzyme arabinose isomerase. However, enzymatic synthesis of tagatose is currently expensive and cost-prohibitive for large-scale use due to limitations such as low conversions, reaction rates, and enzyme stability. Here, the inventors disclose the use of *Lactobacillus sakei* L-arabinose isomerase (LsLAI) for isomerization of D-galactose to D-tagatose. After exploring several strategies to overcome low conversions, reaction rates, and enzyme stability, the inventors show that encapsulating LsLAI in gram-positive *Lactobacillus plantarum* that is chemically permeabilized enables reactions at high rates, high conversions, and elevated temperatures. In a batch process, this system enables 50% conversion in 4 h starting with 300 mM galactose (an average productivity of 38 mM/h), and 85% conversion in 48 h. This is a marked improvement compared to other published processed for tagatose synthesis.

SUMMARY

Disclosed are components and methods for preparing tagatose from galactose via isomerization reactions using engineered components. The engineered components include microbial cells and methods for preparing microbial cells that have been engineered to catalyze isomerization of galactose to tagatose. The engineered microbial cells that are disclosed herein may express cytoplasmically an exogenous L-arabinose isomerase enzyme. The disclosed microbial cells may be utilized in methods for preparing tagatose from galactose via isomerization reactions, and further, the disclosed microbial cells may be treated with reagents that permeabilize the cells in order to improve use of the disclosed microbial cells in methods for preparing tagatose from galactose via isomerization reactions. The disclosed microbial cells and methods may be utilized to perform isomerization reactions of galactose to tagatose having relatively high reaction rates and high conversion rates. In addition, the disclosed microbial cells and methods may be utilized to perform isomerization reactions of galactose to tagatose at elevated reaction temperatures.

Figure 1B:
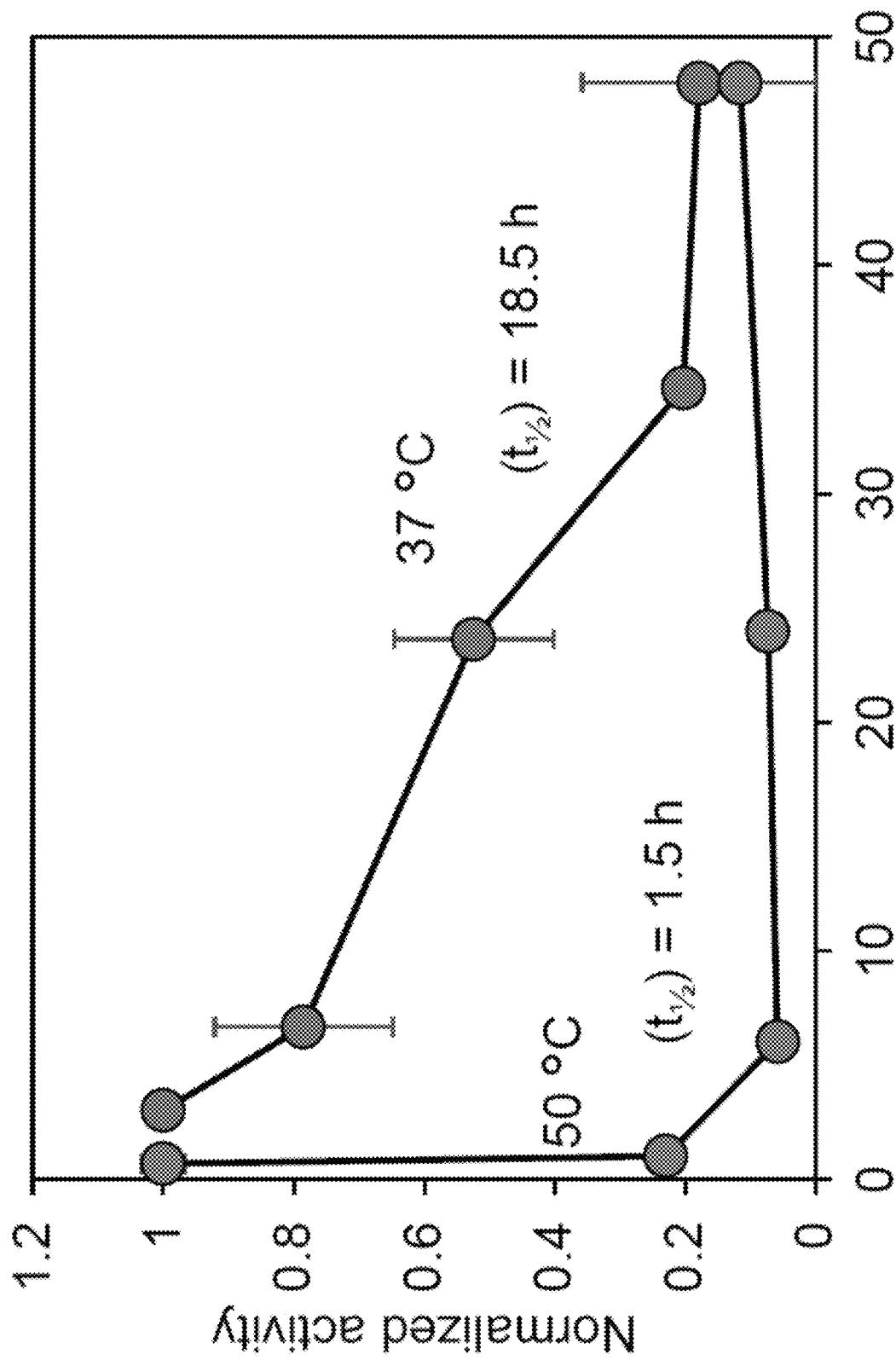
Figure 1C:
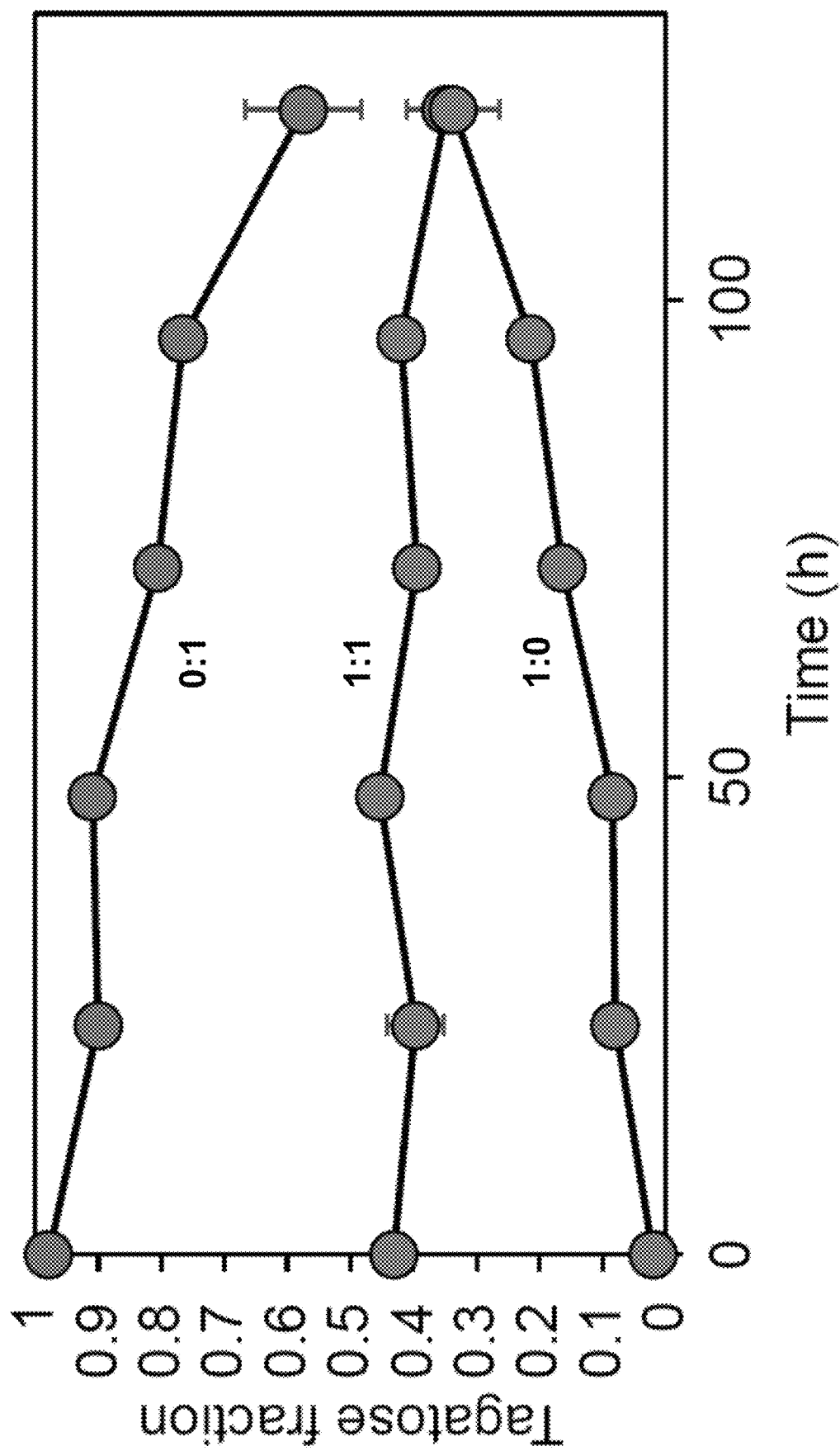

FIG. 1A, FIG. 1B, and FIG. 1C. Assessing the limitations of free-enzyme LsLAI. FIG. 1A) Initial turnover rates of purified LsLAI compared at medium (100 mM) and high (400 mM) substrate loading at low (37° C.) and high (50° C.) temperatures. Comparison of the non-native substrate, galactose at low (GAL-37C) and high (GAL-50C) temperature, to that of native substrate, arabinose at low temperature (ARA-37C). FIG. 1B) Loss of activity of purified LsLAI over time incubated at 37° C. or 50° C. Half-life calculated from first-order decay equation. FIG. 1C) Equilibrium conversion of purified LsLAI starting from 10 mM total substrate with galactose to tagatose ratio at 1:0 (10 mM galactose), 1:1 (5 mM each galactose and tagatose), or 0:1 (10 mM tagatose) incubated at 37° C. Additional enzyme was added every 24 h to account for thermal inactivation. The data are means from three independent biological replicates (n=3). ***=p<0.001 (Students t-test).

Figure 2A:
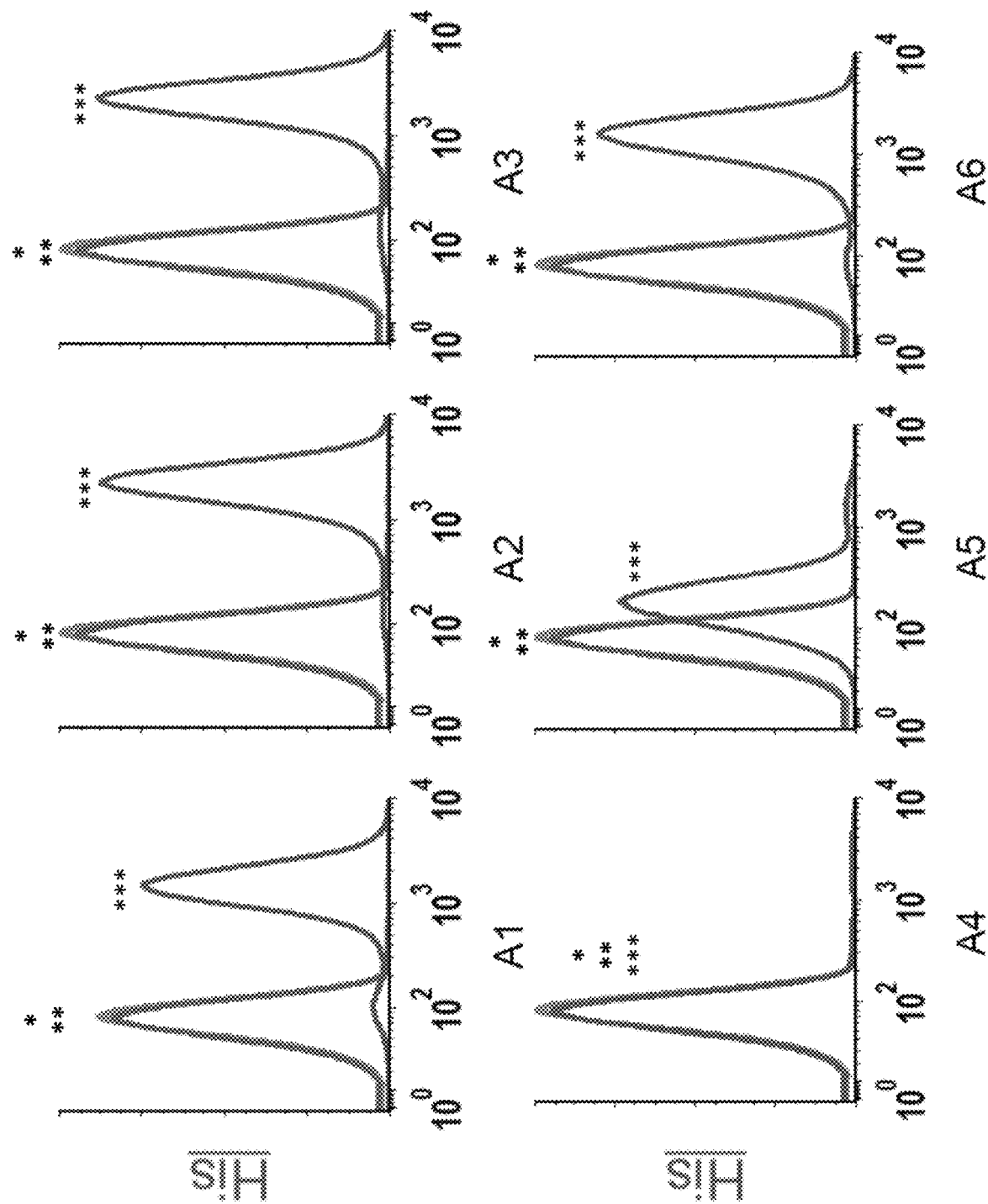
Figure 2B:
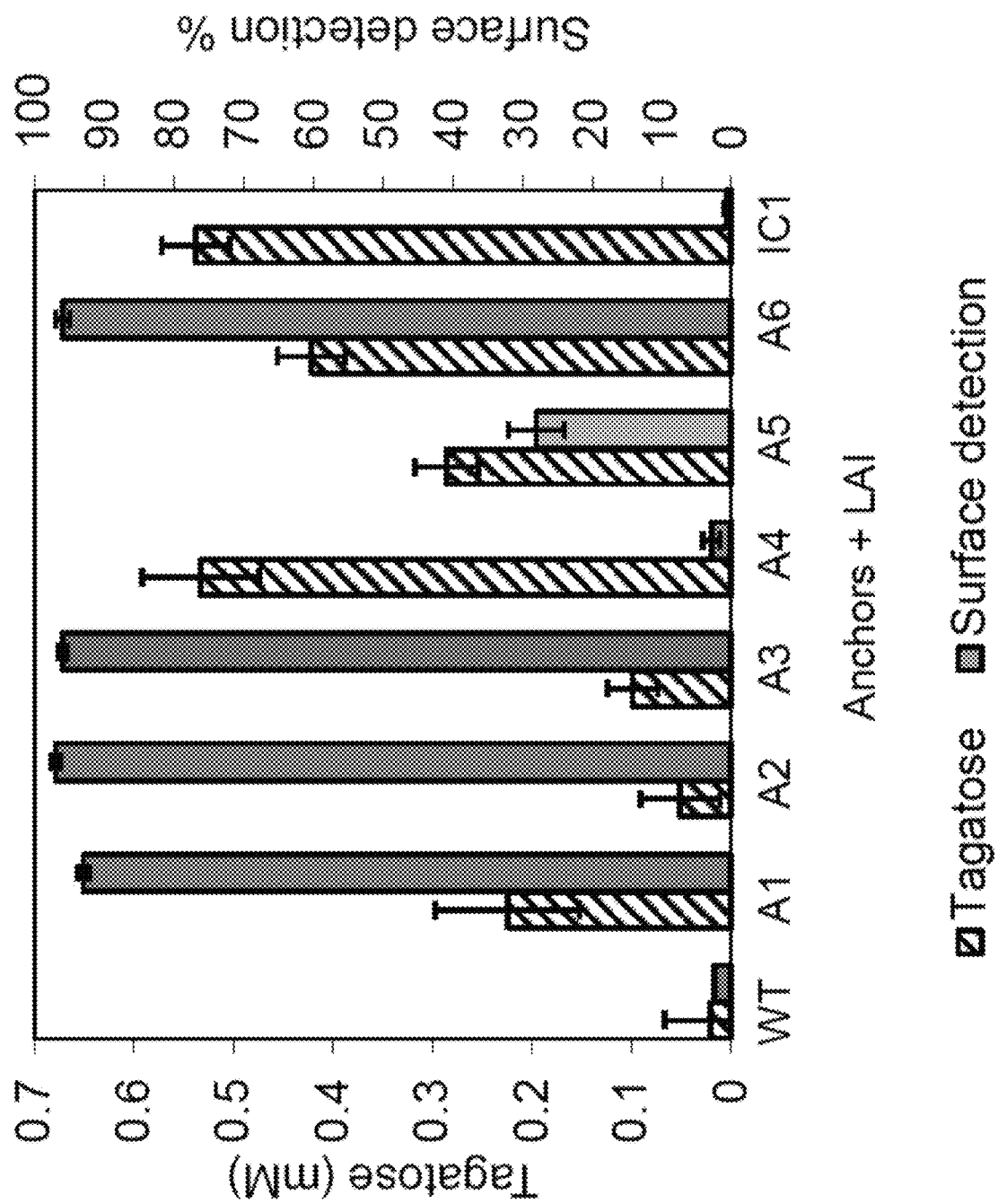
Figure 2C:
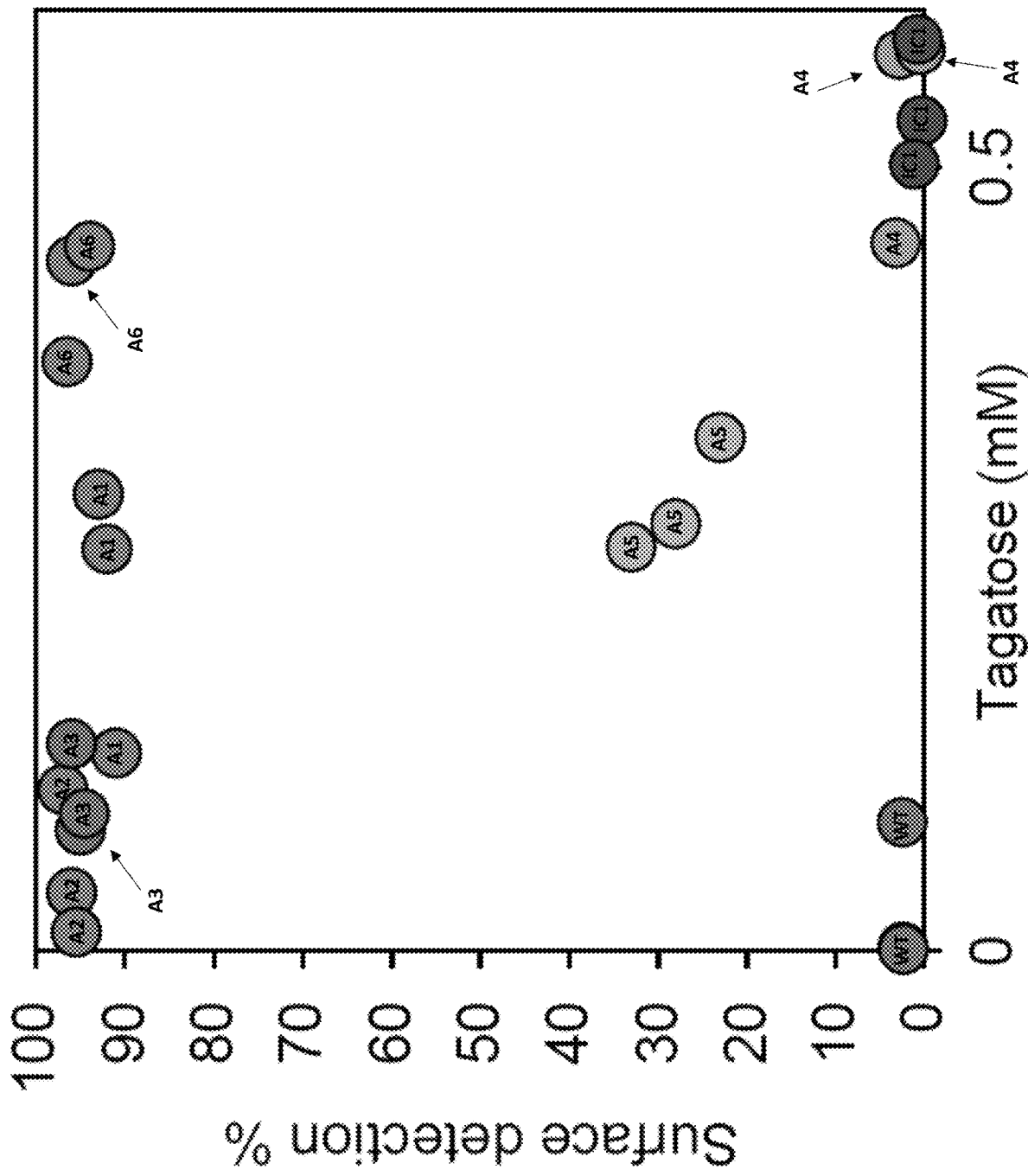

FIG. 2A, FIG. 2B, and FIG. 2C. LsLAI surface display and activity. FIG. 2A) Flow cytometry analysis of *L. plantarum* wild-type cells (*), cells expressing intracellular His6-tagged LsLAI (), or cells expressing LsLAI fused to native surface anchor proteins A1-A6 for display (*) with $10^5$ counts per sample. Data is normalized to number of counts. FIG. 2B) Comparing the amount of tagatose produced from 200 mM galactose in 2 h (hashed) with the positive percentage of the population with surface detection intensity above that of wild-type (WT) for intracellularly expressed IC1 or anchor protein A1-A6 (colored) based on negative gate. FIG. 2C) Scatterplot of each replicate measurement correlating surface detection vs. tagatose produced. There is no significant correlation between the display level and activity based on Pearson Product Moment Correlation test (Correlation coefficient=−0.395, p=0.0564). The data are means from three biological replicates.

Figure 3A:
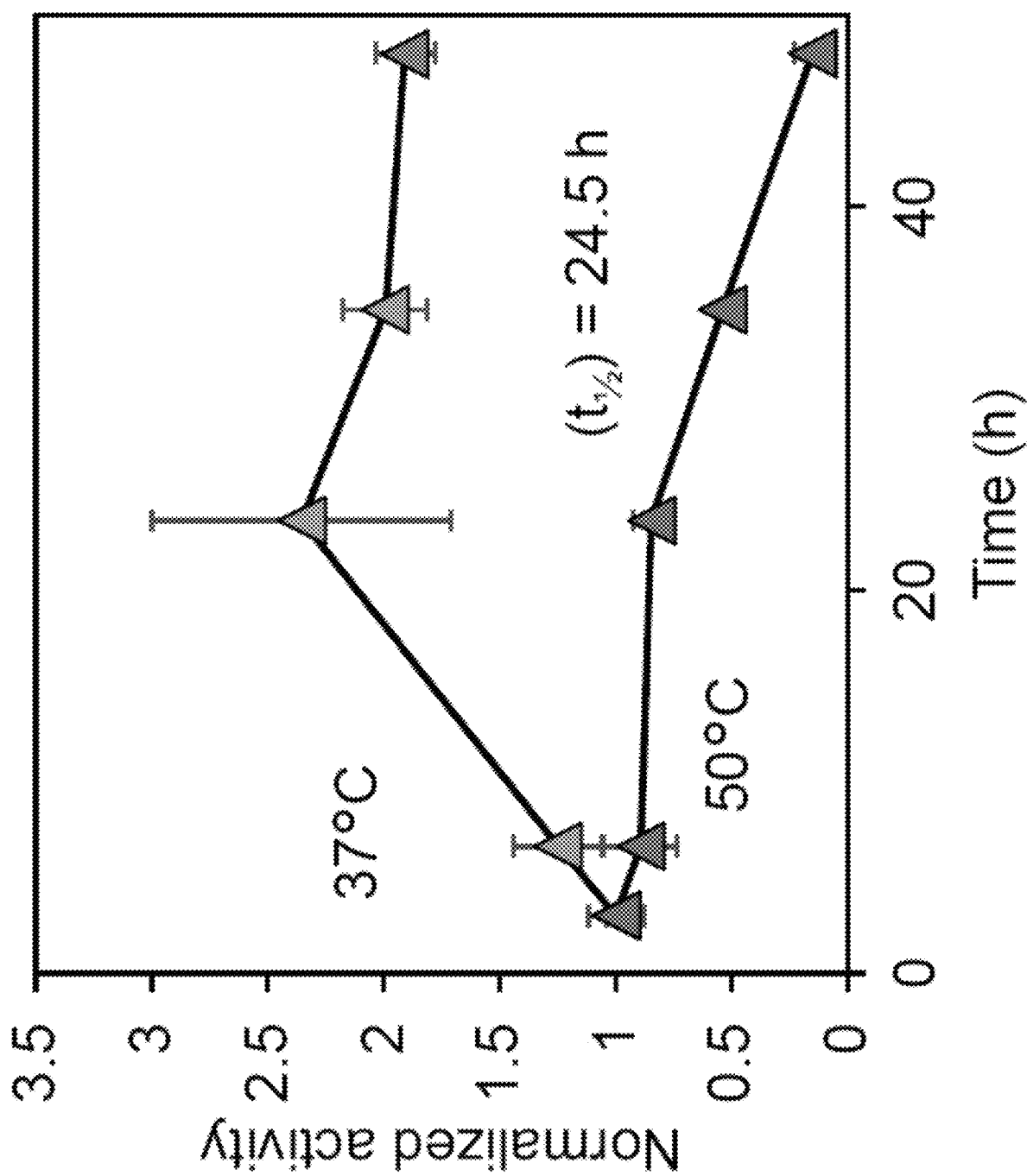
Figure 3B:
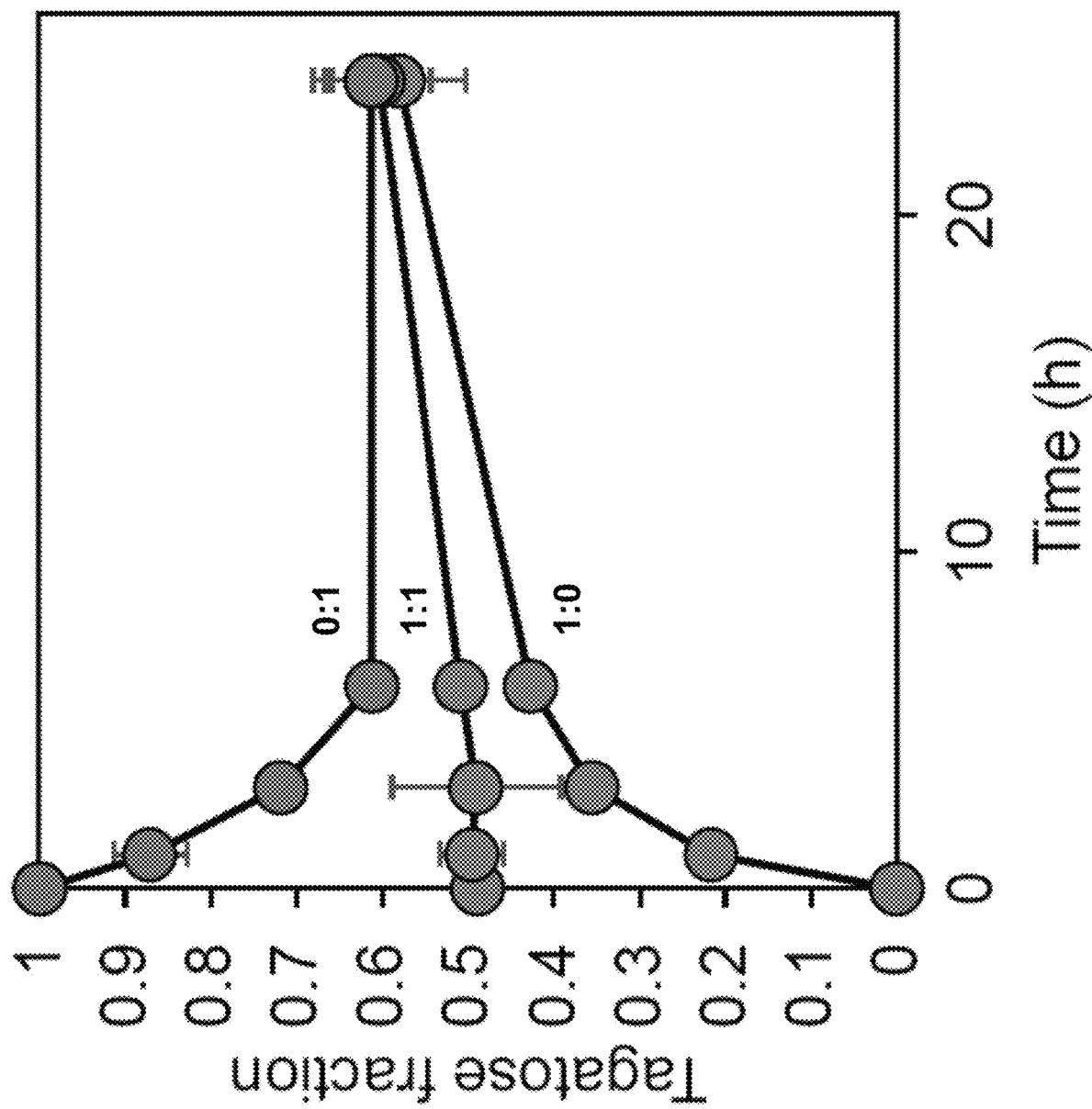
Figure 3C:
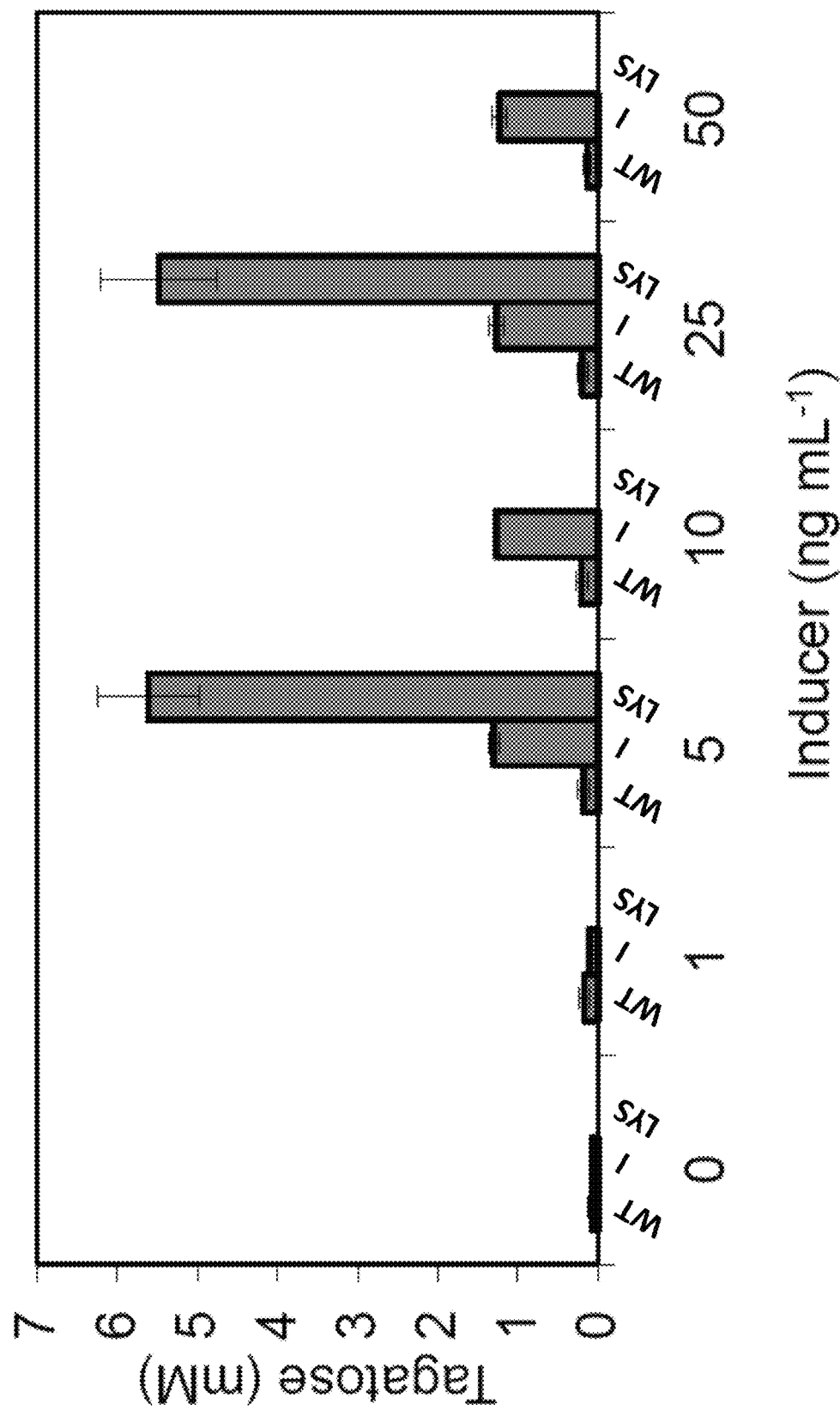

FIG. 3A, FIG. 3B, and FIG. 3C. Encapsulation of LsLAI improves equilibrium conversion and provides thermal stability. FIG. 3A) Loss of activity of encapsulated LsLAI (IC2) over time incubated in PBSM pH 7.4 at 37° C. or 50° C. Half-life calculated assuming first-order decay. FIG. 3B) Equilibrium conversion of encapsulated LsLAI starting from 30 mM total substrate: 1:0 (30 mM galactose), 1:1 (15 mM each), or 0:1 (30 mM tagatose) galactose:tagatose respectively. FIG. 3C) Tagatose production from 200 mM galactose of *L. plantarum* wild type (WT) cells, IC2 cells expressing LsLAI intracellularly (I), or crude lysate of the same IC2 cells expressing LsLAI cytoplasmically (LYS) at different induction concentrations. The data are means from three biological replicates.

Figure 4:
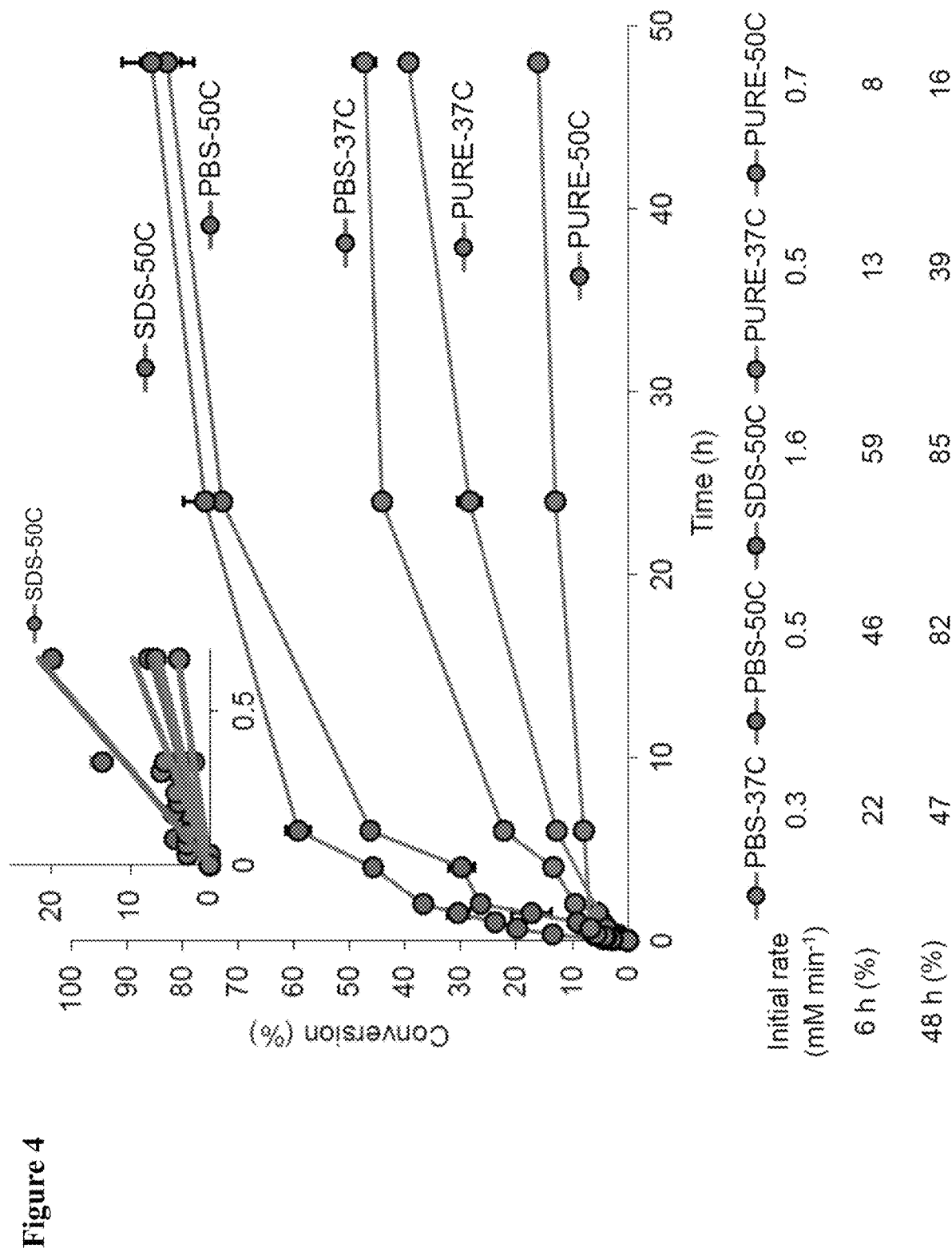

FIG. 4. Modified encapsulation of LsLAI maximizes tagatose production. Batch tagatose production over time starting from 300 mM galactose. Encapsulated LsLAI (IC2) was tested for tagatose production as unmodified (PBS) or SDS permeabilized (SDS) compared to purified enzyme at 37° C. or 50° C. to demonstrate its advantages. Encapsulated LsLAI is PBS-37C, encapsulated LsLAI at 50° C. is PBS-50C (pink), permeabilized encapsulated LsLAI at 50° C. is SDS-50C (blue), purified free-enzyme LsLAI at 37° C. is PURE-37C, and purified free-enzyme LsLAI at 50° C. is PURE-50C. Inset plot shows 0-1 h data to highlight initial reaction rates of each catalyst for comparison purposes. Salient features are summarized in table. The data are means from three biological replicates.

Figure 5A:
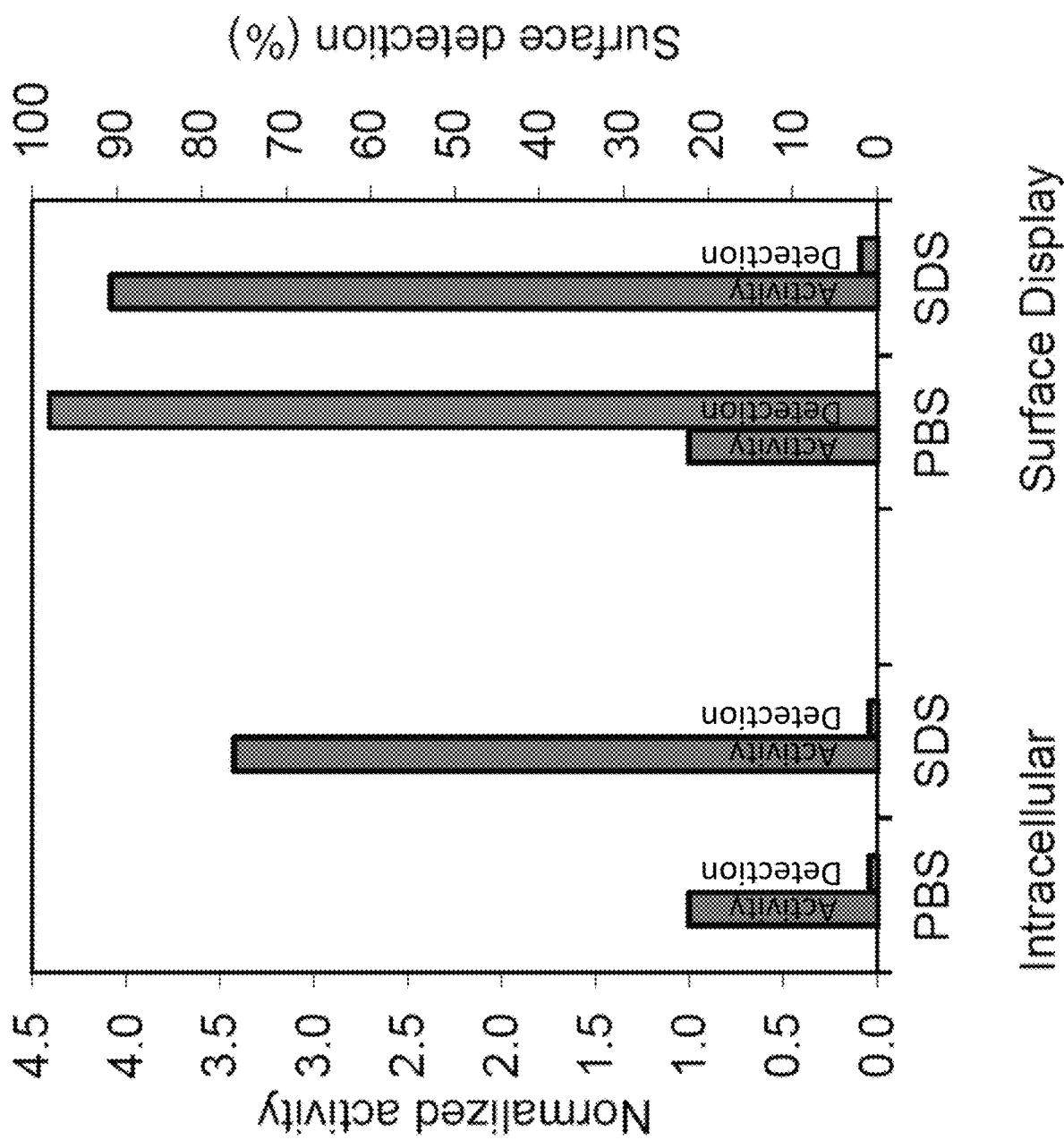
Figure 5B:
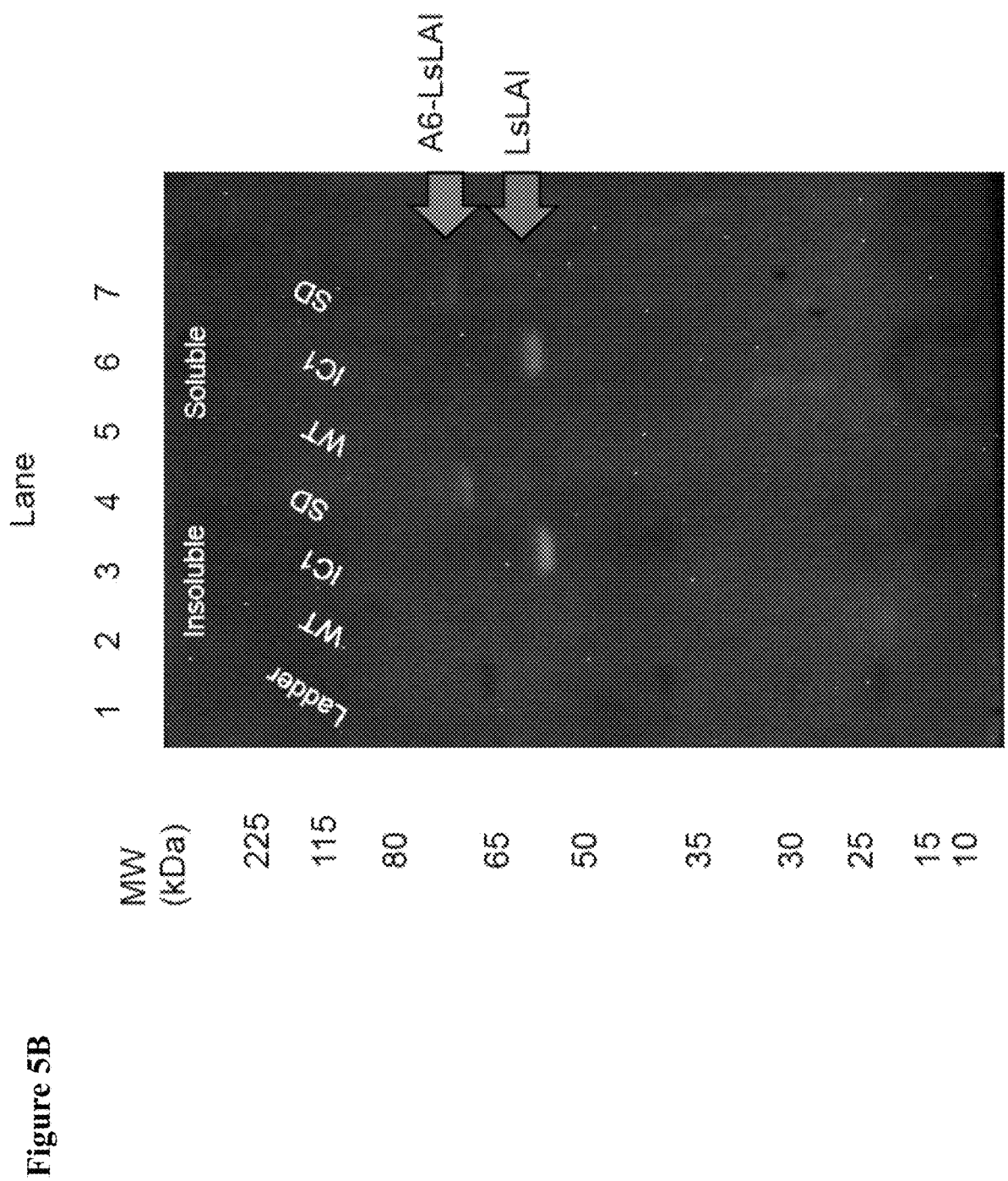

FIG. 5A and FIG. 5B. Surface treatment of *L. plantarum* surface displayed LsLAI. FIG. 5A) Comparison of the activity and surface detection percentage of *L. plantarum* expressing LsLAI containing a His6-tag either intracellularly (left) or surface displayed with anchor protein A6 (right). Activity of cells treated with 0.05% SDS normalized to untreated cells (PBS). FIG. 5B) Western blot analysis of insoluble (lanes 2-4) or soluble protein fraction (lanes 5-6) of *L. plantarum* wild-type "WT" (lanes 2, 5) or expressing LsLAI intracellularly "IC1" (lanes 3, 6) or expressing A6-LsLAI surface displayed "SD" (lanes 4, 7). Expected molecular weight (MW) of LsLAI and A6-LsLAI is 54 kDa and 76.5 kDa, respectively.

Figure 6A:
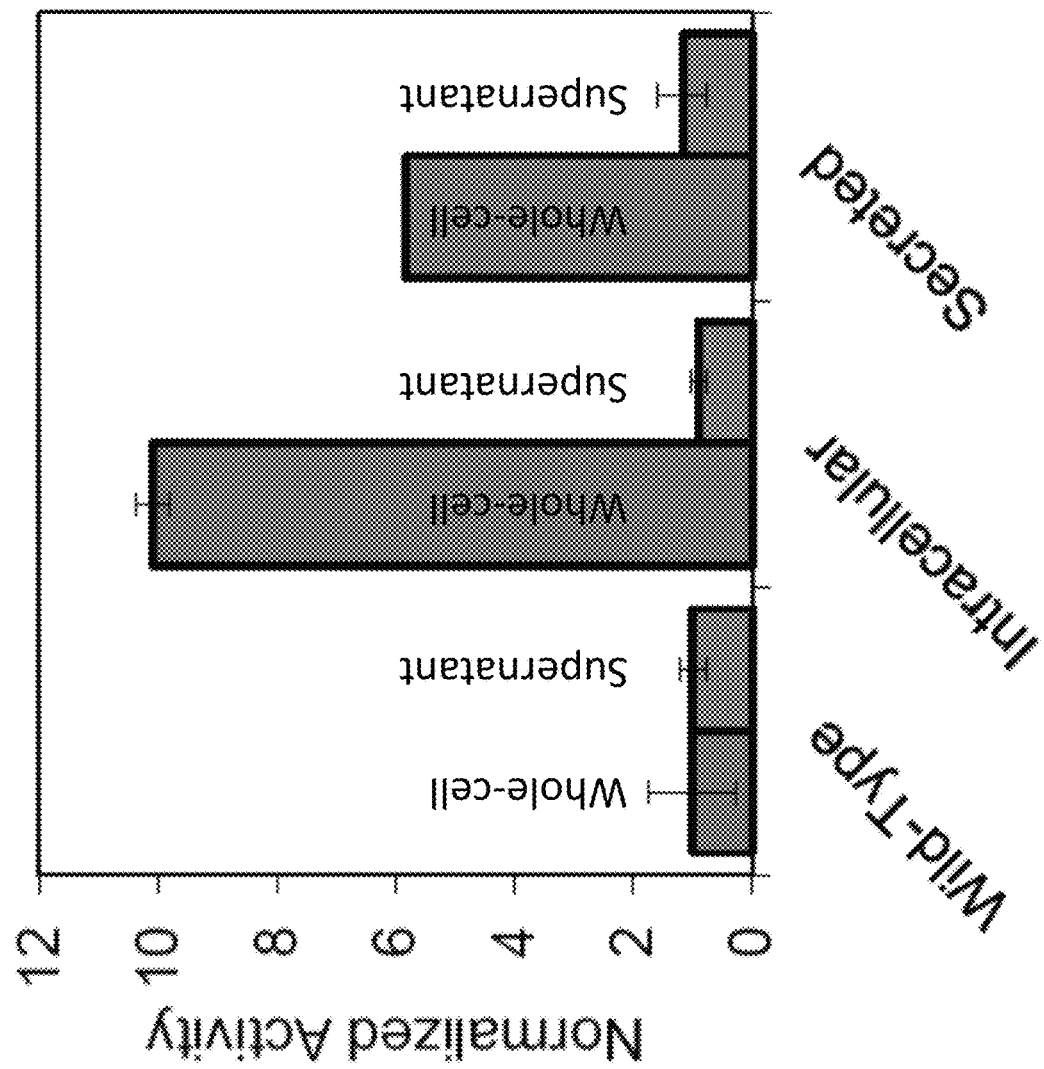
Figure 6B:
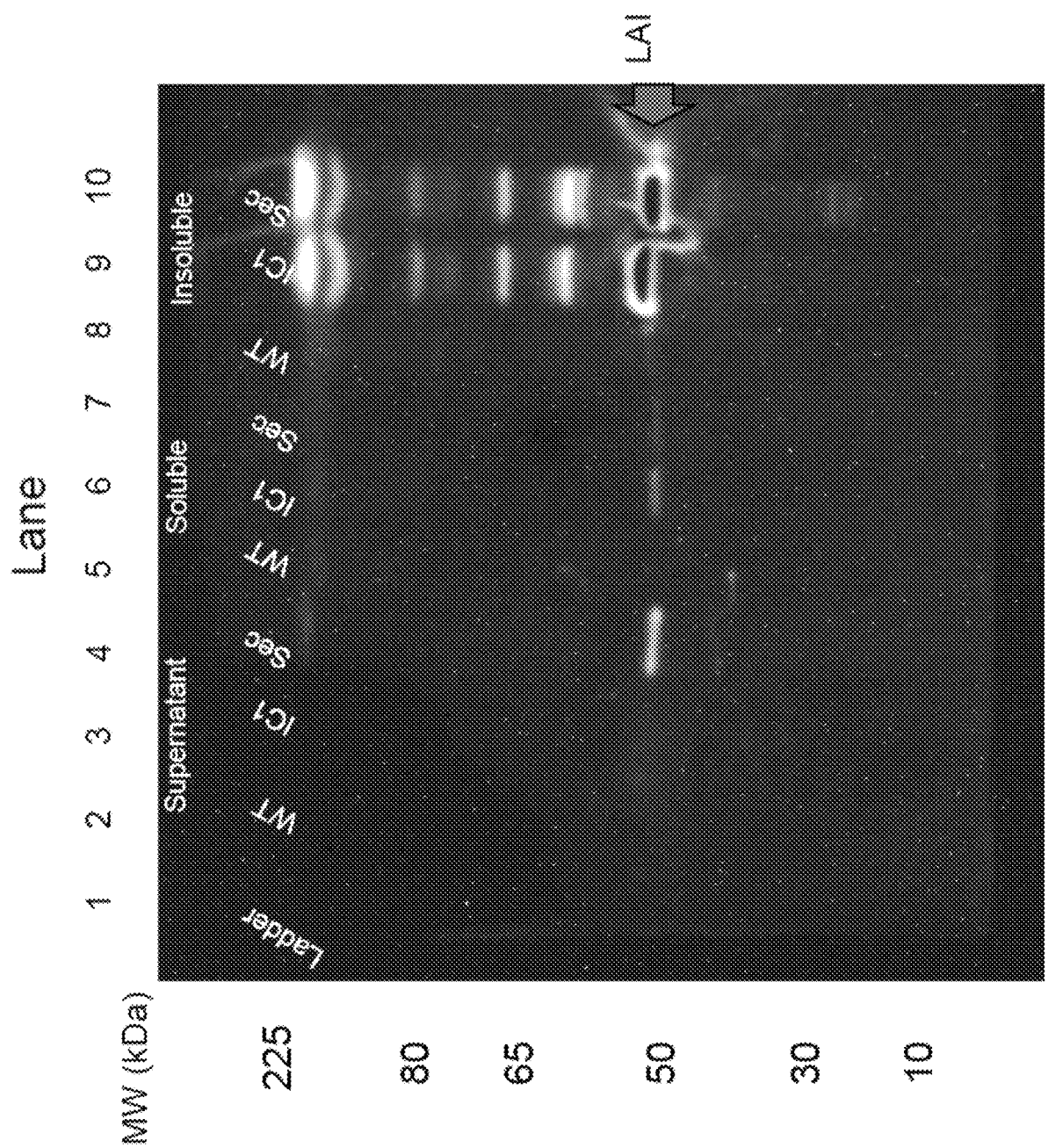

FIG. 6A and FIG. 6B. *L. plantarum* secreted LsLAI is inactive. FIG. 6A) Comparison of the whole-cell and supernatant of *L. plantarum* wild-type (left) or expressing LsLAI containing a His6-tag either intracellularly or as secreted/unanchored protein. The data are means from three biological replicates. FIG. 6B) Western blot analysis of culture supernatant (lanes 2-4) or soluble (lanes 5-7) and insoluble (lanes 8-10) protein fractions of *L. plantarum* cells. Shown are wild-type "WT" control cells (lanes 2, 5, 8), cells expressing LsLAI intracellularly "I" (lanes 3, 6, 9), and cells secreting LsLAI "Sec" (lanes 4, 7, 10). Supernatant was concentrated 20× before analysis. Expected molecular weight (MW) of LsLAI and secreted LsLAI is 54 kDa.

Figure 7:
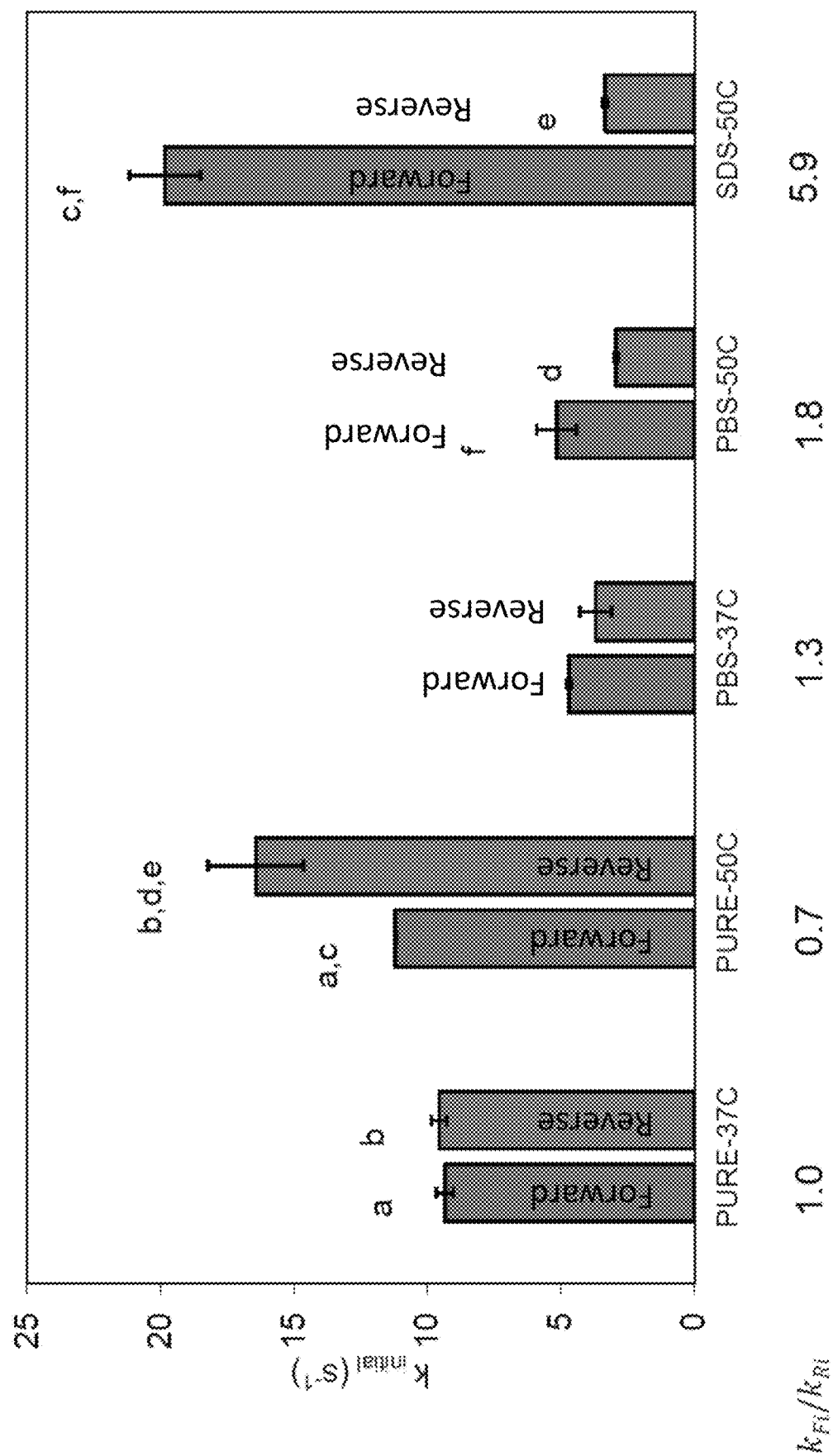

FIG. 7. Initial turnover rates. Initial turnover rates of purified free-enzyme, (PURE), *L. plantarum*-encapsulated (PBS), and permeabilized *L. plantarum* encapsulated (SDS) LsLAI in forward (galactose as substrate) and reverse (tagatose as substrate) direction in the presence of 400 mM substrate at 37 or 50° C. Ratio of forward to reverse reaction rate is denoted by $k_F/k_R$. The data are means from three independent biological replicates (n=3). (Significance between samples tested via ANOVA analysis using Sigma-Plot 13.0. a,c,d,e=p<0.001, b=p<0.05)

Figure 8:
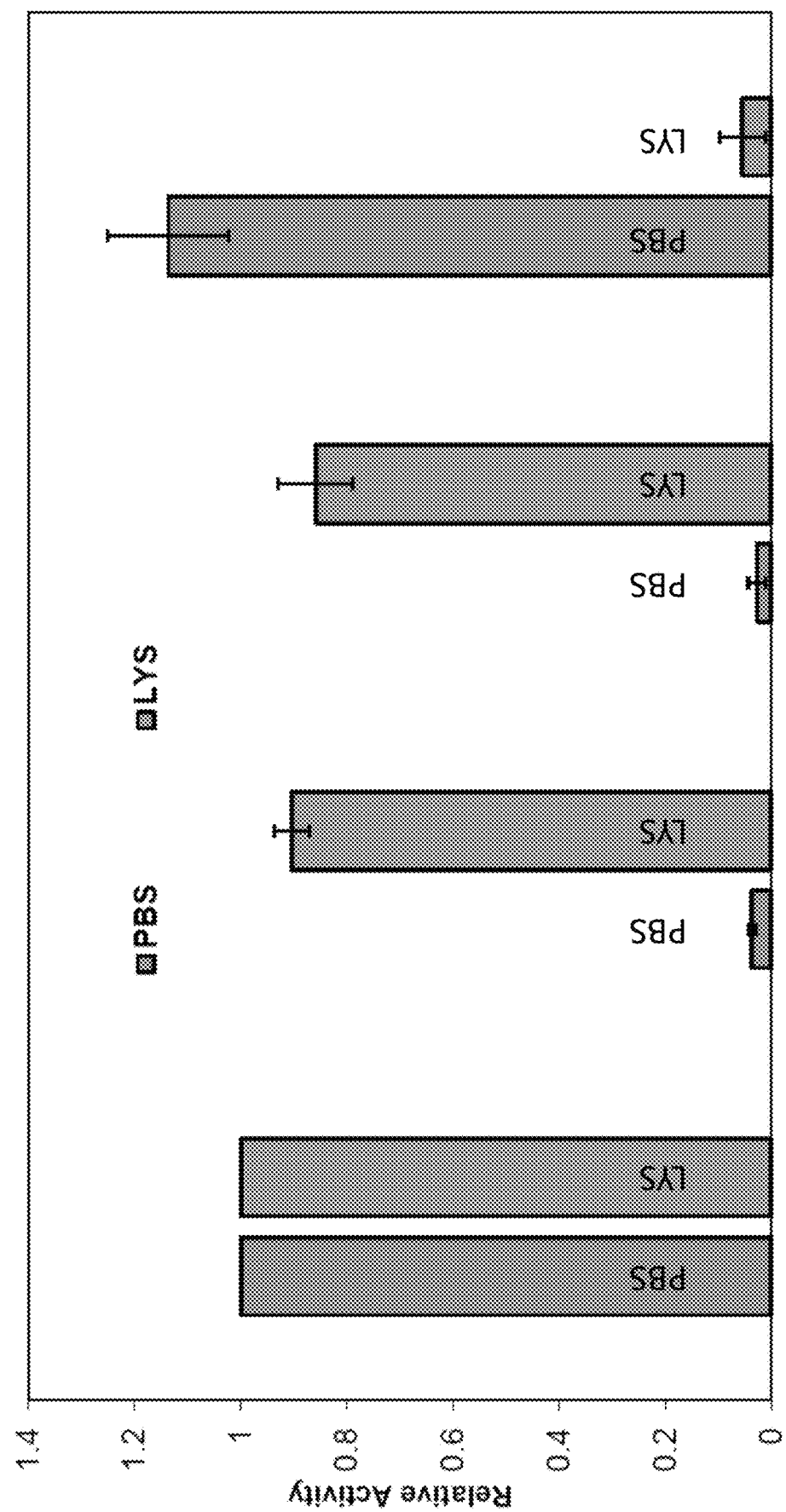

FIG. 8. Selective nature of cellular encapsulating LsLAI. Tagatose production of unmodified IC2 cells expressing LsLAI (PBS) or cell lysate (LYS) in the presence of different combinations of galactose (gal), dextrose (dex), and/or arabinose (ara) after 20 min incubation at 37° C. Activity normalized to 30 mM galactose condition for unmodified whole-cells (PBS) and cell lysate (LYS) independently.

Figure 9A:
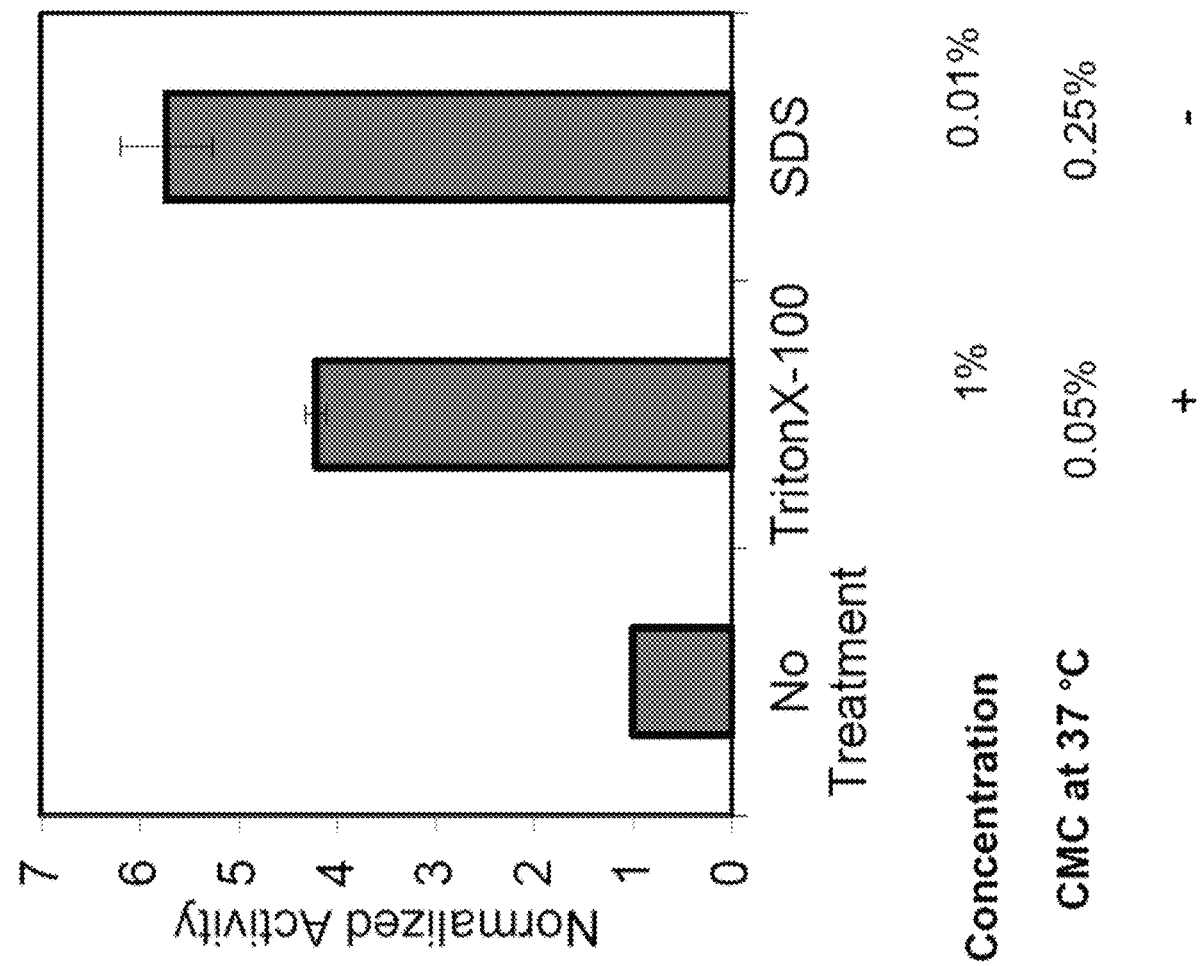
Figure 9B:
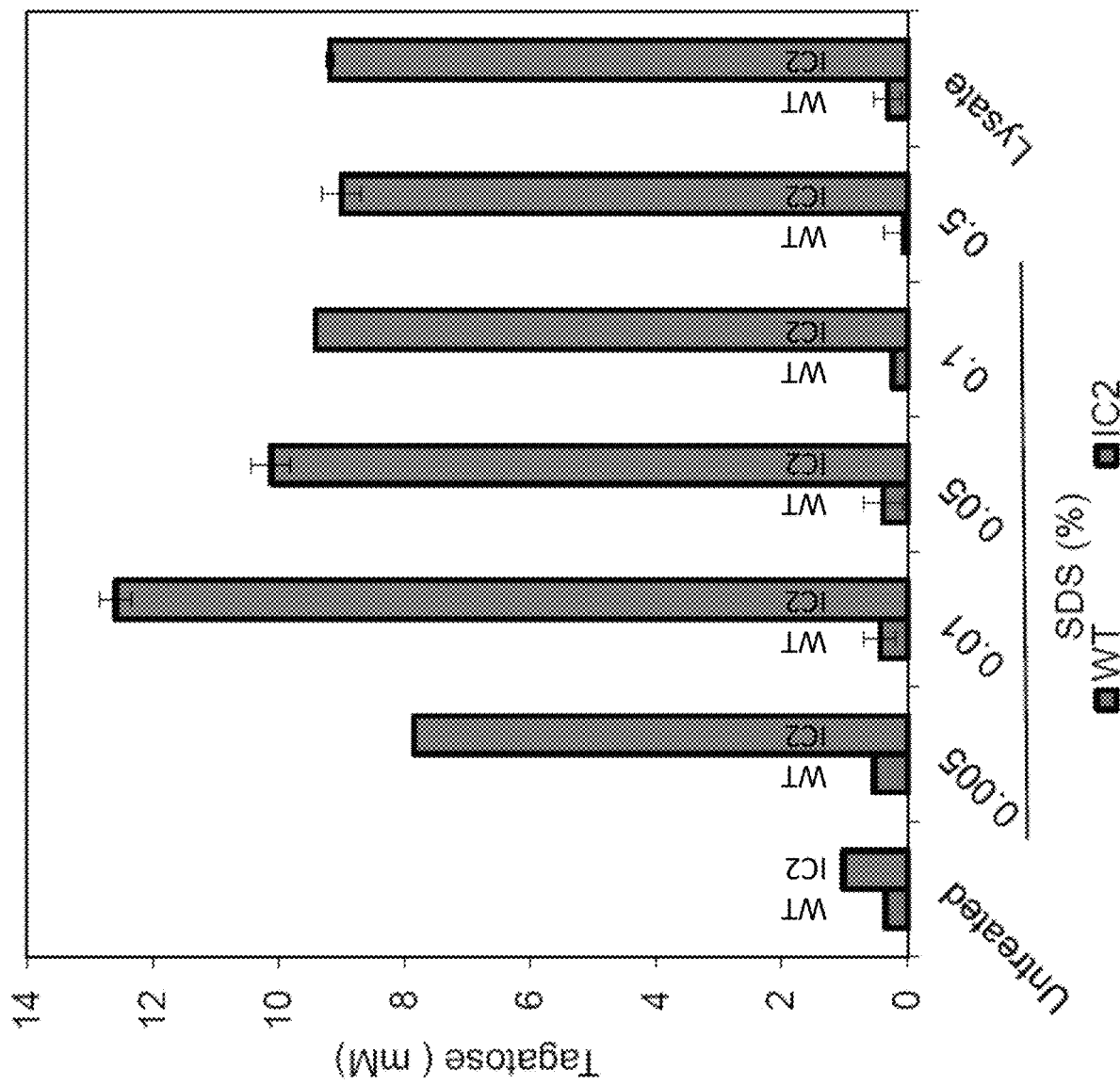

FIG. 9A and FIG. 9B. SDS permeabilization of encapsulated LsLAI overcomes kinetic penalty. A) Comparison of activity of encapsulated LsLAI having undergone permeabilization by 1% TritonX-100 (middle) or 0.01% SDS (right) normalized to untreated cells "No Treatment" (left). B) Optimization of SDS permeabilization of *L. plantarum* wild type "WT" or expressing LsLAI intracellularly "IC2" that produced the greatest amount of tagatose at 37° C. in 2 h as compared to untreated cells or crude lysate. The data are means from three biological replicates.

Figure 10:
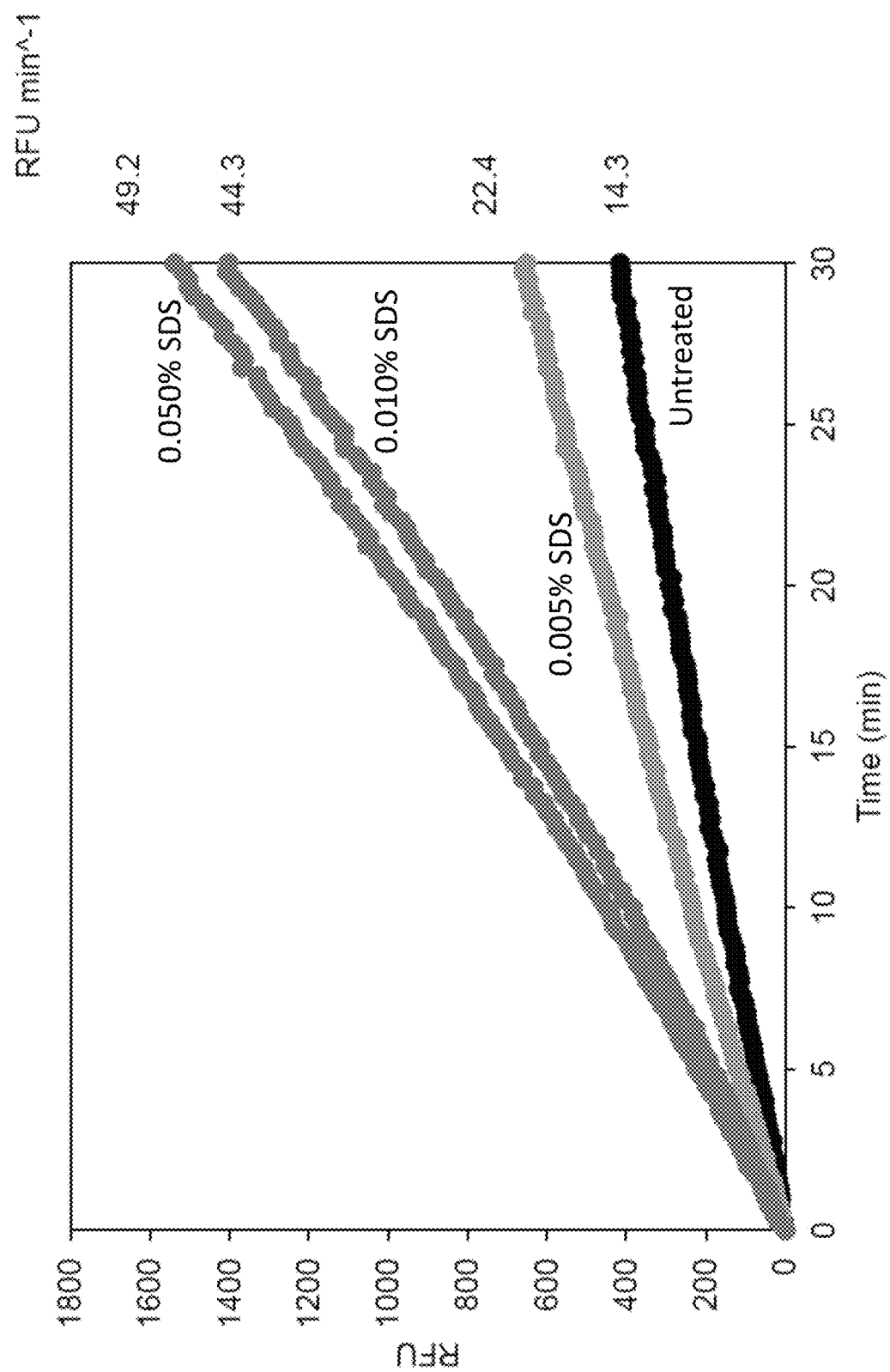

FIG. 10. SDS permeabilization increases transport. Continuously monitoring the production of fluorescent signal from reporter cFDA after activation upon transport using *L. plantarum* wild-type untreated or after SDS permeabilization with 0.005% SDS, 0.01% SDS, or 0.05 SDS. Relative fluorescence units (RFU) generated per minute is a proxy for transport kinetics.

Figure 11:
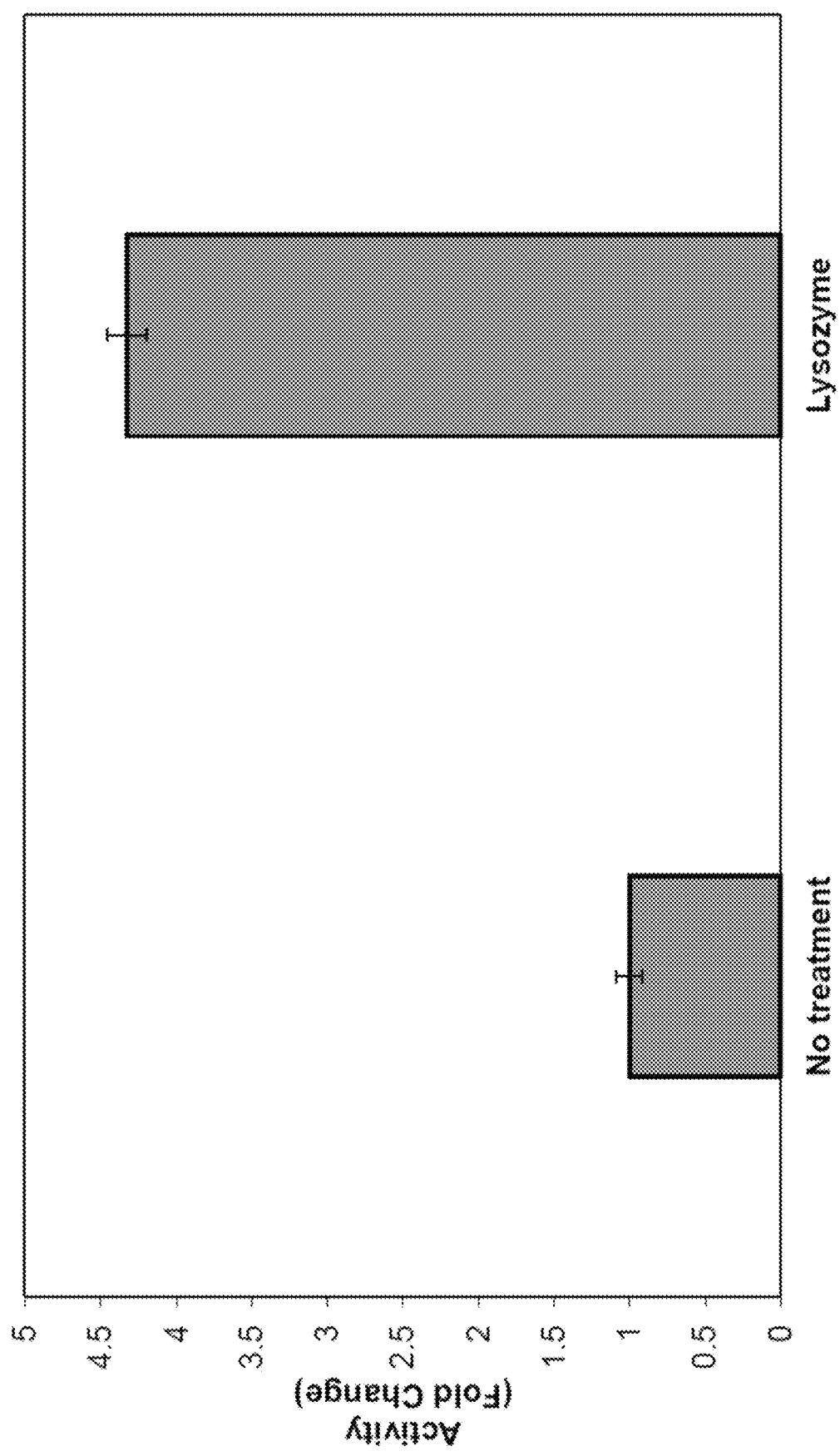

FIG. 11. Lysozyme treated cells have enhanced tagatose production. Comparing tagatose production of encapsulated LsLAI (IC2) having undergone treatment with 0.01 µM lysozyme (right) normalized to untreated cells "No Treatment" (left) in the presence of 200 mM galactose after 2 h incubation at 37° C. The data are means from three biological replicates.

Figure 12:
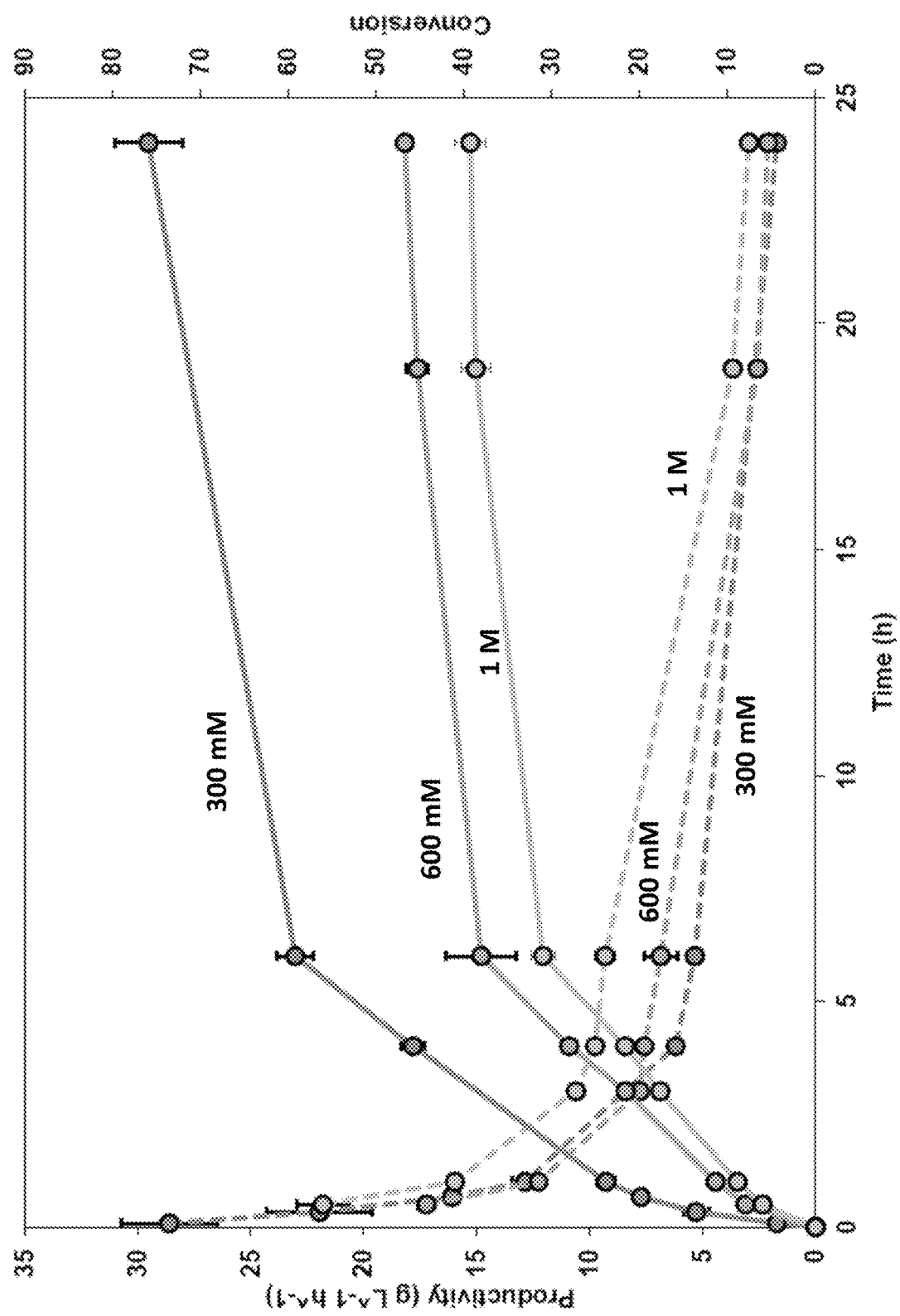

FIG. 12. Comparing conversion and productivity of SDS treated encapsulated LsLAI at different initial galactose concentrations. Measuring the conversion and average productivity of tagatose production using permeabilized encapsulated LsLAI incubated at 50° C. "SDS-50C" at 300 mM galactose, 600 mM galactose, or 1 M galactose. Average productivity calculated at each sample timepoint. Inset shows initial reaction rates. Data for 300 mM galactose taken from FIG. 4 of this work. The data are means from three biological replicates.

Figure 13:
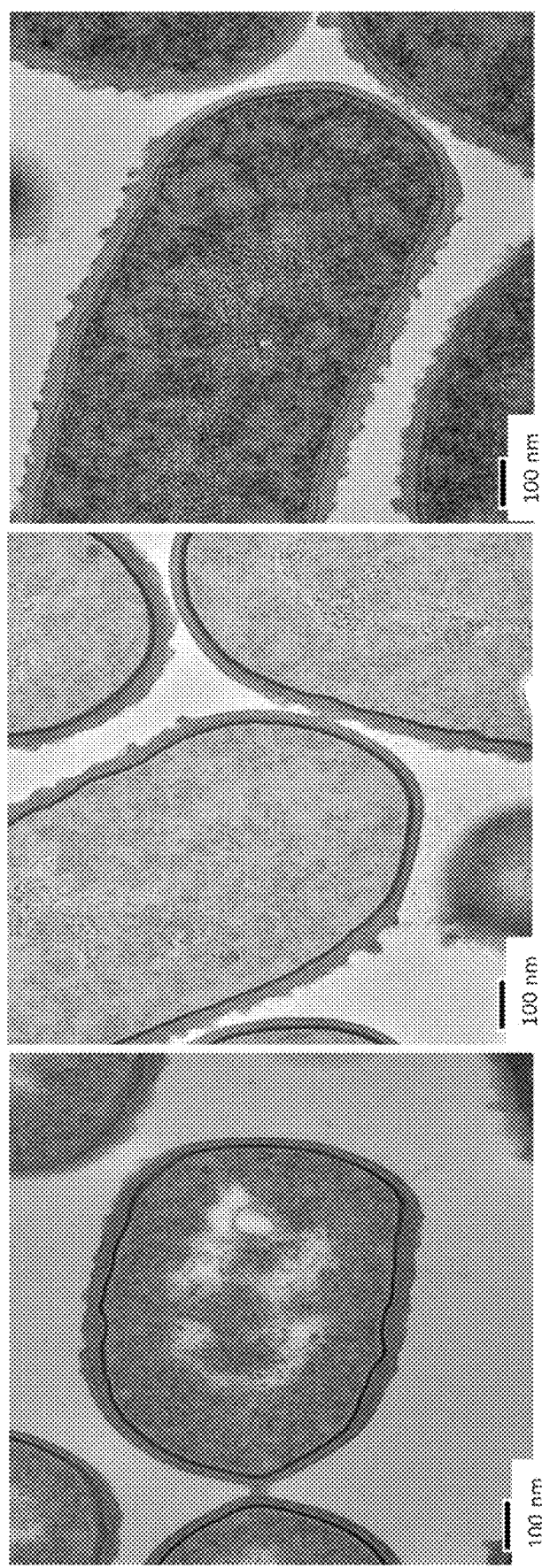

FIG. 13. TEM analysis of SDS permeabilized *L. plantarum*. Transmission electron microscopy of *L. plantarum* cells to study the effects of 0.01% SDS permeabilization on cellular structure. Left, Wild-type *L. plantarum* in PBS. Middle, Strain IC2 intracellularly expressing LsLAI in PBS. Right, Strain IC2 intracellularly expressing LsLAI treated with 0.01% SDS. HV=80.0 kV. Direct Mag: 49000×.

Figure 14A:
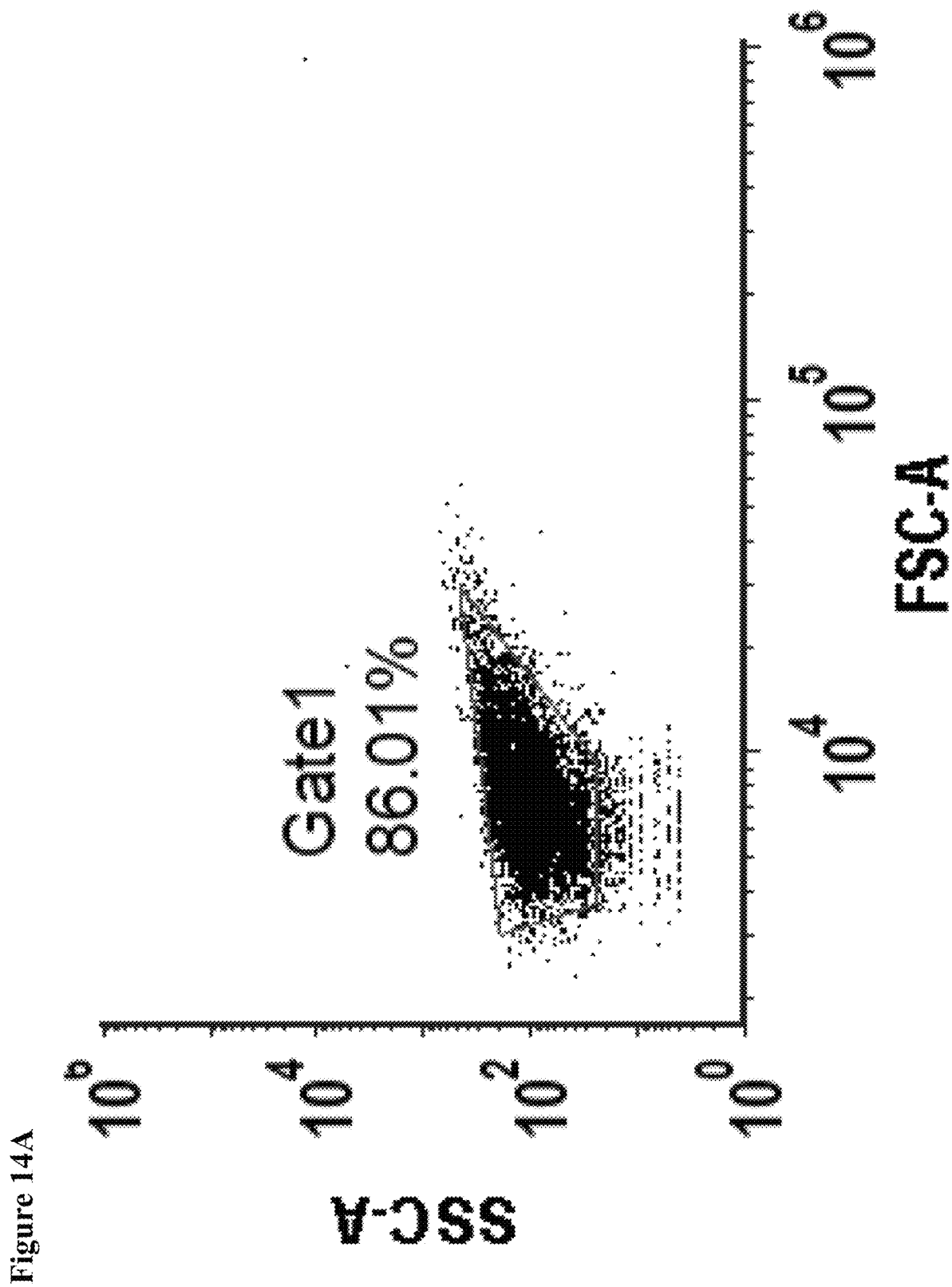
Figure 14B:
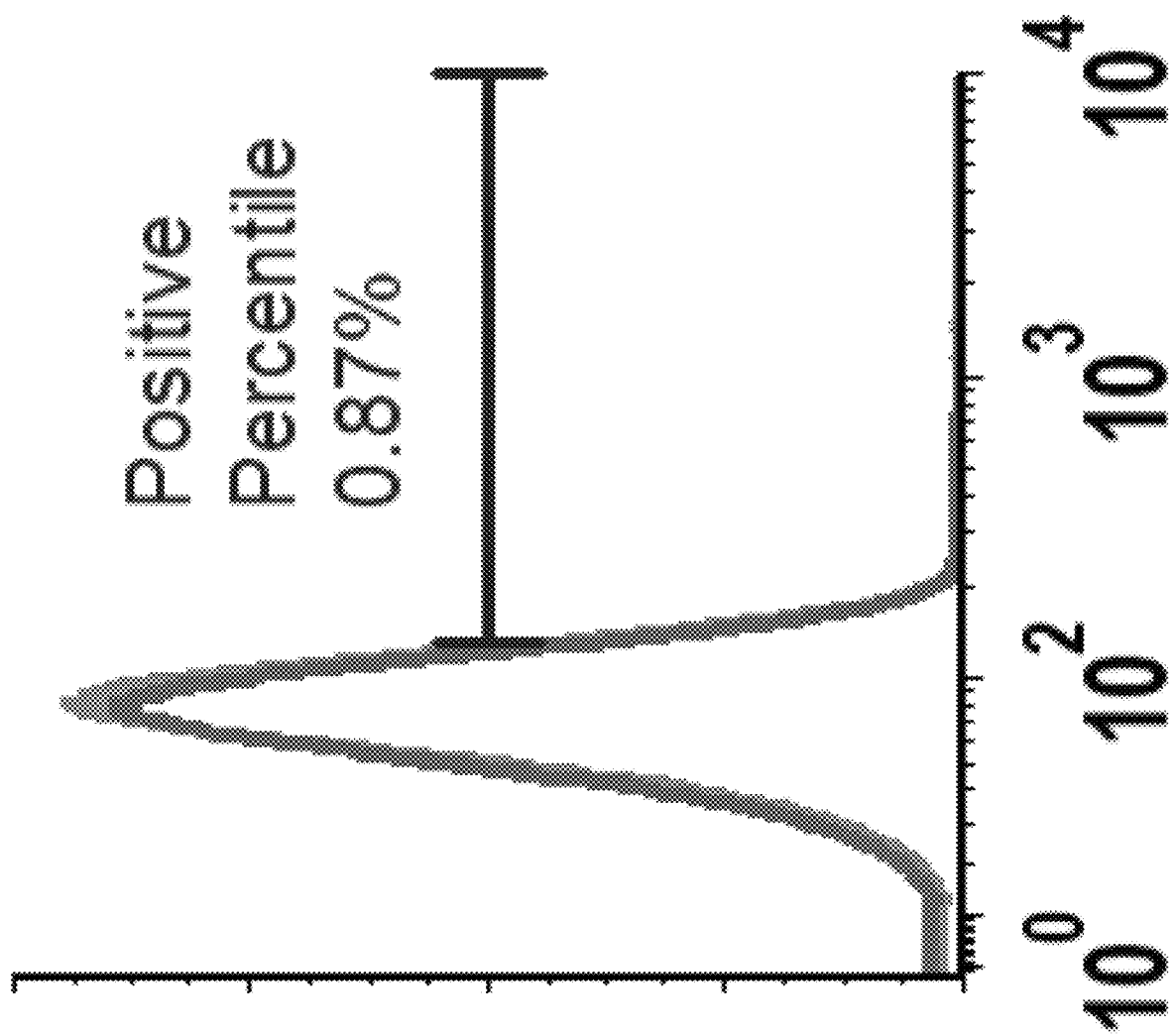

FIG. 14A and FIG. 14B. Flow cytometry analysis gating. FIG. 14A) Population gating of the negative control (wild-type). Axes are bio-exponential. FIG. 14B) Marker of the negative controls wild-type and intracellularly expressed LsLAI with His6-tag. Histogram counts normalized. Plotted on bio-exponential x-axis. Positive percentile marker is shown. Gating strategy used for all flow-cytometry experiments.

Figure 15:
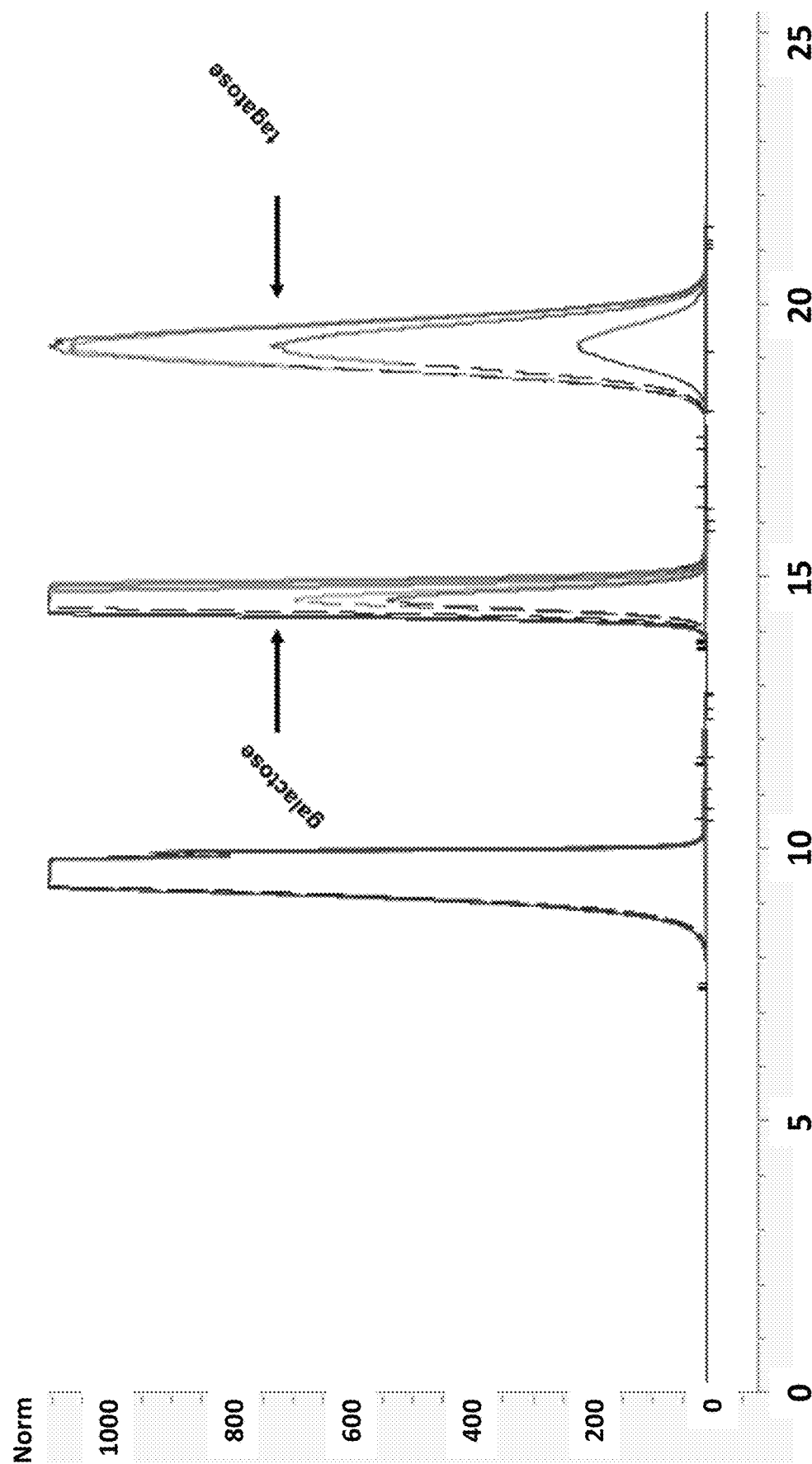

FIG. 15. HPLC chromatograms of tagatose production samples using strain IC2+SDS at 50° C. ELSD chromatogram signals at 0, 6, 24, and 48 h timepoints. One representative figure of triplicate samples.

FIG. 16A, FIG. 16B, FIG. 16C, and FIG. 16D. Assesing the potential of A) LsH and LpH expressed in *L. plantarum* and B) LpH expressed in *S. cerevisiae* for tagatose production at varying temperatures. Lp or Sc alone was used as negative control. C) Growth of Lp tested at elevated temperatures. D) ALE of Lp for adapting the growth at higher temperature. Dotted circles are passages at 37° C. to revive the culture during ALE.

DETAILED DESCRIPTION

Definitions and Terminology

The disclosed subject matter may be described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a gene" or "an oligosaccharide" should be interpreted to mean "one or more genes" and "one or more oligosaccharides," respectively, unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

Polynucleotides and Synthesis Methods

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

The term "promoter" refers to a cis-acting DNA sequence that directs RNA polymerase and other trans-acting transcription factors to initiate RNA transcription from the DNA template that includes the cis-acting DNA sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. As used herein, "expression template" and "transcription template" have the same meaning and are used interchangeably.

In certain exemplary embodiments, vectors such as, for example, expression vectors, containing a nucleic acid encoding one or more polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably.

In certain exemplary embodiments, the recombinant expression vectors comprise a nucleic acid sequence in a form suitable for expression of the nucleic acid sequence in one or more of the methods described herein, which means that the recombinant expression vectors include one or more regulatory sequences which is operatively linked to the nucleic acid sequence to be expressed. The engineered strains disclosed herein may comprise an expression vector which is episomal, such as a plasmid, and/or the engineered strains disclosed herein may comprise an expression vector which is inserted into the genome of the engineered strains.

The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Expression vectors discloses herein by express an exogenous L-arabinose isomerase enzyme.

As utilized herein, a "deletion" means the removal of one or more nucleotides relative to the native polynucleotide sequence. The engineered strains that are disclosed herein may include a deletion in one or more genes. Preferably, a deletion results in a non-functional gene product.

As utilized herein, an "insertion" means the addition of one or more nucleotides to a native polynucleotide sequence. The engineered strains that are disclosed herein may include an insertion in one or more genes. In some embodiments, the engineered strains that are disclosed herein include an insertion of a sequence encoding an exogenous L-arabinose isomerase enzyme. In some embodiments, the engineered strains that are disclosed herein include an insertion in an endogenous gene (i.e., a genomic insertion) which results in a non-functional gene product.

As utilized herein, a "substitution" means replacement of a nucleotide of a native polynucleotide sequence with a nucleotide that is not native to the polynucleotide sequence. The engineered strains that are disclosed herein may include a substitution in one or more genes. In some embodiments, a substitution results in a non-functional gene product, for example, where the substitution introduces a premature stop codon (e.g., TAA, TAG, or TGA) in the coding sequence of the gene product. In some embodiments, the engineered strains that are disclosed herein may include two or more substitutions where the substitutions introduce multiple premature stop codons (e.g., TAATAA, TAGTAG, or TGATGA).

In some embodiments, the engineered strains disclosed herein may be engineered to include and express one or exogenous genes. As would be understood in the art, an exogenous gene is a gene that is not naturally present in the engineered strain as the strain occurs in nature. For example, a gene that is heterologous to *Lactobacillus plantarum* or *E. coli* is a gene that does not occur in *L. plantarum* or *E. coli*, respectively and may be a gene that occurs naturally in another microorganism or a gene that does not occur naturally in any other known microorganism (i.e., an artificial gene).

Peptides, Polypeptides, Proteins, and Synthesis Methods

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard or unnatural amino acids. The term "amino acid residue" may include alpha-, beta-, gamma-, and delta-amino acids.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length ≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

Reference may be made herein to peptides, polypeptides, proteins and variants or derivatives thereof. Reference amino acid sequences may include, but are not limited to, the amino acid sequence of any of SEQ ID NO: 1.

L-arabinose isomerase [*Lactobacillus sakei*], GenBank: AYG31190. L, SEQ ID NO: 1

1 mlntenyefw fvtgsqslyg eetlrsvekd akeiveklna shqlpyp-
ivf klvattadni 61 tkvmkeanyn dhvagvitwm htfspaknwi rgtkllqkpl
lhlatqflnk ipydtidfdy 121 mnlnqsahgd reyafinarl rknnkiisgy wgdedvqkam
akwmdvavay nesfkikvvt 181 fadkmrnvav tdgdkveaqi kfgwtvdywg vgdlvaevna
vseadidaky adlqkeydfv 241 egqntpekfe hnvkyqirey fglkkfmddr gytafttnfe dlv-
gleqlpg laaqllmaeg 301 ygfagegdwk taaldrllki mahnektvfm edytldlrqg
heailgshml evdpsiasdk 361 prvevhpldi gdkddparlv ftgmqgdavd vtmadygdef klm-
sydvrgn kpeadtphlp 421 vakqlwtpkq glregavgwl tvggghhtvl sfavdseqlq
dlshlfdlty vnik Variants or derivatives as contemplated herein may have an amino acid sequence that includes conservative amino acid substitutions relative to a reference amino acid sequence. For example, a variant or derivative peptide, polypeptide, or protein as contemplated herein may include conservative amino acid substitutions and/or non-conservative amino acid substitutions relative to a reference peptide, polypeptide, or protein. "Conservative amino acid substitutions" are those substitutions that are predicted to interfere least with the properties of the reference peptide, polypeptide, or protein, and "non-conservative amino acid substitution" are those substitution that are predicted to interfere most with the properties of the reference peptide, polypeptide, or protein. In other words, conservative amino acid substitutions substantially conserve the structure and the function of the reference peptide, polypeptide, or protein. The following table provides a list of exemplary conservative amino acid substitutions.

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |

| Original Residue | Conservative Substitution |
|---|---|
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain: (a) the structure of the peptide, polypeptide, or protein backbone in the area of the substitution, for example, as a beta sheet or alpha helical conformation, (b) the charge or hydrophobicity of the molecule at the site of the substitution, and/or (c) the bulk of the side chain. Non-conservative amino acid substitutions generally disrupt: (a) the structure of the peptide, polypeptide, or protein backbone in the area of the substitution, for example, as a beta sheet or alpha helical conformation, (b) the charge or hydrophobicity of the molecule at the site of the substitution, and/or (c) the bulk of the side chain.

Variants or derivatives comprising deletions relative to a reference amino acid sequence of peptide, polypeptide, or protein are contemplated herein. A "deletion" refers to a change in the amino acid or nucleotide sequence that results in the absence of one or more amino acid residues or nucleotides relative to a reference sequence. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

Variants or derivatives comprising a fragment of a reference amino acid sequence of a peptide, polypeptide, or protein are contemplated herein. A "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 21, 22, 23, 24, 25, 26, 27, 28, 29, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full length polypeptide.

Variants or derivatives comprising insertions or additions relative to a reference amino acid sequence of a peptide, polypeptide, or protein are contemplated herein. The words "insertion" and "addition" refer to changes in an amino acid or sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues.

Fusion proteins also are contemplated herein. A "fusion protein" refers to a protein formed by the fusion of at least one peptide, polypeptide, or protein or variant or derivative thereof as disclosed herein to at least one heterologous protein peptide, polypeptide, or protein (or fragment or variant or derivative thereof). The heterologous protein(s) may be fused at the N-terminus, the C-terminus, or both termini of the peptides or variants or derivatives thereof.

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number (e.g., SEQ ID NO:1), or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant" or "derivative" of a particular polypeptide sequence may be defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" or "derivative" may have substantially the same functional activity as a reference polypeptide (e.g., glycosylase activity or other activity). "Substantially isolated or purified" amino acid sequences are contemplated herein. The term "substantially isolated or purified" refers to amino acid sequences that are removed from their natural environment, and are at least 60% free, preferably at least 75% free, and more preferably at least 90% free, even more preferably at least 95% free from other components with which they are naturally associated. Variant or derivative polypeptides as contemplated herein may include variant or derivative polypeptides of SEQ ID NO:1).

Reactions and Components

The term "reaction mixture," as used herein, refers to a solution containing reagents necessary to carry out a given reaction. A reaction mixture is referred to as complete if it contains all components necessary to perform the reaction. Components for a reaction mixture may be stored together in a single container or separately in separate containers, each containing one or more of the total components. Components may be packaged separately for commercialization and useful commercial kits may contain one or more of the reaction components for a reaction mixture.

The steps of the methods described herein can be performed in any suitable order unless otherwise indicated herein or otherwise clearly contradicted by context. The steps may be repeated or reiterated any number of times to achieve a desired goal unless otherwise indicated herein or otherwise clearly contradicted by context.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The disclosed components may be in crude form and/or may be at least partially isolated and/or purified. As used herein, the term "isolated or purified" may refer to components that are removed from their natural environment and/or media, and are at least 60% free, preferably at least 75% free, and more preferably at least 90% free, even more preferably at least 95% free from other components with which they are naturally associated and/or media.

Galactose to Tagatose Isomerization at Moderate Temperature with High Conversion and Productivity Disclosed are components and methods for preparing tagatose from galactose via isomerization reactions using engineered components.

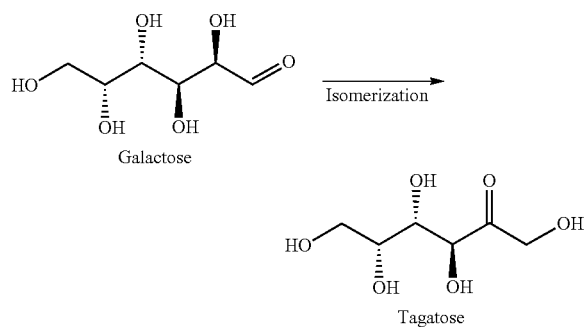

The engineered components include microbial cells and methods for preparing microbial cells that have been engineered to catalyze isomerization of galactose to tagatose, in which the microbial cells express cytoplasmically an exogenous L-arabinose isomerase enzyme (EC 5.3.1.4). In some embodiments, the L-arabinose isomerase enzyme is not secreted by the microbial cells and/or the L-arabinose isomerase enzyme is modified by a component (e.g., a protein anchor) that results in the L-arabinose isomerase enzyme being retained in the cytoplasm of the microbial cells.

The disclosed microbial cells may further be modified for use in methods for preparing tagatose from galactose via isomerization reactions where the microbial cells optionally are treated with reagents that permeabilize the cells. The disclosed methods enable isomerization reactions of galactose to tagatose at relatively high rates, high conversions, and elevated temperatures.

The subject matter disclosed herein includes microbial cells, methods of using microbial cells, and methods of making microbial cells, where the microbial cells have been engineered to catalyze isomerization of galactose to tagatose. Typically, the microbial cells have been engineered to express cytoplasmically an exogenous L-arabinose isomerase enzyme. In some embodiments, the recombinant enzyme is not surface bound or secreted.

Suitable exogenous enzymes may include but are not limited to *Lactobacillus sakei* L-arabinose isomerase, or a variant thereof. Preferably, the enzyme catalyzes conversion of D-galactose to D-tagatose. Variants enzymes may include variants of *Lactobacillus sakei* L-arabinose isomerase that have been engineered to exhibit increased catalytic efficiency for D-galactose as a substrate for conversion to D-tagatose.

Suitable exogenous enzymes may include variants comprising an amino acid sequence having at least about 70% sequence identity with SEQ ID NO: 1, or at least about 80% sequence identity with SEQ ID NO: 1, or at least about 90% sequence identity with SEQ ID NO: 1, or at least about 95% sequence identity with SEQ ID NO: 1, or at least about 97% sequence identity with SEQ ID NO: 1, or at least about 99% sequence identity with SEQ ID NO:1. Preferably, variant enzymes catalyze the conversion of D-galactose to D-tagatose with a catalytic efficiency that is equivalent or better than the catalytic efficiency of *Lactobacillus sakei* L-arabinose isomerase. In some embodiments, a enzyme has from one to twenty, or from one to ten, or from one to five amino acid modifications with respect to SEQ ID NO: 1, wherein the amino acid modifications are independently selected from amino acid substitutions, insertions, and deletions.

In some embodiments, suitable microbial cells for the disclosed components and methods may include gram-positive bacteria. Suitable gram positive bacteria may include a lactic acid bacteria. Suitable gram positive bacteria may include but are not limited to *Lactobacillus* spp. (e.g., *Lactobacillus plantarum*). Suitable gram positive bacteria may include, but are not limited to *Bacillus* spp., *Corynebacterium* spp, or *Brevibacterium* spp., and optionally *Bacillus subtilis* or *Corynebacterium glutamicum*.

In some embodiments, suitable microbial cells for the disclosed components and methods may include gram-negative bacteria. Suitable gram-negative bacteria may include but are not limited to *E. coli*. Suitable gram negative bacteria may include but are not limited to *Rhodobacter* spp, *Zymomonas* spp, *Vibrio* spp., *Agrobacterium* spp., *Paracoccus* spp., or *Pseudomonas* spp. and which is optionally selected from *Rhodobacter capsulatus*, *Rhodobacter sphaeroides*, *Zymomonas mobilis*, *Vibrio natriegens*, and *Pseudomonas putida*.

In some embodiments, suitable microbial cells for the disclosed components and methods may include yeast cells. Suitable yeast cells may include but are not limited to *Saccharomyces* spp., *Schizosaccharomyces* spp., *Pichia* spp., *Phaffia* spp., *Kluyveromyces* spp., *Candida* spp., *Talaromyces* spp., *Brettanomyces* spp., *Pachysolen* spp., *Debaryomyces* spp., or *Yarrowia* spp. Suitable yeast cells may include but are not limited to *Saccharomyces cerevisiae*, *Pichia pastoris*, or *Yarrowia lipolytica*.

Suitable microbial cells for the disclosed components and methods may be permeabilized. In some embodiments, the microbial cells are permeabilized by treating the microbial cell with a detergent. In some embodiments, the detergent is a non-ionic surfactant. In other embodiments, the detergent is an ionic surfactant, and optionally an anionic surfactant. Suitable detergents may include, but are not limited to sodium dodecyl sulfate (SDS). In some embodiments, the microbial cells are treated with a concentration of the detergent is that is below the detergent's critical micelle concentration (CMC). Optionally, the microbial cells are treated with a concentration of SDS that is from about 0.001% to about 0.1%, and optionally from about 0.005% to about 0.05%, and optionally about 0.01%.

Suitable microbial cells may be engineered to express or overexpress sugar transporter proteins, for example, sugar transporter proteins that transport D-galactose and/or D-tagatose. In some embodiments, the microbial cells are engineered to express or overexpress a sugar transporter protein described in WO 2019/099649, which is hereby incorporated by reference in its entirety.

Suitable microbial cells for the disclosed components and methods may be engineered to include a genetic modification that increases the permeability of the microbial cells, for example, permeability for D-galactose and/or D-tagatose.

In some embodiments, the microbial cells may be treated with an enzyme in order to increase their permeability. In some embodiments, the microbial cells are gram-positive cells that are treated with the enzyme lysozyme.

Also disclosed are methods for catalyzing isomerization of galactose to tagatose. The disclosed methods may include providing galactose to a culture of microbial cells as disclosed herein and recovering tagatose from the culture. In some embodiments of the disclosed methods, a feedstock comprising galactose is added to the culture, optionally where the feedstock comprises galactose in the range of from about 100 mM to about 600 mM, and optionally in the range of from about 200 mM to about 400 mM.

In some embodiments of the disclosed methods, a feedstock is added to the culture that comprises a disaccharide or oligosaccharide comprising galactose, which is optionally lactose. Optionally, the microbial cells an endogenous and/or exogenous lactose transport system and an endogenous and/or exogenous lactase.

In some embodiments of the disclosed methods, the microbial cells may have been engineered to include one or more genetic modifications that decrease or inactivate conversion of galactose to glucose. In some embodiments of the disclosed methods, the microbial cells may be engineered to at least partially inactivate an enzyme selected from galactokinase, galactose-1-phosphate uridinyltransferase, and UDP-galactose-4' epimerase.

In some embodiments of the disclosed methods, the feedstock that is added to the cell culture may comprise a non-C6 carbon source.

In some embodiments of the disclosed methods, the culture may be maintained at a temperature greater than about 30° C., or greater than about 32° C., or greater than about 34° C., or greater than about 36° C., or greater than about 38° C., or greater than about 34° C., or greater than about 36° C., or greater than about 38° C., or greater than about 40° C., or greater than about 42° C. or greater than about 44° C. or greater than about 46° C. or greater than about 48° C. or greater than about 50° C., optionally for at least about 1, 2, 4, 6, 8, 10, 12, 14, 16, 18, 20, 22, or 24 hours. In some embodiments of the disclosed methods, the culture is maintained at about 37° C., optionally for at least about 1, 2, 4, 6, 8, 10, 12, 14, 16, 18, 20, 22, or 24 hours.

In the disclosed methods, galactose may be converted to tagatose. In some embodiments of the disclosed methods, the amount of galactose converted to tagatose after about 24 hours is at least about 50%, or at least about 75%, or at least about 85%, or at least about 90%.

In the disclosed methods, tagatose may be recovered from the cell culture. In some embodiments of the disclosed methods, tagatose is recovered from the cellular fraction of the culture. In other embodiments of the disclosed methods, tagatose is recovered from the soluble fraction of the culture. In further embodiments of the disclosed methods, tagatose is recovered from the soluble fraction and cellular fraction.

ILLUSTRATIVE EMBODIMENTS

The following embodiments are illustrative and should not be interpreted to limit the scope of the claimed subject matter.

Embodiment 1

A microbial cell that has been engineered to catalyze isomerization of galactose to tagatose, the microbial cell expressing cytoplasmically an exogenous L-arabinose isomerase enzyme.

Embodiment 2

The microbial cell of embodiment 1, wherein the recombinant enzyme is not surface bound or secreted.

Embodiment 3

The microbial cell of embodiment 1 or 2, wherein the enzyme is *Lactobacillus sakei* L-arabinose isomerase, or a variant thereof.

Embodiment 4

The microbial cell of embodiment 3, wherein the enzyme catalyzes conversion of D-galactose to D-tagatose.

Embodiment 5

The microbial cell of embodiment 4, wherein the enzyme is a variant of *Lactobacillus sakei* L-arabinose isomerase and is engineered to exhibit increased catalytic efficiency for D-galactose substrate.

Embodiment 6

The microbial cell of any one of embodiments 3 to 5, wherein the enzyme has at least about 70% sequence identity with SEQ ID NO: 1, or at least about 80% sequence identity with SEQ ID NO: 1, or at least about 90% sequence identity with SEQ ID NO: 1, or at least about 95% sequence identity with SEQ ID NO: 1, or at least about 97% sequence identity with SEQ ID NO: 1, or at least about 99% sequence identity with SEQ ID NO:1.

Embodiment 7

The microbial cell of embodiment 6, wherein the enzyme has from one to twenty, or from one to ten, or from one to five amino acid modifications with respect to SEQ ID NO: 1, wherein the amino acid modifications are independently selected from amino acid substitutions, insertions, and deletions.

Embodiment 8

The microbial cell of any one of embodiments 1 to 7, wherein the microbial cell is a gram-positive bacteria.

Embodiment 9

The microbial cell of embodiment 8, wherein the gram positive bacteria is a lactic acid bacteria.

Embodiment 10

The microbial cell of embodiment 9, wherein the gram positive bacteria is a *Lactobacillus*.

Embodiment 11

The microbial cell of embodiment 10, wherein the *Lactobacillus* is *Lactobacillus* plantarum.

Embodiment 12

The microbial cell of embodiment 8, wherein the gram positive bacteria is selected from *Bacillus* spp., *Corynebacterium* spp, or *Brevibacterium* spp., and optionally *Bacillus subtilis* or *Corynebacterium glutamicum*.

Embodiment 13

The microbial cell of any one of embodiments 1 to 7, wherein the microbial cell is a gram negative bacterial cell.

Embodiment 14

The microbial cell of embodiment 13, wherein the microbial cell is *E. coli*.

Embodiment 15

The microbial cell of embodiment 13, wherein the bacterial cell is selected from *Rhodobacter* spp, *Zymomonas* spp, *Vibrio* spp., *Agrobacterium* spp., *Paracoccus* spp., or *Pseudomonas* spp. and which is optionally selected from *Rhodobacter capsulatus*, *Rhodobacter sphaeroides*, *Zymomonas mobilis*, *Vibrio natriegens*, and *Pseudomonas putida*.

Embodiment 16

The microbial cell of any one of embodiments 1 to 7, wherein the microbial cell is a yeast cell.

Embodiment 17

The microbial cell of embodiment 16, wherein the yeast cell is selected from *Saccharomyces* spp., *Schizosaccharomyces* spp., *Pichia* spp., *Phaffia* spp., *Kluyveromyces* spp., *Candida* spp., *Talaromyces* spp., *Brettanomyces* spp., *Pachysolen* spp., *Debaryomyces* spp., or *Yarrowia* spp.

Embodiment 18

The microbial cell of embodiment 17, wherein the yeast cell is *Saccharomyces cerevisiae*, *Pichia pastoris*, or *Yarrowia lipolytica*.

Embodiment 19

The microbial cell of any one of embodiments 1 to 18, wherein the microbial cell is permeabilized.

Embodiment 20

The microbial cell of embodiment 19, wherein the microbial cell is permeabilized by treating the microbial cell with a detergent.

Embodiment 21

The microbial cell of embodiment 20, wherein the detergent is a non-ionic surfactant.

Embodiment 22

The microbial cell of embodiment 20, wherein the detergent is an ionic surfactant, and optionally an anionic surfactant.

Embodiment 23

The microbial cell of embodiment 22, wherein the detergent is sodium dodecyl sulfate (SDS).

Embodiment 24

The microbial cell of any one of embodiments 20 to 23, wherein the microbial cell is treated with a concentration of the detergent is that is below the detergent's critical micelle concentration (CMC).

Embodiment 25

The microbial cell of embodiment 23, wherein the microbial cell is treated with a concentration of SDS that is from about 0.001% to about 0.1%, and optionally from about 0.005% to about 0.05%, and optionally about 0.01%.

Embodiment 26

The microbial cell of any one of embodiments 1 to 25, wherein the microbial cell overexpresses of one or more sugar transporters, and optionally a transporter described in WO 2019/099649, which is hereby incorporated by reference in its entirety.

Embodiment 27

The microbial cell of any one of embodiments 1 to 26, comprising one or more genetic modifications that increase the membrane permeability of the microbial cell for D-galactose; and/or wherein the microbial cell expresses an endogenous and/or recombinant lactose transport system and an endogenous and/or recombinant lactase; and/or wherein the microbial cell has one or more genetic modifications that decrease or inactivate conversion of galactose to glucose.

Embodiment 28

The microbial cell of any one of embodiments 8 to 12, wherein the microbial cell is permeabilized by treating the microbial cell with lysozyme.

Embodiment 29

A method for catalyzing isomerization of galactose to tagatose, comprising: providing galactose to a culture of the microbial cell of any one of embodiments 1 to 28, and recovering tagatose from the culture.

Embodiment 30

The method of embodiment 29, wherein a feedstock comprising galactose is added to the culture.

Embodiment 31

The method of embodiment 30, wherein the feedstock comprises galactose in the range of from about 100 mM to about 600 mM, and optionally in the range of from about 200 mM to about 400 mM.

Embodiment 32

The method of embodiment 29, wherein the feedstock comprise a disaccharide or oligosaccharide comprising galactose, and which is optionally lactose.

Embodiment 33

The method of embodiment 32, wherein the microbial cell expresses an endogenous and/or recombinant lactose transport system and an endogenous and/or recombinant lactase.

Embodiment 34

The method of any one of embodiments 29 to 33, wherein the microbial cell has one or more genetic modifications that decrease or inactivate conversion of galactose to glucose.

Embodiment 35

The method of embodiment 34, wherein the microbial cell has at least a partial inactivation of at least one of galactokinase, galactose-1-phosphate uridinyltransferase, and UDP-galactose-4' epimerase.

Embodiment 36

The method of any one of embodiments 29 to 35, wherein the feedstock comprises a non-C6 carbon source.

Embodiment 37

The method of embodiment 29, wherein the culture is maintained at a temperature greater than about 30° C., or greater than about 32° C., or greater than about 34° C., optionally for at least about 1, 2, 4, 6, 8, 10, 12, 14, 16, 18, 20, 22, or 24 hours.

Embodiment 38

The method of embodiment 37, wherein the culture is maintained at about 37° C., optionally for at least about 1, 2, 4, 6, 8, 10, 12, 14, 16, 18, 20, 22, or 24 hours.

Embodiment 39

The method of any one of embodiments 29 to 38, wherein the amount of galactose converted to tagatose after about 24 hours is at least about 50%, or at least about 75%, or at least about 85%, or at least about 90%.

Embodiment 40

The method of any one of embodiments 29 to 39, wherein the tagatose is recovered from the cellular fraction of the culture.

Embodiment 41

The method of embodiment 40, wherein the tagatose is recovered from the soluble fraction of the culture.

Embodiment 42

The method of embodiment 40, wherein the tagatose is recovered from the soluble fraction and cellular fraction.

Embodiment 43

A method for preparing a microbial cell comprising: (i) engineering the microbial cell to express cytoplasmically an exogenous L-arabinose isomerase enzyme; and (ii) treating the engineered microbial cell with a detergent at a concentration that is below the detergent's critical micelle concentration (CMC).

Embodiment 44

The method of embodiment 43, wherein the recombinant enzyme is not surface bound or secreted.

Embodiment 45

The method of embodiment 43 or 44, wherein the enzyme is *Lactobacillus sakei* L-arabinose isomerase, or a variant thereof.

Embodiment 46

The method of embodiment 45, wherein the enzyme catalyzes conversion of D-galactose to D-tagatose.

Embodiment 47

The method of embodiment 46, wherein the enzyme is a variant of *Lactobacillus sakei* L-arabinose isomerase and is engineered to exhibit increased catalytic efficiency for D-galactose substrate.

Embodiment 48

The method of any one of embodiments 45 to 47, wherein the enzyme has at least about 70% sequence identity with SEQ ID NO: 1, or at least about 80% sequence identity with SEQ ID NO: 1, or at least about 90% sequence identity with SEQ ID NO: 1, or at least about 95% sequence identity with SEQ ID NO: 1, or at least about 97% sequence identity with SEQ ID NO: 1, or at least about 99% sequence identity with SEQ ID NO:1.

Embodiment 49

The method of embodiment 48, wherein the enzyme has from one to twenty, or from one to ten, or from one to five amino acid modifications with respect to SEQ ID NO: 1, wherein the amino acid modifications are independently selected from amino acid substitutions, insertions, and deletions.

Embodiment 50

The method of any one of embodiments 43 to 49, wherein the microbial cell is a gram-positive bacteria.

Embodiment 51

The method of embodiment 50, wherein the gram positive bacteria is a lactic acid bacteria.

Embodiment 52

The method of embodiment 51, wherein the gram positive bacteria is a *Lactobacillus*.

Embodiment 53

The method of embodiment 52, wherein the *Lactobacillus* is *Lactobacillus* plantarum.

Embodiment 54

The method of embodiment 50, wherein the gram positive bacteria is selected from *Bacillus* spp., *Corynebacterium* spp, or *Brevibacterium* spp., and optionally *Bacillus subtilis* or *Corynebacterium glutamicum*.

Embodiment 55

The method of any one of embodiments 43 to 49, wherein the microbial cell is a gram negative bacterial cell.

Embodiment 56

The method of embodiment 55, wherein the microbial cell is *E. coli*.

Embodiment 57

The method of embodiment 55, wherein the bacterial cell is selected from *Rhodobacter* spp, *Zymomonas* spp, *Vibrio* spp., *Agrobacterium* spp., *Paracoccus* spp., or *Pseudomonas* spp. and which is optionally selected from *Rhodobacter capsulatus*, *Rhodobacter sphaeroides*, *Zymomonas mobilis*, *Vibrio natriegens*, and *Pseudomonas putida*.

Embodiment 58

The method of any one of embodiments 43 to 49, wherein the microbial cell is a yeast cell.

Embodiment 59

The method of embodiment 58, wherein the yeast cell is selected from *Saccharomyces* spp., *Schizosaccharomyces* spp., *Pichia* spp., *Phaffia* spp., *Kluyveromyces* spp., *Candida* spp., *Talaromyces* spp., *Brettanomyces* spp., *Pachysolen* spp., *Debaryomyces* spp., or *Yarrowia* spp.

Embodiment 60

The method of embodiment 59, wherein the yeast cell is *Saccharomyces cerevisiae*, *Pichia pastoris*, or *Yarrowia lipolytica*.

Embodiment 61

The method of any one of embodiments 43 to 60, wherein the microbial cell is permeabilized.

Embodiment 62

The method of embodiment 43, wherein the detergent is a non-ionic surfactant.

Embodiment 63

The method of embodiment 43, wherein the detergent is an ionic surfactant, and optionally an anionic surfactant.

Embodiment 64

The method of embodiment 43, wherein the detergent is sodium dodecyl sulfate (SDS).

Embodiment 65

The method of embodiment 64, wherein the microbial cell is treated with a concentration of the SDS that is from about 0.001% to about 0.1%, and optionally from about 0.005% to about 0.05%, and optionally about 0.01%.

Embodiment 66

The method of any one of embodiments 43 to 65, wherein the microbial cell overexpresses of one or more sugar transporters, and optionally a transporter described in WO 2019/099649, which is hereby incorporated by reference in its entirety.

Embodiment 67

The method of any one of embodiments 43 to 66, comprising one or more genetic modifications that increase the membrane permeability of the microbial cell for D-galactose.

Embodiment 68

The method of any one of embodiments 50 to 54, further comprising treating the microbial cell with lysozyme.

EXAMPLES

The following Examples are illustrative and should not be interpreted to limit the scope of the claimed subject matter.

Example 1—Galactose to Tagatose Isomerization at Moderate Temperatures with High Conversion and Productivity Reference is made to Bober & Nair, "Galactose to tagatose isomerization at moderate temperatures with high conversion and productivity," bioRxiv, first posted online Feb. 12, 2019, now published in Nat. Comm. (2019)10:4548, Oct. 7, 2019, the content of which is incorporated herein by reference in its entirety.

Abstract

There are many industrially-relevant enzymes that while active, are severely limited by thermodynamic, kinetic, or stability issues (isomerases, lyases, transglycosidases). In this work, we study *Lactobacillus sakei* L-arabinose isomerase (LsLAI) for D-galactose to D-tagatose isomerization—that is limited by all three reaction parameters. The enzyme demonstrates low catalytic efficiency, low thermostability at temperatures >40° C., and equilibrium conversion <50%. After exploring several strategies to overcome these limitations, we show that encapsulating LsLAI in gram-positive *Lactobacillus plantarum* that is chemically permeabilized enables reactions at high rates, conversion, and temperatures. In a batch process, this system enables ~50% conversion in 4 h starting with 300 mM galactose (an average productivity of 37 mM $h^{-1}$), and 85% conversion in 48 h. We suggest that such an approach may be invaluable for other enzymatic processes that are similarly kinetically-, thermodynamically-, and/or stability-limited.

INTRODUCTION

D-Tagatose is a rare ketohexose sugar with sweetness similar to that of sucrose. However, its glycemic index and caloric value is much lower because of low bioavailability, making it an attractive generally regarded as safe (GRAS) sugar substitute. Recent studies have also demonstrated that it is anti-hyperglycemic[1] and prebiotic, which promotes gut health[2,3]. Thus, there exists a high demand in food industry for the economical production of rare sugars, like tagatose, exemplified by the 2016 global artificial sweetener market estimated to be USD 3.2 billion. This market is expected to expand given the global diabetes crisis and increasing relevance of prebiotics.

The enzyme L-arabinose isomerase (LAI) that responsible for the reversible isomerization of the pentose L-arabinose to L-ribulose can also isomerize the hexose D-galactose to D-tagatose[4,5]. LAI has thus been the enzyme of choice to produce tagatose, although, to date, few commercial bioprocesses exist. A variety of LAIs from different microorganisms have been isolated and have reported optimal activity at a range of temperatures and pH[4,6,7]. Some of the limitations of tagatose biosynthesis using LAI that may be hindering commercial viability are, 1) unfavorable enzymatic kinetics since galactose is not the native substrate of LAI, 2) low enzyme stability, particularly in the absence of divalent metal ions, and 3) low equilibrium constant for galactose to tagatose isomerization.

Few previous reports have been successful at engineering enzymatic properties of LAI for industrial application; often addressing only one of the bottlenecks to productivity. To address the kinetic issue, several groups have used enzyme engineering methods to enhance catalytic efficiency of LAI toward galactose and have shown moderate increases in productivity[8-13]. To counter low-stability issues, many groups have tested the utility of thermophilic enzymes[12,14-16] However, most thermophilic enzymes rely on divalent metal ions ($Mn^{2+}$, $Co^{2+}$, $Fe^{2+}$) for stability[12], and high reaction temperatures (≥80° C.) result in significant caramelization[17], which are all undesirable and must be removed from product, adding to processing costs. Surface-display[18] or encapsulation in particles or whole-cells[19-22] can stabilize enzymes[23]. Finally, the thermodynamic limitations of isomerization of galactose to tagatose are severe and, arguably, the most recalcitrant issue since $\Delta G°_{rxn} \approx +1.19$ kcal $mol^{-1}$ [22], which indicates theoretical maximum equilibrium conversion ~14% at room temperature. Several approaches have been used to try and overcome this limitation, including the use of an oxidoreductive pathway rather than isomerization[24]. However, this method resulted in low productivity, byproduct formation, and the need for a sacrificial substrate to regenerate cofactors and drive the reaction uphill. Thermophilic LAI enzymes can achieve higher conversions than their mesophilic counterparts since the equilibrium shifts toward tagatose at higher temperatures[6]. Whole-cell biocatalysts with GRAS organisms (e.g. lactic acid bacteria (LAB) and *E. coli*) that disproportionately partition substrate and product across their membrane has also been shown to partially circumvent this thermodynamic limitation while simultaneously enhancing enzyme stability; albeit at a kinetic penalty imposed by substrate transport limitations[25-27]. Recently, cell permeabilization[27] and sugar transport overexpression[28,29] were demonstrated as methods to overcome the kinetic penalty imposed by cellular encapsulation.

Studies that systematically analyze and address all three limitations associated with LAI—kinetic, thermodynamic, and stability—can significantly advance development of tagatose biosynthetic processes. This work clearly demonstrates the presence of these three limitations and provides an approach to balance their advantages and limitations. We use the food-safe engineered probiotic bacterium *Lactobacillus plantarum* as the expression host due to its increasing relevance to biochemical and biomedical research[30,31] This approach enables ~50% conversion of galactose to tagatose in 4 h (productivity of ~38 mmol tagatose $L^{-1}$ $h^{-1}$) ultimately reaching ~85% conversion after 48 h at high galactose loading (300 mM) in batch culture. Such an approach is expected to be applicable to other biocatalytic systems where similar trade-offs between kinetics, thermodynamics, and/or stability pose hurdles to process development.

Results

LAI catalyzes tagatose synthesis at low conversion and rate. At high substrate loading (400 mM galactose) and 37° C., the reported optimal temperature for this enzyme[32], LsLAI purified from *L. plantarum* exhibited an initial forward reaction (turnover) rate ($k_{initial}$) of 9.3±0.3 $s^{-1}$, which is lower than the maximum reaction rate possible by this enzyme of 17.0±1.3 $s^{-1}$ $min^{-1}$ with its preferred substrate, arabinose, at 400 mM. Increasing the reaction temperature to 50° C. increased the initial reaction rate to 11.2 $s^{-1}$ (FIG. 1A) but was accompanied by rapid enzyme inactivation, which is consistent with previous reports of thermal instability of this enzyme[32]. The enzyme exhibited first-order degradation with a half-life ($t_{1/2}$) of approximately 18.5 h at 37° C. (FIG. 1B) and 1.5 h at 50° C. Indeed, the enzyme retains only ~6% activity after 6 h at this elevated temperature. Additionally, the highly reversible isomerization reaction suffers from thermodynamic limitations with reported free-enzyme equilibrium conversions <50% ($\Delta G°_{rxn}=+1.19$ kcal $mol^{-1}$)[22]. Our results indicate similar low conversion of 35-40% after 5 days with pure enzyme at 37° C. with daily supplementation of fresh enzyme to account for inactivation (FIG. 1C).

*L. plantarum* cell surface display does not stabilize LsLAI. To achieve surface localization, we fused LsLAI with six *L. plantarum* surface proteins, which have all been previously described as suitable display carriers, at either the C- or N-terminus (Table 4). The constructs also contained the strong Lp_3050 secretion signal, a 10 amino acid linker containing a thrombin protease cleavage site, and either a C- or N-terminal His6 tag for immunofluorescence assays. We characterized surface localization using flow cytometry and measured the whole-cell isomerization activity. All three of the tested C-terminal anchor strains (A1, A2, and A3) exhibited >90% surface detection (FIG. 2A) (see Table 3 for strain descriptions). However, the measured tagatose production after a 2 h incubation with 200 mM galactose was only 225±72, 55±39, 91±25 µM tagatose (normalized to individual reaction cell densities of ~$OD_{600}$=0.5), respectively, significantly less than that of intracellularly expressed (IC1) LsLAI (538±34 µM) (FIG. 2B). LsLAI was detected on N-terminal anchor strains A5 and A6 in 28% and 96% of the population and produced 286±31 and 422±34 tagatose respectively. Interestingly, strain A4 exhibited low surface detection, comparable to control (WT & IC1) cells while producing higher titers of tagatose (533±58 µM) relative to our other surface display constructs. These data indicate there is not a significant correlation (p>0.05) between whole-cell activity with the presence of displayed LsLAI on the L. plantarum cell surface (FIG. 2C).

Next, we sought to explain the observation regarding absence of positive correlation between display level and activity using strain A6. Sodium dodecyl sulfate (SDS) is a strong anionic surfactant that is commonly used to lyse cells through membrane disruption and denature proteins by destabilizing non-covalent bonds. We posited that SDS could be used to extract surface proteins from Gram-positive bacteria without lysing the cells. We incubated strains IC1 and A6 with either PBS (control) or PBS containing 0.5% SDS, to remove surface displayed LsLAI, and then quantified surface detection and whole-cell activity. As expected, we detected LsLAI only on the surface of PBS-treated control A6 but not the SDS-treated cells by flow cytometry (FIG. 5A). Interestingly, whole-cell activity of both IC1 and A6 increased approximately 3- and 5-fold, respectively, post-SDS-treatment. These data suggest LsLAI is present in both the intracellular compartment and membrane bound of strain A6 with the vast majority of measured whole-cell activity coming from the intracellular fraction. We confirmed the presence of soluble anchor-LAI fusion (Lp_3014-LsLAI) in the intracellular fraction of A6 via Western blot analysis (FIG. 5B). Additionally, we noticed enhanced whole-cell activity that we attribute to permeabilization/fluidization of the membrane/cell wall due to removal of surface proteins. While this study only focused one of our six explored anchor protein constructs, we suspect that these results are consistent amongst the other LsLAI surface display constructs. Thus, the measured whole-cell activity differing between constructs was likely dependent on the activity of soluble anchor-LsLAI present in the cytoplasm and not due to surface displayed enzyme.

Finally, to further elucidate the discrepancy between activity of intracellular and surface displayed LsLAI constructs we tested the enzymes activity of secreted, unanchored enzyme. Post-induction, we separated whole cells from culture media and compared the activity of each fraction. We observed a 6-fold higher in activity in the whole-cell fraction of the secretion strain compared to wild-type control cells; however, there was no detectable activity in the supernatant of either strain (FIG. 6A). We confirmed the presence of LsLAI in the supernatant and soluble cell fraction via Western blot analysis (FIG. 6B). These data, taken together with our previous experiments, suggest LsLAI is largely in an inactive state after secretion and that any activity is due to accumulation of active enzyme in the L. plantarum cytoplasm.

Cellular encapsulation improves LAI stability and conversion. Since surface display failed as a stabilization mechanism, yielding minimally active enzyme, we evaluated whether whole-cell L. plantarum cells encapsulating LsLAI via cytoplasmic expression (referred to as encapsulated LAI) could be used as a stabilization method instead. Our data show that such encapsulation within L. plantarum protected the enzyme from thermal deactivation at 50° C.; the enzyme retained ~85% of its initial activity after 24 h (FIG. 3A). Interestingly, resting whole cells at 37° C. displayed no loss of activity after 24 h; in fact, we observed a slight enhancement in activity. This observation could be due to changes to cellular morphology or physiology. Cell-encapsulated LsLAI quickly reached an equilibrium conversion of approximately 60% in 24 h, overcoming the thermodynamic limitation of <50% conversion presented in the pure enzyme system (FIG. 3B). We believe this happens because the substrate (galactose) and product (tagatose) differentially partition across the cell membrane. Although initial reaction rates of encapsulated LsLAI at 37° C. and 50° C. with either galactose or tagatose were lower than that of their free-enzyme counterparts, encapsulated LsLAI favored reaction in the forward direction more than in the reverse direction, as determined by initial rates (FIG. 7). At 50° C. the ratio of forward to reverse initial reaction rate for encapsulated LsLAI was 1.8 whereas for the pure enzyme, the ratio was more unfavorable at 0.7.

To further demonstrate that the L. plantarum cell acts as a selective barrier, we tested the capacity of other sugars to inhibit the rate controlling step of galactose to tagatose isomerization. Tagatose production by cell encapsulated LAI was significantly inhibited in the presence of glucose while the presence of arabinose had no effect (FIG. 8). Conversely, glucose had minimal inhibition on tagatose production in pure enzyme reactions while arabinose (the preferred substrate for LAI) significantly inhibited the production of tagatose. These data suggest that the rate-controlling step in whole cell system and pure enzyme are completely different—sugar transporters in whole cell systems and passive diffusion in pure enzyme systems. Further, since glucose is a highly preferred substrate of L. plantarum, the fact that glucose inhibits whole cell galactose isomerization suggests that the rate-controlling step is one or more glucose-preferring hexose transporter(s).

While encapsulation was shown to provide thermal stability and a thermodynamic advantage, it imposes a kinetic penalty due to transport limitations across the cell membrane. To test this, we measured initial whole-cell activity under a range of induction levels to determine the maximum achievable activity and compared the whole-cell activity to that of the cell lysate at the same conditions. Strain I produced the maximum amount of tagatose (1.5 mM) in 2 h at inducer concentrations ≥5 ng $mL^{-1}$ (FIG. 3C), indicating that this represented that the system is at maximum reaction rate under all these inducer levels. Conversely, lysate of the same cells induced at 5 and 25 ng $mL^{-1}$ inducer conditions generated approximately 4-fold greater tagatose than that of the equivalent whole-cell catalysts in the same 2 h interval. This further supports the idea that cellular encapsulation changes the rate-limiting step to transport and imposes a ceiling on reaction kinetics.

SDS permeabilized cells overcome all three barriers. Seeking to overcome the transport-limited whole-cell production of tagatose, we investigated the use of permeabilization surfactants—Triton X-100 and SDS. Following the same optimized protocol as previously reported for permeabilization of L. plantarum with 1% Triton X-100[27], we observed a 4.2±0.1 fold increase in tagatose production as compared to untreated cells under the tested conditions (FIG. 9A). We assessed the ability of 0.005%-0.5% SDS to permeabilize cell encapsulated LsLAI and enhance tagatose production. Our results showed the optimal concentration of SDS that enhanced tagatose production via cell permeabilization while still retaining LsLAI intracellularly to be 0.01% (FIG. 9B). Tagatose production was enhanced 5.7±0.1 fold after permeabilization with 0.01% SDS, greater than that of treatment with 1% Triton X-100 under the tested conditions. Additionally, this concentration of SDS is below the critical micellular concentration (CMC=0.24-0.26% at 35-40° C.) therefore producing minimal frothing as compared to 1% Triton X-100, the CMC of which is reported to be 0.05%[33]. Although SDS is commonly used to denature proteins, low concentrations of SDS (0.001-0.005%) has been previously used to permeabilize E. coli—albeit less successfully than with CTAB (cetyl trimethylammonium bromide) and Triton X-100[34].

To further understand the effect of SDS-treatment on cell permeability, we measured the fluorescence generation rate using 5-carboxyfluorescein diacetate (cFDA) as a substrate. cFDA is an uncharged ester that becomes fluorescent upon hydrolysis by abundant and nonspecific intracellular esterases. Hydrolysis also results in entrapment of the fluorescent dye in the cytoplasm, unless the membrane has been damaged. The rate of generated fluorescence serves as a proxy to determine substrate transport rates assuming hydrolysis rates are higher than transport rate. Wild-type L. plantarum treated with 0.005%, 0.01%, and 0.05% SDS had 1.6-, 3.0-, and 3.4-fold increase in substrate transport rates, respectively, compared to untreated cells (FIG. 10). SDS concentrations >0.5% resulted in fluorescence leakage, a sign of damaged cell membrane that may also be expelling other cytoplasmic content. These data suggest that the treatment with 0.01% SDS maintains cellular integrity while increasing tagatose synthesis rate due to a decreased kinetic penalty presented upon encapsulation.

To test whether the enhanced transport could be attributed to changes to the Gram-positive cell wall composition, we treated L. plantarum encapsulated LAI (strain IC2) with lysozyme, an enzyme which catalyzes the destruction of the peptidoglycan component of the gram-positive cell wall. Cells treated with lysozyme displayed a 4.3-fold increase in activity like cells chemically treated with SDS detergent compared to untreated cells (FIG. 11 and FIG. 9). These data suggest that the cell wall poses a transport limitation barrier and SDS treatment may be modifying the structure/rigidity of the cell wall to allow faster transport; albeit further direct experimentation should be done to confirm this hypothesis.

Finally, we monitored the tagatose production with different LsLAI catalyst preparations at high loading (Strain IC2 $OD_{600}$=40 or equivalent 0.6 mg $mL^{-1}$ purified LsLAI) in batch processes starting with 300 mM galactose. Consistent with our initial experiments, the pure enzyme preparation was limited to 39±2.3% conversion after 48 h at 37° C. (FIG. 4). Increasing the temperature of the reaction to 50° C. allowed for high initial production of tagatose; however, the enzyme denatured quickly reaching a maximum conversion of only 16±2.8%. Bacterial encapsulation of LsLAI (IC2+ PBS) produced 47±3.3% tagatose at 37° C., improvement over the pure-enzyme system. Encapsulation also provided thermal stability to the enzyme allowing for sustained activity at 50° C. increasing both the rate of production (46±2.3% in 6 h) and equilibrium conversion (83±6.1%) compared to unmodified whole-cell catalyst at 37° C. Rate of production was further increased by modifying the whole-cell catalyst through SDS permeabilization (IC2+SDS) to achieve 59±3.5% conversion in 6 h, ultimately reaching a similar equilibrium conversion of 85±6.7% as unpermeabilized cells. Thus, permeabilized, cell-encapsulated LAI overcomes the three reaction limitations by supporting greater thermal stability, higher equilibrium conversion, and faster reaction rates than possible by a free enzyme system.

To investigate the potential to increase the average productivity of our system, we increased the substrate level from 300 mM to 600 mM and 1 M galactose and measured the production of tagatose using permeabilized L. plantarum encapsulating L. sakei LAI (strain IC2+SDS) over the course of 24 h. Higher substrate loading lowered the final conversion of the system to 47% and 39% at 600 mM and 1 M galactose respectively (FIG. 12). We observed high productivities initially, when conversions are low, as expected. After 6 hours, the average productivity of our system was 9.3 g $L^{-1}$ $h^{-1}$ of tagatose starting from 1 M galactose substrate loading compared to 5.3 g $L^{-1}$ $h^{-1}$ starting from 300 mM galactose. Based on these results, increasing the substrate loading increased average productivity at the cost of conversion, which is consistent with many previous studies[18,35,36].

DISCUSSION

While an increasing number of enzymes are being used for biocatalysis, poor stability under reaction conditions, and unfavorable kinetic properties toward non-native substrates can limit their utility toward biosynthetic functions. Further, for certain classes of enzymes like isomerases, transglycosidases, and lyases, limitations of endergonic or mild exergonic thermodynamics are additional hurdles to economical processes. D-Tagatose synthesis from D-galactose using the enzyme LAI (L-arabinose isomerase) suffers from all three of these limitations. Our results confirm the presence of all three limitations (stability, thermodynamic, kinetic) during enzymatic conversion of galactose to tagatose using the acid-tolerant mesophilic LAI from Lactobacillus sakei (LsLAI). At low temperatures (37° C.), the enzyme is stable and quickly reaches equilibrium. However, the product titer is low due to low equilibrium conversion (36-39%) at low temperatures (this study and previously reported[32]). At elevated temperatures (50° C.), the initial reaction rates are faster, but the enzyme quickly inactivates and is unable to realize the higher conversion and product titer possible at this temperature. These limitations of LAI for tagatose synthesis have been realized previously, and each issue has been addressed individually. While some successes have been reported, especially by selecting or engineering enzymes with more desirable properties[4,10,11,37,38], this study addresses and overcomes all three issues simultaneously.

LAI display on Bacillus subtilis endospore surface was shown to improve thermostability while maintaining free enzyme-like kinetic properties[18]. Therefore, this approach addresses the stability limitations but not the thermodynamic issue. To assess whether cell surface display on L. plantarum could improve stability of LsLAI, we tested six previously reported anchor proteins and found there was no correlation linking whole-cell activity and surface display level/accessibility. We showed evidence for presence of cytoplasmic LsLAI-anchor fusions and concluded that enzymatic activity seen was largely due to this active fraction and that the enzyme displayed on the surface was largely inactive. When we tested secretion constructs (i.e., LsLAI with secretion signal but no anchor), we found similar results, suggesting that LsLAI cannot fold extracellularly upon secretion through this pathway and that active enzyme accumulated cytoplasmically. This is surprising since there is no precedence for such an observation in literature. L. plantarum utilizes the Sec-pathway to secrete proteins[39] and it is generally accepted that translocation occurs co-translationally[40,41]; therefore, for a protein to be active it must fold properly in the extracellular environment. While we detected LsLAI on the surface using flow cytometry and Western blot analysis, we could not correlate display level to activity or subsequently attribute any detectable activity to the displayed protein at all. Our results suggest the need to be cautious when attributing activity of surface displayed proteins, even if they are readily detected. There are other reports of surface displayed enzymes or antigens have shown lack of correlation between surface detection and activity both in-vitro and in-vivo[42-44]. We suggest future studies to more directly attribute activity to displayed proteins and not due to presence of active cytoplasmic proteins in whole or lysed cells. We posit that overexpression of surface directed proteins may yield a back-up resulting in translation of active protein fusions directly in the cytoplasm. Surface display of LsLAI has been shown before with B. subtilis endospores; however, the construct is assembled on the spore cytoplasmically[18], without the need for any secretion. Our results contradict reports from another study that claimed secretion of active LsLAI using Lactococcus lactis[1]. However, closer analysis of the study revealed that measured activity was never attributed directly to culture supernatant. Rather activity was detected either for whole cells or in the elution fraction post-chromatographic purification, which could have allowed for refolding to occur. Thus, we posit that cell-surface display is not a viable option to improve the stability of this enzyme.

Cellular or abiotic encapsulation has shown to improve enzyme stability against thermal, pH, solvent, and impurity interactions[23,45] In the context of tagatose production, whole cells expressing L-AI has also shown to improve conversion by preferentially partitioning substrate and product across the E. coli membrane barrier through active transport[25]; however, the same was not observed in resting L. lactis cells[46]. Our results demonstrate that encapsulation of LAI in L. plantarum behaves in a manner similar to that in Gram-negative E. coli but not Gram-positive L. lactis. That is, the cell membrane preferentially allows passage of galactose to the intracellular space relative to tagatose to aid the forward reaction. A concurrent advantage of the encapsulation was that the enzyme stability was markedly improved. Specifically, while the free enzyme rapidly inactivates at 50° C., the cell-encapsulated enzyme maintains activity for a prolonged period. Indeed, the resistance to lysis at elevated temperatures is afforded by the thick cell wall of the Gram-positive L. plantarum, as opposed to Gram-negative E. coli, which is known to readily lyse at 50° C.[47]. Thus, while many previous studies have demonstrated the benefits of using whole cells to enhance enzyme stability, this work shows the twofold benefit by combining improved stability with substrate-product partitioning. While the selective membrane circumvents the thermodynamic barrier that limits maximum conversion at moderate temperatures, it imposes a barrier to mass transport—a penalty to reaction kinetics. We addressed this issue next.

Cell permeabilization using chemical agents like detergents or solvents have been shown to non-selectively increase substrate exchange while maintaining biological cellular components[48,49], although the exact mechanism of this phenomenon is poorly understood. We used detergents to improve reactant/product transport across the L. plantarum cell membrane without altering its selectivity. In our best-case scenario, sub-micellar concentration of SDS resulted in significant increase in whole cell reaction rates to free-enzyme-like rates while still allowing the system to circumvent the thermodynamic barrier to product conversion. Since the conversion was unchanged, we presume that the detergents were not making pores in the cell membrane. Transmission electron microscopy of SDS-treated L. plantarum cells found no evidence of pore formation or leakage of cytoplasmic biological components (FIG. 13). L. plantarum cells treated with 0.01% SDS under the optimized enzyme assay conditions retained their cytoplasmic membranes. Interestingly, permeabilization increased the initial reaction rate in the forward direction 3.8-fold, however the rate of the reverse reaction remained low, indicating that the membrane retained its selectivity (FIG. 7). Studies with cFDA further confirmed that cytoplasmic components were not leaking into the extracellular space and that the cellular integrity was maintained. Thus, substrate and product transport were still likely facilitated through transporters, as in untreated cells, which is also consistent with the observation that glucose inhibits only whole cell reactions (but not that of free enzyme) and conversion reaches the same maximum with or without detergent treatment. Since SDS and Triton-X treatment resulted similar outcomes, we believe there are no specific charge-related effects of these detergents, either. Adding SDS to a pure enzyme solution did not alter its kinetic properties, indicating that the detergents do not directly interact with the enzyme in any appreciable manner. However, our study revealed that treatment with SDS removed extracellular- and surface-attached proteins, potentially altering the fluidity of the membrane and/or permeability of the cell wall. The latter is supported by the fact lysozyme treatment also increases reaction rates, suggesting that the thick Gram-positive peptidoglycan poses a transport barrier.

Having addressed all three limitations (stability, thermodynamics, kinetics), we found that L. plantarum whole-cell biocatalyst achieved a conversion from of ~50% in 4 h and ~85% 48 h in batch process at 50° C. starting with 300 mM galactose. Improved stability is apparent by comparison with the free enzyme system, which quickly inactivates at 50° C. and achieves only 16% conversion in 48 h. Enhanced equilibrium conversion compared to free enzyme system can be seen at both 50° C. and 37° C., but especially in the latter, where the free enzyme is more stable but is still able to achieve only 13% conversion in 4 h and 47% in 48 h. Finally, improved kinetics can be seen compared to unpermeabilized cells where initial reaction rates at 0.5 mM min$^{-1}$ compared to 1.6 mM min$^{-1}$ in permeabilized cells. This rate is higher than the maximum reaction rates sustainable by the free enzyme for extendable period (initial rate at 37° C. for free enzyme=0.3 mM h$^{-1}$) due to the ability to operate at 50° C. Thus, this cellular encapsulation system enables higher average productivity (5.3 g L$^{-1}$ h$^{-1}$ after 6 h) and higher conversion (~85%) than possible by the purified, free enzyme. Average productivity of the modified cell encapsulated LAI batch process could be improved by increasing the initial concentration of galactose from 300 mM to 1 M, albeit with lower conversion. Although further improvements to conversion may be possible by including borate in the reaction buffer, demonstrated previously, it would also increase purification costs[16,26,46] Further, this system nearly matches the conversion obtained in a recent study with a extremophilic LAI at 95° C. and pH 9.5 that required use of Ni$^{2+}$ and borate[50] but at 50° C. and without use of toxic metals and salts. Additionally, the system avoids product caramelization, which is known to happen at high temperatures (≥80° C.)[17]. Thus, the system described here demonstrates how to overcome three major limitations of enzymatic catalysis (stability, thermodynamic, kinetic) for tagatose production using LAI. We believe that a similar strategy may be applicable to other biocatalytic systems as well—particularly lyases[51], transglycosidases[52], isomerases[12,25,35,53], and epimerases[54]—where free enzyme performance is poor due to stability, thermodynamic, and/or kinetic limitations.

Methods

Reagents and enzymes. All enzymes for cloning were purchased from NEB (Beverly, Mass.). DNA primers were ordered from Eurofins Genomics LLC (Louisville, Ky.) or GENEWIZ Inc. (Cambridge, Mass.). Growth media and chemicals were purchased from Amresco (Solon, Ohio) or RPI Corp (Mount Prospect, Ill.). High-purity L-arabinose and D-galactose were purchased from Sigma-Aldrich (St. Louis, Mo.). Plasmid Mini Kit I, PCR Purification and Gel Extraction Kits were obtained from Omega Bio-tek (Norcross, Ga.). Mouse-anti-His6 primary antibody (MA1-21315) and goat anti-mouse IgG H&L (Alexa Fluor® 488) (A1101) were purchased from Thermo Fisher Scientific (Waltham, Mass.).

Bacterial strains and culture conditions. *Lactobacillus plantarum* WCFS1 (kind gift from Prof Michiel Kleerebezem, Wageningen University & Research) was cultivated in deMan-Rogosa-Sharpe (MRS) medium at 30° C. without agitation. *E. coli* strain NEB5a (New England Biolabs, Ipswich, Mass., USA) was grown in Luria-Bertani (LB) medium at 37° C. with shaking at 225 rpm. When needed, media were supplemented with erythromycin at concentrations of 5 μg mL$^{-1}$ and 200 μg mL$^{-1}$ for *L. plantarum* and *E. coli*, respectively. Solid media were prepared by adding 1.5% (w/v) agar to the respective media.

Plasmid and strain construction. DNA amplification was performed with Phusion High-Fidelity DNA Polymerase according to the manufacturer's instructions. *E. coli* was used as host for plasmid propagation before transformation into *L. plantarum*. The amplified sequences were verified by a commercial sequencing service (GeneWiz). All strains and plasmids used in this study are listed in Table 2 and Table 3.

*L. plantarum* surface display plasmids were constructed based on the previously published pSIP401 based plasmid pLp_3050Ag85B-E6cwa2 (Table 2). The LAI gene from *L. sakei* 23K was synthesized by Twist Biosciences. This gene was subsequently cloned using primer pair oJRB133 and oJRB134 and inserted into pLp_3050Ag85B-E6cwa2 using BfaI and HindIII restriction sites to create plasmid pJRB01Q-LSH. pJRB02Q-LSH was created via was the amplification of Lp_2162 from the *L. plantarum* chromosome using primer pair oJRB10 and oJRB11 and inserted into pJRB01Q-LSH using MluI and HindIII restrictions sites. pJRB03Q-LSH was created via was the amplification of Lp_2940 from the *L. plantarum* chromosome using primer pair oJRB20 and oJRB21 and inserted into pJRB01Q-LSH using MluI and HindIII restrictions sites. pJRB05Q-LSH was created via the amplification of Lp 1261 from the plasmid pLp_1261Ag85B-E6 (Table 2) using primer pair oJRB7 and oJRB8 before being overlapped with *L. sakei* LAI and inserted into pJRB01Q-LSH using SalI and PmlI restriction sites. pJRB06Q-LSH was created via amplification of Lp 1452 from the *L. plantarum* chromosome using primer pair oJRB14 and oJRB15 and inserted into pJRB05Q-LSH using SalI and PmlI restrictions sites. pJRB08Q-LSH was created via the amplification of Lp 3014 from the *L. plantarum* chromosome using primer pair oJRB82 and oJRB83 and inserted into pJRB05Q-LSH using SalI and PmlI restrictions sites. pJRB04Q-LSH was created via amplification of the *L. sakei* LAI gene using primer pair oJRB170 and oJRB171 and inserted into pJRB01Q-LSH using NdeI and HindIII restriction sites. pJRB09Q-LSH was created via amplification of the *L. sakei* LAI gene using primer pair oJRB304 and oJRB305 and inserted into pJRB01Q-LSH using SalI and PmlI restriction sites. Plasmid pJRB14Q-LSH was created via amplification of the *L. sakei* LAI gene and 6×-His tag using primer pair oJRB457 and oJRB458 and inserted into pSIP411 (Table 2) using NcoI and HindIII restriction sites.

Each plasmid was transformed into chemically competent *E. coli* NEB5a cells according to the manufacturer's instructions. *L. plantarum* was transformed using a previously described electroporation method[55] with slight modifications. Briefly, stationary phase cells were subcultured to an $OD_{600}$=0.1 in MRS and allowed to grow until an $OD_{600}$=0.85. Cells were harvested via centrifugation at 4° C. and washed twice in ice-cold 10 mM $MgCl_2$ and once with 0.5 M sucrose and 10% glycerol. Cells were resuspended in 1:50 (v/v) of the same solution and kept on ice prior to transformation. 100 ng of plasmid DNA was diluted into 5 μL of water and mixed with 50 μL electrocompetent cells immediately before adding to a chilled 1 mM electroporation cuvette. The bacteria were transformed using a BioRad Pulser at 1300 V with a fixed time constant of 5 ms. 1 mL of warm MRS was added and the cells transferred to a new centrifuge tube and allowed to recover statically at 37° C. for 3 h before plating on appropriate media containing selective antibiotic. Positive transformants were confirmed using colony PCR.

Enzyme purification. *L. plantarum* cells carrying pJRB14Q-LSH were washed in lysis/equilibration buffer (50 mM sodium phosphate, 300 mM sodium chloride, 15% glycerol, pH 8.0) and resuspended in lysis buffer containing 10 mM lysozyme and incubated at 37° C. with shaking for one hour. Lysis was achieved via sonication and soluble protein collected. Purification was achieved via immobilized metal affinity chromatography (IMAC) using an N-terminal His6 tag. TALON metal affinity resin (Invitrogen) was used as directed by the manufacturer. A single elution of protein was achieved in elution buffer containing 500 mM imidazole. Active fractions were pooled, and the buffer exchanged with PBS containing 1 mM $MgCl_2$ (PBSM) using a Microsep 10 kDa Omega centrifugation spin column (PALL Corp; Port Washington, N.Y.). Purification was confirmed via SD-PAGE analysis. Purified enzyme was stored in PBSM with 20% glycerol at −80° C. prior to use.

Enzyme analysis. *L. plantarum* wild-type (WT) cells or those carrying plasmids pJRB01Q-LSH (A1), pJRB02Q-LSH (A2), pJRB03Q-LSH (A3), pJRB04Q-LSH (IC1), pJRB05Q-LSH (A4), pJRB06Q-LSH (A5), pJRB08Q-LSH (A6) were cultured in MRS media with antibiotic as needed at 37° C. overnight. Overnight cultures were diluted 1:50 (approximate $OD_{600}$=0.1) in MRS media with antibiotic as needed and grown at 37° C. for 2.5 h. Cells were then induced with IP-673 (synthesized by Life Technologies; Carlsbad, Calif.) at a final concentration of 25 ng mL$^{-1}$ and $MgCl_2$ was added to a final concentration of 1 mM to support enzyme folding. Cultures were incubated at 37° C. for an additional 3 h before harvesting the cells by centrifugation at 3000×g for 5 min.

Cell pellets were washed in 1 mL of 20 mM phosphate buffer (PB) pH 6.8 and transferred to a 1.7 mL centrifuge tube. Cells were washed twice with 1 mL of PB before being suspended in 200 μL PB buffer. The enzyme activity assay was performed in a 96-well plate as follows: 20 μL cell suspension was incubated with 0.8 mM $MnCl_2$, 0.8 mM $MgCl_2$, sugar (200 mM galactose or 200 mM glucose) and diluted to 200 μL with PB. The cell density within each well was measured for data normalization at the start of the reaction. The plates were sealed and incubated at 37° C. for 2 h. Enzyme activity was measured colorimetrically using the cysteine-carbazole-sulfuric-acid method (CCSAA)[56]. Absorbance at 560 nm was measured after 1 h of incubation at room temperature. Triplicate technical replicates of each cell suspension were analyzed and averaged due to variability in the assay itself.

To determine the conversion achieved with our balanced system, L. plantarum cells carrying pJRB14Q-LSH (IC2) and wild-type were grown and induced with 25 ng $mL^{-1}$ IP-673 for 8 h instead of 3 h to maximize the cell density of the culture. Cells were harvested via centrifugation and washed twice in phosphate-buffered saline pH 7.4 with 1.0 mM $MgCl_2$ (PBSM). Cells to be permeabilized were diluted to an $OD_{600}$=3.0 before incubation with 0.01% SDS in PBSM for 30 min at room temperature. The enzyme activity assay was performed in 5 mL tubes as follows: cell suspensions adjusted to an $OD_{600}$=40 were incubated in phosphate-buffered saline (PBS) pH 7.4 with 1.0 mM $MgCl_2$, 300 mM galactose and adjusted to 5 mL with $H_2O$. The conversion and productivity at increasing concentrations of galactose was performed by increasing the substrate concentration to 600 mM or 1 M with the same assay conditions.

Initial rates of reaction for both pure-enzyme, unmodified, and modified whole-cell catalysts were determined. L. plantarum cells carrying pJRB14Q-LSH were grown and induced for 8 h. The enzyme activity assay was performed in 200 μL PCR tubes as follows: purified enzyme or cell suspensions were incubated in PBSM, variable substrate concentration of galactose or tagatose, and adjusted to 100 μl with $H_2O$. Reactions were initiated by adding $\frac{1}{10}^{th}$ volume cell suspensions adjusted to an $OD_{600}$=10 or 2 μg of purified enzyme to prewarmed reaction mixtures in a PCR block at either 37 or 50° C. Reactions proceeded for 6 min before termination to measure initial reaction rates. Cell suspensions were immediately centrifuged for 1 min using a benchtop quick-spin centrifuge and the supernatant was transferred to a 96-well 0.2 μm centrifugal filter plate with collection plate. The remaining solution was filtered via centrifugation and stored at −80 C until analysis. Purified enzyme reactions were terminated by adding $\frac{1}{10}^{th}$ volume 2M perchloric acid. Prior to HPLC analysis the reactions were neutralized using a sodium hydroxide PBS buffered solution. $k_{initial}$ is defined as the initial reaction rate of each catalyst at a given, non-saturating substrate concentration and stopped the reaction prior to 10% total conversion.

Enzyme stability was measured by incubating either purified enzyme or unmodified whole cell catalysts in PBSM at 37 or 50° C. statically for the duration of the experiment. At determined time intervals and aliquot of catalyst was added to PBSM reaction mixture containing 300 mM galactose at the same temperature as the catalyst. Reactions proceeded for 20 min before termination. Tagatose production was confirmed via HPLC analysis.

Equilibrium conversion was measured by in incubating either purified enzyme or unmodified whole cell catalysts in PBSM at 37° C. Purified enzyme was incubated with either 10 mM galactose, 5 mM of galactose and tagatose, or 10 mM tagatose. The reaction was sampled every 24 h and additional enzyme was added after sampling due to incomplete reaction due to enzyme degradation. Whole cell catalyst was incubated with either 30 mM galactose, 15 mM of galactose and tagatose, or 30 mM tagatose.

The selectivity of the L. plantarum cell barrier was tested by comparing the inhibition of the transport of galactose compared to that of the pure enzyme. L. plantarum strain IC2 carrying pJRB14Q-LSH was grown and induced for 8 h. L. plantarum encapsulating LAI (IC2) or purified LAI (PURE) was added to reaction mixture containing and incubated at 37° C. Reactions proceeded for 20 min before termination.

HPLC analysis. Agilent Infinity HPLC system (Agilent; Santa Clara, Calif.) equipped with a Hi-Plex Ca+ 300×7.7 mm column with a guard column and detected using Agilent Infinity 1260 ELSD detector. The mobile phase was filtered deionized water run at 85° C. with a flow rate of 0.6 mL $min^{-1}$. The ELSD detector's evaporation temperature was set at 90° C., the nebulizer temperature set to 50° C., and nitrogen flow rate at 1.6 SLM (standard liter per minute). For calculation of the reaction product(s) L-arabinose, D-galactose, L-ribulose, and D-tagatose standards were included in the run.

Flow cytometry and immunostaining. L. plantarum WT cells or those carrying plasmids pJRB01QLs-pJRB08QLs were grown and induced. Cells were collected by centrifugation at 5000×g for 5 min and washed twice in PBS before being suspended to an $OD_{600}$=1.0. An aliquot of 200 μL cells was pelleted and was resuspended in 200 μL PBSA (PBS with 2% bovine serum albumin). The suspension of cells rested on ice for 30 min before the cells were pelleted and solution removed. The cells were then resuspended in 50 uL of PBSA containing 1 μg mouse-anti-His6 primary antibody (1:500 dilution). The cells were incubated for 1 h at room temperature with gentle rocking. Cells were collected and washed thrice with PBSA before being suspended in 50 μL of PBSA containing 0.4 μg goat anti-mouse IgG H&L (Alexa Fluor® 488) (1:250 dilution). The cells were incubated for one fifteen minutes on ice and blocked from light. Finally, cells were washed thrice in PBSA and resuspended in 500 ul of PBSA. A 20 ul aliquot was diluted 10× in PBSA and transferred to a flat-bottom 96-well plate for flow cytometric analysis. A positive control sample was used to calibrate the fluorescence intensity. A negative control sample was used to gate the level of autofluorescence of the cells and any non-specific secondary antibody binding (FIG. 14). A total of $1\times10^5$ cell counts per sample plotted on a logical or bi-exponential x-axis. Data analyzed using FCS Express 6 (De Novo Software, Glendale, Calif.). Surface detection level was calculated as the fraction of cells with a measured fluorescence greater than that of the gated negative control.

Surface treatment. L. plantarum WT cells or those carrying either pJRB04Q-LSH or pJRB08Q-LSH were grown and induced as previously described. Cells were washed in PBS twice before further processing. A concentrated cell solution was incubated in PBS containing either 0% or 0.5% SDS for 1 h before being pelleted by centrifugation. The SDS solution was removed and the cell pellet washed twice with PBS. Surface detection was measured via immunofluorescence flow cytometry. Whole-cell activity was measured via the CCSAA after a 1-hour incubation in 200 mM arabinose and 1 mM $MgCl_2$ in 100 mM sodium acetate buffer pH 5.0 at 37° C.

Western blot analysis. L. plantarum WT cells or those carrying either pJRB04Q-LSH or pJRB08Q-LSH were grown and induced as previously described. A concentrated cell solution was incubated with 0.05 SDS in PBS for 30 min at 37° C. before being pelleted. The SDS buffer solution was removed and stored separately. The cell pellet was then washed twice with PBS. A fresh cell solution of the same concentration was prepared in PBS as a control. Both aliquots of cells were then incubated with 10 mg mL$^{-1}$ lysozyme for 1 h at 37° C. before being lysed via sonication. Sonication was performed using a Branson 150 system equipped with a microtip probe sonicating samples on ice at 55% amplitude in 30 s ON 2 min OFF cycles for a total of 5 min of ON time. The insoluble cell fraction containing membrane components and the insoluble protein fraction was pelleted via centrifugation at 20,000×g for 5 min. The soluble fraction was removed, filtered through 0.4 µm sterile filter, and stored separately. An aliquot of each of the cell fractions for the three cell types was added to denaturing loading dye and incubated at 98° C. for 15 min. 10 µL of each sample were added to a 4%-12% Bis-Tris PAGE gel in MOPS buffer and run at 75 V for 15 min followed by 110 V for 1.5 h. After separation the gel was removed from the cassette and washed twice in deionized water. The proteins were next transferred to a PVDF membrane for Western blot analysis. Transfer was visually confirmed through the transfer of the stained protein ladder. The membrane was blocked overnight at room temperature with 5% skim milk in Tris buffered saline containing 1% Tween-20 (TBST). The membrane was washed twice with TBST before being incubated with 0.2 µg mL$^{-1}$ primary antibody in blocking buffer for 2 h at room temperature. The membrane was washed twice with TBST before being incubated with 2 ng mL$^{-1}$ of the horseradish peroxidase (HRP) conjugated secondary antibody at room temperature for 1 h. The membrane was then washed twice with TBST before incubation in the substrate containing solution (Thermo SuperSignal West) for 15 min at room temperature. The chemiluminescent signal was captured electronically via a camera set to a 30 min exposure time.

Cell permeabilization. L. plantarum WT cells or those carrying pJRB14Q-LSH (IC2) were grown and induced and washed in PBS as previously described. Cells were resuspended to an $OD_{600}$=3.0 in 200 µL of PBS. Samples were either incubated with 1% Triton X-100$^{27}$, 0.1% SDS, 0.1 µM chicken egg lysozyme, or no treatment at room temperature for 1 h. The solution was removed, and the cell pellet washed twice with PBS before enzymatic activity of the whole-cells were measured using 200 mM galactose in PBS pH 7.4 containing 1 mM $MgCl_2$. Activity was quantified via the CCSAA and normalized to cell concentration.

The optimal concentration of SDS to maximize whole-cell activity was determined. Cells were prepared as previously described. Cell lysate from the equivalent cell density was prepared via lysozyme treatment followed by sonication. Permeabilized samples were either incubated with varying concentrations of SDS, or no treatment at room temperature for 30 min. The solution was removed and the cell pellet was washed twice with PBS before measuring enzymatic activity of the whole-cells using 200 mM galactose. Activity was quantified via the CCSAA and normalized to cell concentration.

Cell permeabilization was also tested using carboxyfluorescein diacetate (cFDA) (Sigma-Aldrich) as substrate. Cell suspensions were diluted to $OD_{600}$=0.5 in PBS in a black polystyrene 96-well plate. The reaction was started by adding 10 mM cFDA to the cell suspensions. Transport of cFDA was estimated by measuring the fluorescent signal released when cFDA becomes activated upon intracellular cleavage via nonspecific esterases. The total fluorescence was measured on a plate-reader using an excitation and emission wavelength of 485 nm and 520 nm, respectively, every 15 s for 30 min. Apparent transport rates were calculated from the slope of the linear fit to the data.

Electron microscopy. The cells were fixed in 2.5% gluteraldehyde, 3% paraformaldehyde with 5% sucrose in 0.1 M sodium cacodylate buffer (pH 7.4), pelleted, and post fixed in 1% $OsO_4$ in veronal-acetate buffer. The cells were stained en block overnight with 0.5% uranyl acetate in veronal-acetate buffer (pH 6.0), then dehydrated and embedded in Embed-812 resin. Sections were cut on a Leica EM UC7 ultra microtome with a Diatome diamond knife at a thickness setting of 50 nm, stained with 2% uranyl acetate, and lead citrate. The sections were examined using a FEI Tecnai spirit at 80 KV and photographed with an AMT ccd camera.

Statistics and data reproducibility. All the experiments were conducted using biological replicates and were carried on different days as specified to calculate measure of variability between the samples. All the data shown are mean with error bars representing standard deviation.

REFERENCES

1. Rhimi, M. et al. The secreted l-arabinose isomerase displays anti-hyperglycemic effects in mice. Microb. Cell Fact. 14, 204 (2015).
2. Luecke, K. J. & Bell, L. N. Thermal stability of tagatose in solution. J. Food Sci. 75, C346-51 (2010).
3. Bertelsen, H., Andersen, H. & Tvede, M. Fermentation of D-tagatose by human intestinal bacteria and dairy lactic acid bacteria. Microb. Ecol. Health Dis. 13, 87-95 (2001).
4. Xu, Z., Li, S., Feng, X., Liang, J. & Xu, H. L-Arabinose isomerase and its use for biotechnological production of rare sugars. Appl. Microbiol. Biotechnol. 98, 8869-8878 (2014).
5. Cheetham, P. S. J. & Wootton, A. N. Bioconversion of D-galactose into D-tagatose. Enzyme Microb. Technol. 15, 105-108 (1993).
6. Xu, W., Zhang, W., Zhang, T., Jiang, B. & Mu, W. L-arabinose isomerases: Characteristics, modification, and application. Trends in Food Science and Technology 78, 25-33 (2018).
7. Xu, Z. et al. A novel L-arabinose isomerase from Lactobacillus fermentum CGMCC2921 for D-tagatose production: Gene cloning, purification and characterization. J. Mol. Catal. B Enzym. 70, 1-7 (2011).
8. Waltman, M. J., Yang, Z. K., Langan, P., Graham, D. E. & Kovalevsky, A. Engineering acidic Streptomyces rubiginosus D-xylose isomerase by rational enzyme design. Protein Eng. Des. Sel. 27, 59-64 (2014).
9. Zheng, Z., Mei, W., Xia, M., He, Q. & Ouyang, J. Rational design of Bacillus coagulans NL01 L-arabinose isomerase and use of its F2791 variant in D-tagatose production. J. Agric. Food Chem. 65, 4715-4721 (2017).
10. Fan, C. et al. Engineering of Alicyclobacillus hesperidum L-arabinose isomerase for improved catalytic activity and reduced pH optimum using random and site-directed mutagenesis. Appl. Biochem. Biotechnol. 177, 1480-1492 (2015).
11. Oh, H. J., Kim, H. J. & Oh, D. K. Increase in D-tagatose production rate by site-directed mutagenesis of L-arabinose isomerase from Geobacillus thermodenitrificans. Biotechnol. Lett. 28, 145-149 (2006).
12. Hong, Y.-H. H., Lee, D.-W. W., Pyun, Y.-R. R. & Lee, S. H. Creation of metal-independent hyperthermophilic L-arabinose isomerase by homologous recombination. J. Agric. Food Chem. 59, 12939-12947 (2011).

13. Prabhu, P., Jeya, M. & Lee, J. K. Probing the molecular determinant for the catalytic efficiency of L-arabinose isomerase from *Bacillus licheniformis*. Appl. Environ. Microbiol. 76, 1653-1660 (2010).
14. Choi, J. M. et al. Structure of the thermophilic L-arabinose isomerase from *Geobacillus kaustophilus* reveals metal-mediated intersubunit interactions for activity and thermostability. Arch. Biochem. Biophys. 596, 51-62 (2016).
15. Kim, H. J. & Oh, D. K. Purification and characterization of an L-arabinose isomerase from an isolated strain of *Geobacillus thermodenitrificans* producing D-tagatose. J. Biotechnol. 120, 162-173 (2005).
16. Li, Y., Zhu, Y., Liu, A. & Sun, Y. Identification and characterization of a novel L-arabinose isomerase from Anoxybacillus flavithermus useful in D-tagatose production. Extremophiles 15, 441-450 (2011).
17. Kwon, S. Y. & Baek, H. H. Effects of temperature, pH, organic acids, and sulfites on tagatose browning in solutions during processing and storage. Food Sci. Biotechnol. 23, 677-684 (2014).
18. Liu, Y. et al. Efficient production of D-tagatose using a food-grade surface display system. J. Agric. Food Chem. 62, 6756-62 (2014).
19. Zhang, Y. W., Jeya, M. & Lee, J. K. Enhanced activity and stability of L-arabinose isomerase by immobilization on aminopropyl glass. Appl. Microbiol. Biotechnol. 89, 1435-1442 (2011).
20. Bortone, N. & Fidaleo, M. Immobilization of the recombinant (His)6-tagged l-arabinose isomerase from *Thermotoga maritima* on epoxy and cupper-chelate epoxy supports. Food Bioprod. Process. 95, 155-162 (2015).
21. Kim, P., Yoon, S. H., Roh, H. J. & Choi, J. H. High production of D-tagatose, a potential sugar substitute, using immobilized L-arabinose isomerase. Biotechnol. Prog. 17, 208-210 (2001).
22. Hong, Y. H. et al. Production of D-tagatose at high temperatures using immobilized *Escherichia coli* cells expressing L-arabinose isomerase from *Thermotoga neapolitana*. Biotechnol. Lett. 29, 569-574 (2007).
23. Lin, B. & Tao, Y. Whole-cell biocatalysts by design. Microbial Cell Factories 16, 106 (2017).
24. Liu, J.-J. et al. Overcoming the thermodynamic equilibrium of an isomerization reaction through oxidoreductive reactions for biotransformation. Nat. Commun. 10, 1-8 (2019).
25. Kim, J. H. et al. Differential selectivity of the *Escherichia coli* cell membrane shifts the equilibrium for the enzyme-catalyzed isomerization of galactose to tagatose. Appl. Environ. Microbiol. 74, 2307-2313 (2008).
26. Xu, Z. et al. Production of D-tagatose, a functional sweetener, utilizing alginate immobilized *Lactobacillus fermentum* CGMCC2921 cells. Appl. Biochem. Biotechnol. 166, 961-73 (2012).
27. Jayamuthunagai, J., Srisowmeya, G., Chakravarthy, M. & Gautam, P. d-Tagatose production by permeabilized and immobilized *Lactobacillus plantarum* using whey permeate. Bioresour. Technol. 235, 250-255 (2017).
28. Apel, A. R., Ouellet, M., Szmidt-Middleton, H., Keasling, J. D. & Mukhopadhyay, A. Evolved hexose transporter enhances xylose uptake and glucose/xylose co-utilization in *Saccharomyces cerevisiae*. Sci. Rep. 6, 19512 (2016).
29. Miskovic, L. et al. A design-build-test cycle using modeling and experiments reveals interdependencies between upper glycolysis and xylose uptake in recombinant *S. cerevisiae* and improves predictive capabilities of large-scale kinetic models. Biotechnol. Biofuels 10, 166 (2017).
30. Bober, J. R., Beisel, C. L. & Nair, N. U. Synthetic biology approaches to engineer probiotics and members of the human microbiota for biomedical applications. Annu. Rev. Biomed. Eng. 20, 277-300 (2018).
31. Mays, Z. J. & Nair, N. U. Synthetic biology in probiotic lactic acid bacteria: At the frontier of living therapeutics. Curr. Opin. Biotechnol. 53, 224-231 (2018).
32. Rhimi, M. et al. The acid tolerant L-arabinose isomerase from the food grade *Lactobacillus sakei* 23K is an attractive D-tagatose producer. Bioresour. Technol. 101, 9171-9177 (2010).
33. Mukerjee, P. & Mysels, K. J. Critical micelle concentrations of aqueous surfactant systems. J. Pharm. Sci. 61, 319 (1972).
34. Tao, F., Zhang, Y., Ma, C. & Xu, P. One-pot biosynthesis: N-acetyl-D-neuraminic acid production by a powerful engineered whole-cell catalyst. Sci. Rep. 1, 142 (2011).
35. Guo, Q. et al. Enhanced D-tagatose production by spore surface-displayed L-arabinose isomerase from isolated *Lactobacillus brevis* PC16 and biotransformation. Bioresour. Technol. 247, 940-946 (2018).
36. Mei, W., Wang, L., Zang, Y., Zheng, Z. & Ouyang, J. Characterization of an L-arabinose isomerase from *Bacillus coagulans* NL01 and its application for D-tagatose production. BMC Biotechnol. 16, 1-11 (2016).
37. Rhimi, M. et al. Rational design of *Bacillus stearothermophilus* US100 L-arabinose isomerase: Potential applications for D-tagatose production. Biochimie 91, 650-653 (2009).
38. Kim, B. J., Hong, S. H., Shin, K. C., Jo, Y. S. & Oh, D. K. Characterization of a F280N variant of L-arabinose isomerase from *Geobacillus thermodenitrificans* identified as a D-galactose isomerase. Appl. Microbiol. Biotechnol. 9271-9281 (2014). doi:10.1007/s00253-014-5827-z
39. Brurberg, M. et al. Genome-wide analysis of signal peptide functionality in *Lactobacillus plantarum* WCFS1. BMC Genomics 10, 425 (2009).
40. Schneewind, O. & Missiakas, D. Sec-secretion and sortase-mediated anchoring of proteins in Gram-positive bacteria. Biochim. Biophys. Acta 1843, 1687-1697 (2014).
41. Mori, H. & Ito, K. The Sec protein-translocation pathway. Trends Microbiol. 9, 494-500 (2001).
42. Nguyen, H.-M. et al. Display of a β-mannanase and a chitosanase on the cell surface of *Lactobacillus plantarum* towards the development of whole-cell biocatalysts. Microb. Cell Fact. 15, 169 (2016).
43. Kuczkowska, K. et al. Immunogenic properties of *Lactobacillus plantarum* producing surface-displayed *Mycobacterium tuberculosis* antigens. Appl. Environ. Microbiol. 83, e02782-16 (2017).
44. Kuczkowska, K., Mathiesen, G., Eij sink, V. G. H. & Øynebråten, I. *Lactobacillus plantarum* displaying CCL3 chemokine in fusion with HIV-1 Gag derived antigen causes increased recruitment of T cells. Microb. Cell Fact. 14, 1 (2015).
45. Mohamad, N. R., Marzuki, N. H. C., Buang, N. A., Huyop, F. & Wahab, R. A. An overview of technologies for immobilization of enzymes and surface analysis techniques for immobilized enzymes. Biotechnol. Biotechnol. Equip. 29, 205-220 (2015).

46. Salonen, N., Salonen, K., Leisola, M. & Nyyssola, A. D-Tagatose production in the presence of borate by resting *Lactococcus lactis* cells harboring *Bifidobacterium longum* L-arabinose isomerase. Bioprocess Biosyst. Eng. 36, 489-497 (2013).
47. Russell, A. D. & Harries, D. Damage to *Escherichia coli* on exposure to moist heat. Appl. Microbiol. 16, 1394-9 (1968).
48. de Carvalho, C. C. C. R. Whole cell biocatalysts: essential workers from nature to the industry. Microbial Biotechnology 10, 250-263 (2017).
49. Mattei, B., Lira, R. B., Perez, K. R. & Riske, K. A. Membrane permeabilization induced by Triton X-100: The role of membrane phase state and edge tension. Chem. Phys. Lipids 202, 28-37 (2017).
50. Chen, H. et al. Surface display of the thermophilic lipase Tm1350 on the spore of *Bacillus subtilis* by the CotB anchor protein. Extremophiles 19, 799-808 (2015).
51. Parmeggiani, F., Weise, N. J., Ahmed, S. T. & Turner, N. J. Synthetic and therapeutic applications of ammonia-lyases and aminomutases. Chemical Reviews 118, 73-118 (2018).
52. U. Nair, N., A. Denard, C. & Zhao, H. Engineering of enzymes for selective catalysis. Curr. Org. Chem. 14, 1870-1882 (2010).
53. Cheng, L., Mu, W. & Jiang, B. Thermostable L-arabinose isomerase from *Bacillus stearothermophilus* IAM 11001 for D-tagatose production: gene cloning, purification and characterisation. J. Sci. Food Agric. 90, 1327-33 (2010).
54. Zhang, W. et al. Characterization of a novel metal-dependent D-psicose 3-epimerase from *Clostridium scindens* 35704. PLoS One 8, 62987 (2013).
55. Alegre, M. T., Rodriguez, M. C. & Mesas, J. M. Transformation of *Lactobacillus plantarum* by electroporation with in vitro modified plasmid DNA. FEMS Microbiol. Lett. 241, 73-7 (2004).
56. Dische, Z. & Borenfreund, E. A new spectrophotometric method for the detection and determination of keto sugars and trioses. Chem, J Biol 192, 583-587 (1951).

SUPPORTING INFORMATION

TABLE 1

Primers used in this study.

| Primer | Description |
|---|---|
| oJRB7 | Lp_1261_F |
| oJRB8 | Lp_1261_R |
| oJRB10 | Lp_2162_F |
| oJRB11 | Lp_2162_R |
| oJRB14 | Lp_1452_F |
| oJRB15 | Lp_1452_R |
| oJRB20 | Lp_2940_F |
| oJRB21 | Lp_2940_R |
| oJRB34 | Lp_1261ovrlp_R |
| oJRB35 | Lp_1452ovrlp_R |
| oJRB82 | Lp_3014_F |
| oJRB83 | Lp_3014_R |
| oJRB132 | LsLAIovrlp F |
| oJRB133 | LsLAIovrlp R |
| oJRB170 | LsLAI_IC1_F |
| oJRB171 | LsLAI_IC1_R |
| oJRB304 | LsLAI_SEC_F |
| oJRB305 | LsLAI_SEC_R |
| oJRB457 | LsLAI_IC2_F |
| oJRB458 | LsLAI_IC2_R |

TABLE 2

Plasmids used in this study.

| Plasmid | Description | Reference |
|---|---|---|
| pLp_3050Ag85B-E6cwa2 | pSIP401 based plasmid containing an oncofetal antigen and Lp_2578 anchor for *L. plantarum* surface display. | 1 |
| pLp_1261Ag85B-E6 | pSIP401 based plasmid containing invasion and Lp_1261 anchor for *L. plantarum* surface display. | 2 |
| pLp_1452Inv | pSIP401 based plasmid containing invasion and Lp_1452 anchor for *L. plantarum* surface display. | 2 |
| pSIP411 | Lactobacillus inducible plasmid system with broad host SH71 origin. | 3 |
| pJRB01Q-LSH | pSIP401 based plasmid containing LsaraA, sppQ, Lp_2578, SP_3050, His$_6$ tag | This work |
| pJRB02Q-LSH | pSIP401 based plasmid containing LsaraA, sppQ, Lp_2162, SP_3050, His$_6$ tag | This work |
| pJRB03Q-LSH | pSIP401 based plasmid containing LsaraA, sppQ, Lp_2940, SP_3050, His$_6$ tag | This work |
| pJRB04Q-LSH | pSIP401 based plasmid containing LsaraA, sppQ, His$_6$ tag | This work |
| pJRB05Q-LSH | pSIP401 based plasmid containing LsaraA, sppQ, Lp_1261, SP_3050, His$_6$ tag | This work |
| pJRB06Q-LSH | pSIP401 based plasmid containing LsaraA, sppQ, Lp_1452, SP 3050, His$_6$ tag | This work |
| pJRB08Q-LSH | pSIP401 based plasmid containing LsaraA, sppQ, Lp 3014, SP 3050, His$_6$ tag | This work |
| pJRB09Q-LSH | pSIP401 based plasmid containing LsaraA, SP 3050, His$_6$ tag | This work |
| pJRB14Q-LSH | pSIP411 based plasmid containing LsaraA, sppQ, His$_6$ tag | This work |

TABLE 3

Strains used in this study.

| Strain | Description |
|---|---|
| *E. coli* NEB 5α | NEB (Beverly, MA) |
| *L. plantarum* WCFS1 | NIZO Food Research (Kernhemseweg, Netherlands) |
| A1 | *L. plantarum* containing plasmid pJRB01Q-LSH |
| A2 | *L. plantarum* containing plasmid pJRB02Q-LSH |
| A3 | *L. plantarum* containing plasmid pJRB03Q-LSH |
| A4 | *L. plantarum* containing plasmid pJRB05Q-LSH |
| A5 | *L. plantarum* containing plasmid pJRB06Q-LSH |
| A6 | *L. plantarum* containing plasmid pJRB08Q-LSH |
| SEC | *L. plantarum* containing plasmid pJRB09Q-LSH |
| IC1 | *L. plantarum* containing plasmid pJRB04Q-LSH |
| IC2 | *L. plantarum* containing plasmid pJRB14Q-LSH |
| IC2 + PBS | Unmodified strain IC2 |
| IC2 + SDS | Modified strain IC2 permeabilized with 0.01% SDS |

TABLE 4

Native *L. plantarum* anchor proteins used for LsLAI surface display.

| Strain | Anchor protein | Orientation | Type | Ref. |
|---|---|---|---|---|
| A1 | Lp_2578 | C-terminal | LPxTG | 4, 5 |
| A2 | Lp_2162 | C-terminal | LysM | 6 |
| A3 | Lp_2940 | C-terminal | LPxTG | 7 |
| A4 | Lp_1261 | N-terminal | Lipobox | 5, 8 |
| A5 | Lp_1452 | N-terminal | Lipobox | 2 |
| A6 | Lp_3014 | N-terminal | LysM | 2, 9 |

SUPPLEMENTAL REFERENCES

1. Fredriksen, L., Mathiesen, G., Sioud, M. & Eijsink, V. G. H. Cell wall anchoring of the 37-kilodalton oncofetal antigen by *Lactobacillus plantarum* for mucosal cancer vaccine delivery. Appl. Environ. Microbiol. 76, 7359-62 (2010).
2. Fredriksen, L. et al. Surface display of N-terminally anchored invasin by *Lactobacillus plantarum* activates NF-κB in monocytes. Appl. Environ. Microbiol. 78, 5864-71 (2012).
3. Karlskås, I. L. et al. Heterologous protein secretion in lactobacilli with modified pSIP vectors. PLoS One 9, e91125 (2014).
4. Pontes, D. et al. Immune response elicited by DNA vaccination using *Lactococcus lactis* is modified by the production of surface exposed pathogenic protein. PLoS One 9, e84509 (2014).
5. Kuczkowska, K. et al. Immunogenic properties of *Lactobacillus plantarum* producing surface-displayed *Mycobacterium tuberculosis* antigens. Appl. Environ. Microbiol. 83, e02782-16 (2017).
6. Xu, W. et al. Novel surface display system for heterogonous proteins on *Lactobacillus plantarum*. Lett. Appl. Microbiol. 53, 641-648 (2011).
7. Cortes-Perez, N. G. et al. Cell-surface display of E7 antigen from human papillomavirus type-16 in *Lactococcus lactis* and in *Lactobacillus plantarum* using a new cell-wall anchor from lactobacilli. J. Drug Target. 13, 89-98 (2005).
8. Nguyen, H.-M. et al. Display of a β-mannanase and a chitosanase on the cell surface of *Lactobacillus plantarum* towards the development of whole-cell biocatalysts. Microb. Cell Fact. 15, 169 (2016).
9. Kuczkowska, K., Mathiesen, G., Eijsink, V. G. H. & Øynebråten, I. *Lactobacillus plantarum* displaying CCL3 chemokine in fusion with HIV-1 Gag derived antigen causes increased recruitment of T cells. Microb. Cell Fact. 14, 1 (2015).

Figure 16A:
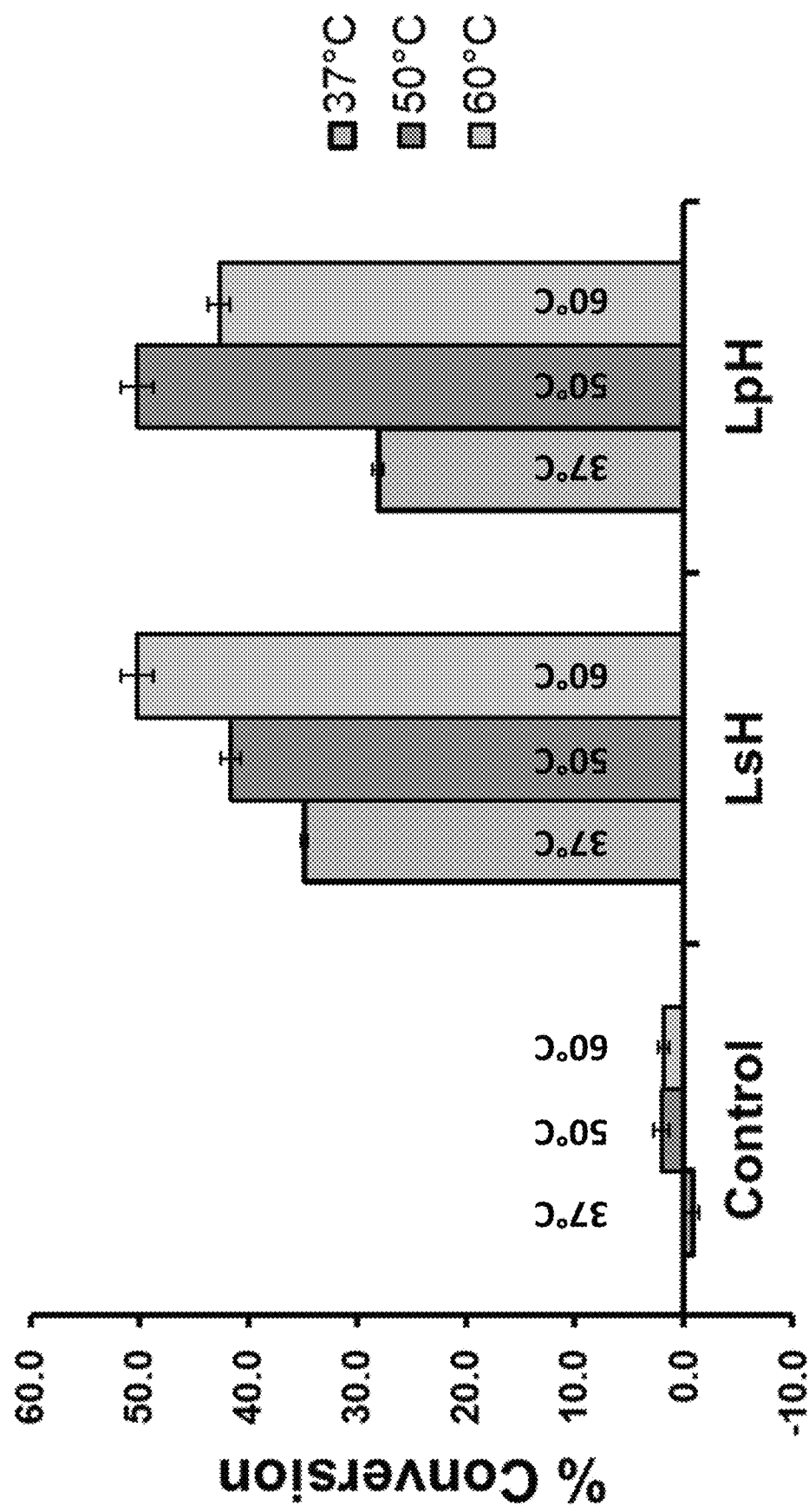
Figure 16B:
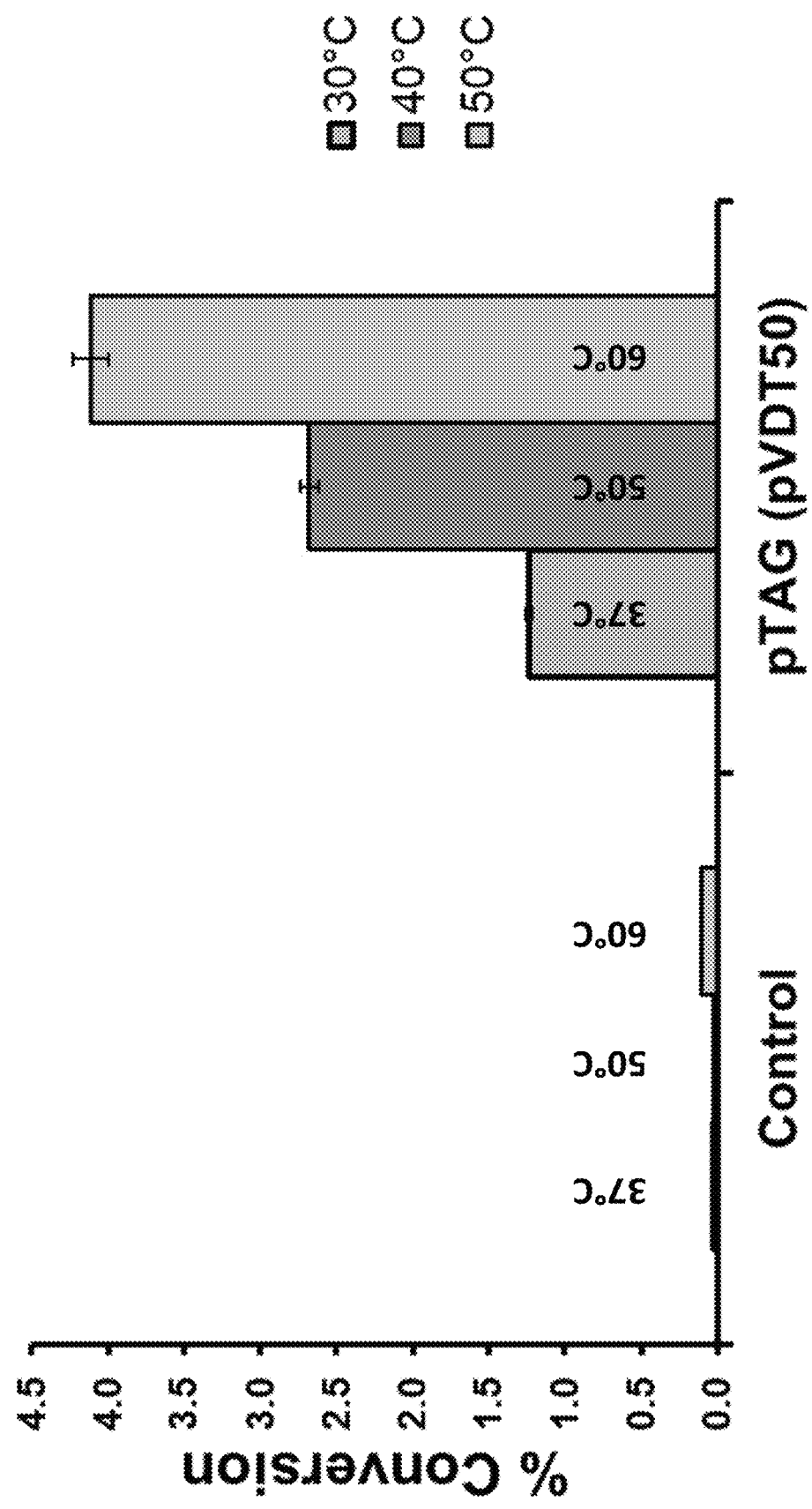

Example 2—Higher Conversions of Galactose to Tagatose at Elevated Reaction Temperature and Adaptation of Lp Cells to Grow at Elevated Temperatures We sought to increase the productivity and yield of the rate sugar tagatose via galactose isomerization by building on the technology we developed in Example 1, we illustrates a high level of tagatose production using whole cell *Lactobacillus plantarum* (Lp) expressing L-arabinose isomerase (LAI) from *L. sakei* (LsH). To achieve higher productivity, we tested another LAI from *L. plantarum*, (LpH), which is more thermostable than LsH (60° C., Chouayekh et al., 2007 vs. 40° C., Rhimi et al., 2010). At 50° C., LpH showed higher conversion (50%) to tagatose than LsH (40%) (FIG. 16A). However, at 60° C. LpH gave lower yield (45%) compared to LsH (52%), suggesting LsH may be a better candidate for tagatose production even at elevated temperatures. We also evaluated *Saccharomyces cerevisiae* (Sc) as biocatalyst for tagatose production using LpH (FIG. 16B). We tested the production of tagatose at 30, 40 and 50° C. Though we saw increase in tagatose production with increase in temperature, the max overall yield observed was only 4.2% at 50° C. This is lower than what was observed with Lp.

Figure 16C:
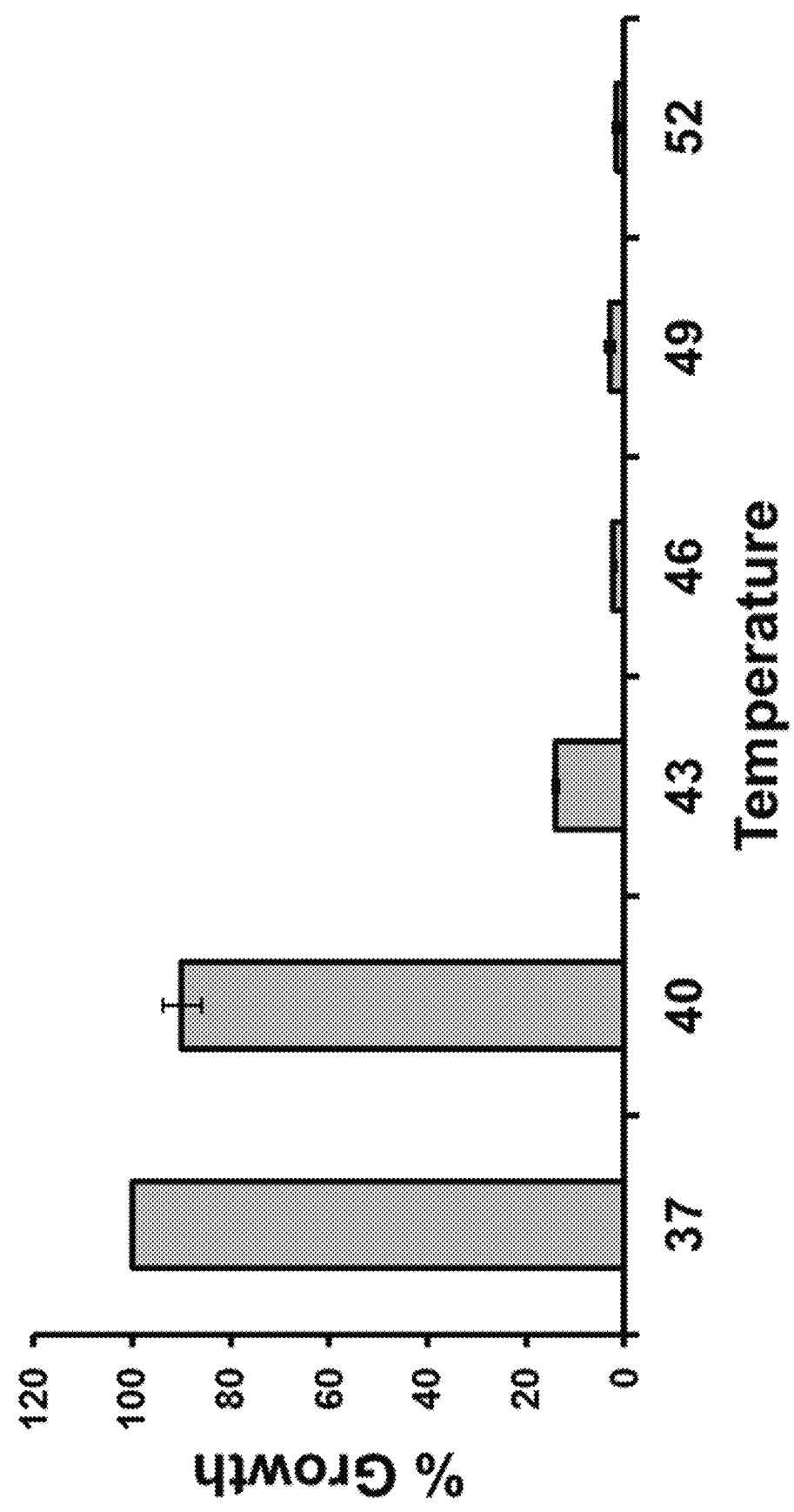
Figure 16D:
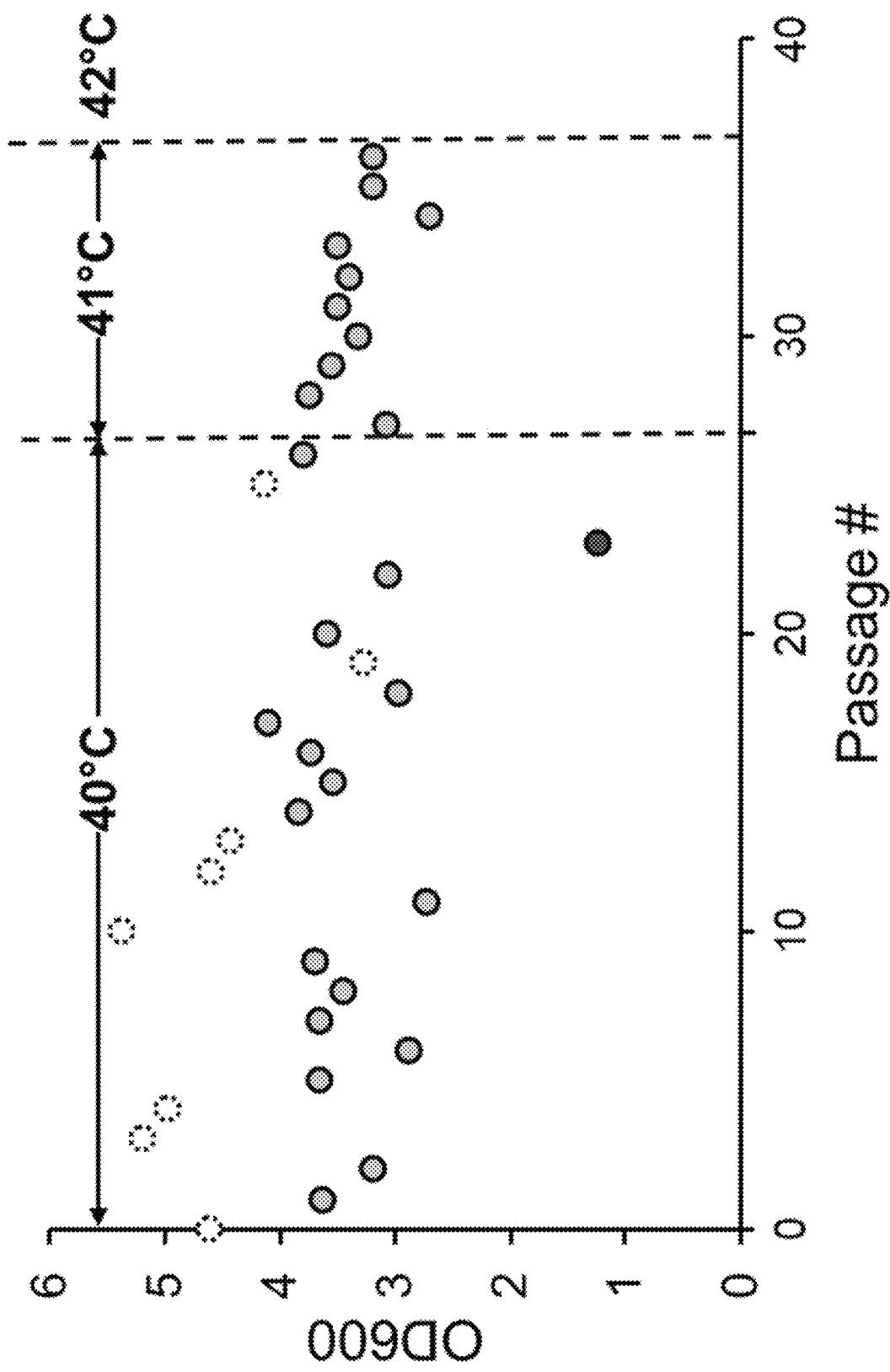

To push the Lp-LsH system to operate at higher temperature, our goal was to adapt Lp for growth at elevated temperatures. We first evaluated the growth of Lp at different temperatures (FIG. 16C). We observed significant growth defect (86%) at 43° C., with no growth at >46° C. To improve the growth at higher temperatures, we initiated adaptive lab evolution (ALE) of Lp beginning the growth at 37° C. and gradually increasing the temperature (FIG. 16D). Thus far, we have been able to adapt Lp to consistently grow till 41° C. Currently, evolved strain is being adapted to grow at 42° C.

REFERENCES

Chouayekh H. et al., "Characterization of an L-arabinose isomerase from the *Lactobacillus plantarum* NC8 strain showing pronounced stability at acidic pH," FEMS Microbiol. Lett. 2007 December; 277(2):260-7.

Rhimi M. et al., "The acid tolerant L-arabinose isomerase from the food grade *Lactobacillus sakei* 23K is an attractive D-tagotose producer," Bioresour. Technol. 2010 December; 101(23):9171-7.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

What is claimed is:

1. A microbial cell comprising: a recombinant exogenous L-arabinose isomerase enzyme, the microbial cell expressing the enzyme cytoplasmically such that the enzyme is effective to cytoplasmically catalyze the isomerization of D-galactose to tagatose; and at least one modification to the microbial cell effective to facilitate movement of exogenous D-galactose into the cell, wherein the enzyme has at least 90% sequence identity with SEQ ID NO: 1.

2. The microbial cell of claim 1, wherein the enzyme is not surface bound or secreted.

3. The microbial cell of claim 1, wherein the enzyme is *Lactobacillus sakei* L-arabinose isomerase, or a variant thereof having at least 90% identity with *Lactobacillus sakei* L-arabinose isomerase.

4. The microbial cell of claim 1, wherein the enzyme is engineered to exhibit increased catalytic efficiency for D-galactose substrate.

5. The microbial cell of claim 1, wherein the microbial cell is a gram positive bacterial cell selected from *Lactobacillus* spp., *Bacillus* spp., *Corynebacterium* spp., and *Brevibacterium* spp.

6. The microbial cell of claim 1, wherein the microbial cell is *Lactobacillus plantarum*.

7. The microbial cell of claim 1, wherein the microbial cell is a gram negative bacterial cell selected from *Escherichia* spp., *Rhodobacter* spp., *Zymomonas* spp., *Vibrio* spp., *Agrobacterium* spp., *Paracoccus* spp., and *Pseudomonas* spp.

8. The microbial cell of claim 1, wherein the microbial cell is *Escherichia coli*.

9. The microbial cell of claim 1, wherein the microbial cell is a yeast cell selected from *Saccharomyces* spp., *Schizosaccharomyces* spp., *Pichia* spp., *Phaffia* spp., *Kluyveromyces* spp., *Candida* spp., *Talaromyces* spp., *Brettanomyces* spp., *Pachysolen* spp., *Debaryomyces* spp., or *Yarrowia* spp.

10. The microbial cell of claim 1, wherein the microbial cell has been permeabilized by treating the microbial cell with a detergent at a concentration of the detergent is that is below the detergent's critical micelle concentration (CMC).

11. The microbial cell of claim 1, wherein the microbial cell has been modified to overexpress an exogenous sugar transporter for D-galactose.

12. The microbial cell of claim 1, wherein the microbial cell has been modified to comprise one or more genetic modifications that increase the membrane permeability of the microbial cell for D-galactose.

13. The microbial cell of claim 1, wherein the microbial cell has been permeabilized by treating the microbial cell with lysozyme.

14. The microbial cell of claim 1, further comprising an exogenous galactose, an exogenous disaccharide comprising galactose or an exogenous oligosaccharide comprising galactose.

15. A method for catalyzing isomerization of galactose to tagatose, comprising: providing a feedstock comprising galactose to a culture of the microbial cell of claim 1, and recovering tagatose from the culture.

16. The method of claim 15, wherein the feedstock comprises galactose in the range of from about 100 mM to about 600 mM.

17. The method of claim 15, wherein the feedstock comprises a disaccharide or oligosaccharide comprising galactose.

18. The method of claim 15, wherein the culture is maintained at a temperature greater than 42° C. for at least 2 hours.

19. The method of acclaim 15, wherein the amount of galactose converted to tagatose after 24 hours is at least 50%.

20. A method for preparing a microbial cell comprising: (i) engineering the microbial cell to express cytoplasmically an exogenous L-arabinose isomerase enzyme; and (ii) treating the engineered microbial cell with a detergent at a concentration that is below the detergent's critical micelle concentration (CMC).

* * * * *

UNITED STATES PATENT AND TRADEMARK OFFICE
CERTIFICATE OF CORRECTION

PATENT NO. : 11,834,692 B2
APPLICATION NO. : 17/168499
DATED : December 5, 2023
INVENTOR(S) : Nikhil U. Nair and Josef R. Bober It is certified that error appears in the above-identified patent and that said Letters Patent is hereby corrected as shown below:

On the Title Page

Column 1, item (73), In The Assignee:
"Trustees of Tufts College, Medford, WI (US)" should be --Trustees of Tufts College, Medford, MA (US)--

Signed and Sealed this
Ninth Day of July, 2024

Katherine Kelly Vidal
*Director of the United States Patent and Trademark Office*